(12) United States Patent
Drummond et al.

(10) Patent No.: US 9,968,694 B2
(45) Date of Patent: May 15, 2018

(54) COMPOSITIONS AND METHODS FOR NON-INVASIVE IMAGING

(71) Applicant: MERRIMACK PHARMACEUTICALS, INC., Cambridge, MA (US)

(72) Inventors: Daryl C. Drummond, Lincoln, MA (US); Dmitri B. Kirpotin, Revere, MA (US); Thomas Wickham, Groton, MA (US); Bart S. Hendriks, Belmont, MA (US); Samuel Agresta, Lexington, MA (US); Helen Lee, Boston, MA (US); Daniel F. Gaddy, Cambridge, MA (US)

(73) Assignee: Merrimack Pharmaceuticals, Inc., Cambridge, MA (US)

( * ) Notice: Subject to any disclaimer, the term of this patent is extended or adjusted under 35 U.S.C. 154(b) by 9 days.

(21) Appl. No.: 15/340,761

(22) Filed: Nov. 1, 2016

(65) Prior Publication Data

US 2017/0112950 A1    Apr. 27, 2017

Related U.S. Application Data

(62) Division of application No. 14/395,345, filed as application No. PCT/US2013/037033 on Apr. 17, 2013, now Pat. No. 9,511,155.

(60) Provisional application No. 61/625,670, filed on Apr. 17, 2012, provisional application No. 61/696,560, filed on Sep. 4, 2012, provisional application No. 61/798,855, filed on Mar. 15, 2013.

(51) Int. Cl.
| | |
|---|---|
| *A61K 51/12* | (2006.01) |
| *C07C 337/08* | (2006.01) |
| *A61K 51/04* | (2006.01) |
| *A61K 9/127* | (2006.01) |
| *A61K 31/4745* | (2006.01) |
| *A61K 31/704* | (2006.01) |

(52) U.S. Cl.
CPC ........ *A61K 51/0478* (2013.01); *A61K 9/1271* (2013.01); *A61K 31/4745* (2013.01); *A61K 31/704* (2013.01); *A61K 51/1234* (2013.01); *C07C 337/08* (2013.01)

(58) Field of Classification Search
USPC .................. 424/1.21, 9.2, 450; 514/283, 34; 534/10; 564/19
See application file for complete search history.

(56) References Cited

U.S. PATENT DOCUMENTS

| | | | |
|---|---|---|---|
| 3,478,035 A | 11/1969 | Barrett | |
| 5,843,400 A * | 12/1998 | Fujibayashi | ........... A61K 51/04 424/1.11 |
| 5,922,350 A | 7/1999 | Janoff et al. | |
| 8,147,867 B2 | 4/2012 | Hong et al. | |
| 8,329,213 B2 | 12/2012 | Hong et al. | |
| 2005/0112065 A1 | 5/2005 | Drummond et al. | |
| 2011/0098353 A1 | 4/2011 | Dilworth et al. | |
| 2011/0305632 A1* | 12/2011 | Donnelly | ............... A61K 38/08 424/1.65 |
| 2013/0209481 A1 | 8/2013 | Zhou et al. | |

FOREIGN PATENT DOCUMENTS

| | | |
|---|---|---|
| WO | 2003101474 A1 | 12/2003 |
| WO | 2004004635 A2 | 1/2004 |
| WO | 2010066010 A1 | 6/2010 |
| WO | 2011006510 A1 | 1/2011 |
| WO | 2011109334 A2 | 9/2011 |
| WO | 2012078695 A2 | 6/2012 |
| WO | 2012079582 A1 | 6/2012 |

OTHER PUBLICATIONS

U.S. Appl. No. 14/181,583, filed Feb. 14, 2014, 20140170075, Pending.
U.S. Appl. No. 14/395,345, filed Apr. 17, 2013, 20150093328, U.S. Pat. No. 9,511,155, Issued.
U.S. Appl. No. 14/964,571, filed Dec. 9, 2015, 20160346272, Pending.
U.S. Appl. No. 15/031,643, filed Oct. 23, 2014, 20160303264, Pending.
U.S. Appl. No. 15/375,039, filed Dec. 9, 2016, Pending.
Furukawa, Takako, et al. [English Abstract only] Development of Imaging Technology in Life Science. IX. Advantages of RI and Fluorescence in Imaging Instruments for Radiation Measurement in Life Sciences (5) National Institute of Radiological Sciences, 4-9-1 Anagawa, Inage-ku, Chiba-shi Chiba Pref. 263-8555, Japan; p. 45.
Harrington, Kevin J., et al. "Effective Targeting of Solid Tumors in Patients with Locally Advanced Cancers by Radiolabeled Pegylated Liposomes" Clinical Cancer Research vol. 7; pp. 243-254, Feb. 2001.
International Search Report of PCT/US2013/037033, dated Aug. 28, 2013.
International Search Report for PCT/US2014/062007, dated Jan. 9, 2015.
Kiropotin, D., et al. Anytibody Targeting of Long-Circulating Lipidic Nanoparticles Does Not Increase Tumor Localization but Does Increase Internalization in Animal Models, Cancer Res 2006; 66:(13) Jul. 1, 2006; pp. 6732-6740.
Lee, H., et al. "A Novel 64Cu-Liposome PET Agent (MM-DX-929) Predicts Response to Liposomal Chemotherapeutics in Preclinical Breast Cancer Models" Dec. 4-8, 2012. Retrived from Internet: <http://origin-qps.onstreammedia.com/origin/multivu_archive/ENR/FX-20121210-DC26113-01.pdf> [Retrieved Dec. 13, 2014]; figure 3.

(Continued)

*Primary Examiner* — Johann R Richter
*Assistant Examiner* — Courtney A Brown
(74) *Attorney, Agent, or Firm* — Honigman Miller Schwartz and Cohn LLP; Fernando Alberdi; Cynthia M. Bott

(57) ABSTRACT

The present invention relates to a novel composition useful in targeted diagnostic and/or therapy of a target site, such as cancerous tissue. The composition and methods disclosed herein find particular use in diagnosing and imaging cancerous tissue. The present invention provides a new diagnostic tool for the utilization of positron emission tomography (PET) imaging technique.

20 Claims, 52 Drawing Sheets

(56) References Cited

OTHER PUBLICATIONS

Noble, Charles O., et al. "Characterization of highly stable liposomal and immunoliposomal formulations of vincristine and vinblastine" Cancer Chemother Pharmacol. 64 (2009), pp. 741-751.
Petersen, Anncatrine L., et al. 64Cu loaded liposomes as positron emission tomography imaging agents. Biomaterials 32 (2011) pp. 2334-2341.
Supplementary European Search Report for EP13778788 dated Nov. 4, 2015.
Winkelmann, W. H., et al. "Anticoccidial Activity of Dithiosemicarbazones" Arzneimittel Forschung, Drug Research, vol. 27, No. 5 (1977), pp. 950-967.

* cited by examiner

COMPOSITIONS AND METHODS FOR NON-INVASIVE IMAGING

RELATED APPLICATIONS

This application is a divisional application of U.S. application Ser. No. 14/395,345 filed Oct. 17, 2014, now U.S. Pat. No. 9,511,155, issued on Dec. 6, 2016, which is a 35 U.S.C. § 371 United States National Phase filing of, and claims priority to, PCT International Application No. PCT/US2013/037033 filed Apr. 17, 2013, which claims the benefit under 35 U.S.C. § 119 of U.S. Provisional Patent Application Nos. 61/625,670, filed Apr. 17, 2012, 61/696,560, filed Sep. 4, 2012, and 61/798,855, filed Mar. 15, 2013. The contents of each of the foregoing applications are incorporated herein by reference in their entireties.

BACKGROUND

Liposomes have proved a valuable tool for delivering various pharmacologically active molecules, such as antineoplastic agents, to cells, organs, or tumors. However, it has been found that deposition of liposomes into tumors can be highly variable between not only tumors of different subtypes between patients, but also between tumors of similar subtype within the same patient. The outcome of treatment with liposomally-delivered therapeutic agents can therefore be somewhat unpredictable for a given patient.

Liposome delivery has been shown to improve the pharmacokinetic profile and widen the therapeutic index of certain anticancer drugs, especially the anthracycline class. Improved efficacy is in part a result of passive targeting to tumor sites based on the enhanced permeability and retention (EPR) effect. To fully exploit this process, drug carriers should be engineered to retain drug while circulating, thereby preventing premature drug release before accumulating in the tumor but still allowing for release of drug once in the vicinity of the tumor. Antibody-targeted nanoparticles, such as immunoliposomes against HER2 or epidermal growth factor receptor, represent another strategy for more efficient drug delivery to tumor cells.

It has been found, however, that deposition of liposomal drugs into tumors varies. Tumors that have higher drug deposition will have improved clinical outcomes. Liposomal drugs have been shown to enter tumors via a mechanism termed the enhanced permeability and retention (EPR) effect whereby liposomes can preferentially escape from the bloodstream into the tumor interstitium via leaky tumor vasculature and then become trapped in the tumor by virtue of their large size and the lack of functional lymphatics. However, the degree to which liposomal particles can deposit into tumors has been shown to be highly variable in both preclinical tumor models and in clinical studies whereby liposomes have been used as imaging agents to quantify the level and variability of tumor deposition. The invention provides liposomal imaging agents that can be used to predict which patients' tumors will have low or high deposition of liposomal drugs and ultimately which will benefit from a particular liposomal drug.

Non-invasive methods for determining whether a liposomally-delivered therapeutic agent is suitable for use in a patient before treatment (e.g., to predict clinical outcomes of targeted and untargeted liposomal therapeutics) are therefore needed.

SUMMARY

The present invention provides compositions and methods for non-invasive imaging, and more particularly, non-invasive imaging for liposomal therapeutics. Such compositions and methods are useful in imaging cancer or another disease, and/or for drug delivery to a target site, e.g., cancerous tissue.

Other features and advantages will be apparent from the detailed description, and from the claims.

Provided in one aspect is the DEAP-ASTC compound of formula I:

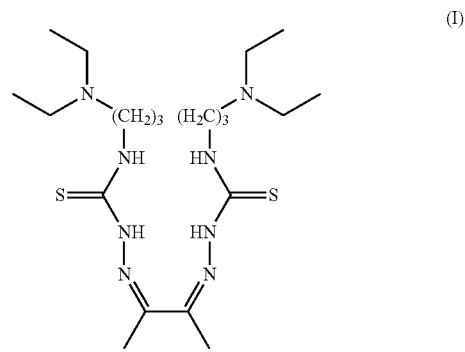

or a pharmaceutically acceptable salt thereof. In one embodiment the compound is stored at a temperature of −20° C., −4° C., room temperature (22-25° C.), 30° C., 37° C. or 40° C. In one embodiment the compound is stored for 3 months, 4 months, 5 months, or 6 months. In another embodiment, following storage for 3 months, 4 months, 5 months, or 6 months days at a temperature of from 4° C. to 40° C., less than 15% of the compound has degraded. In one embodiment the % of the compound that has degraded is measured by high performance liquid chromatography.

Provided in another aspect is a DEAP-ASTC compound of formula II:

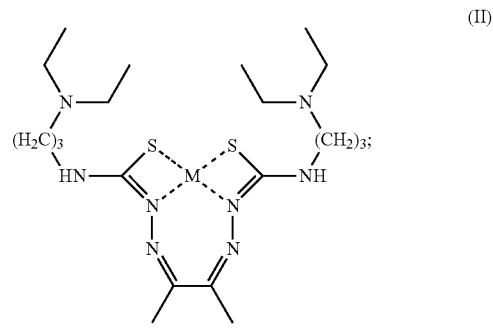

in which M is a metal ion with a valency of 2 or 3 or 4, or a metal oxide ion. In one embodiment, M is a divalent cation, e.g., a copper cation. In another embodiment, M is $Cu^{2+}$. In one embodiment, M is a radioisotope, e.g., $^{64}Cu$ or $^{67}Cu$, or another suitable isotope of a divalent cation.

Provided in another aspect is a composition comprising liposomes in an aqueous medium (e.g., a pharmaceutically acceptable medium) said liposomes each having an interior space and a membrane separating said interior from said medium, said membrane comprising one or more lipids; and a compound of formula I or formula II (or formula III, infra), either with or without a chelated divalent cation, entrapped in at least one liposome of the liposomes in the composition. In one embodiment, where a divalent metal cation is chelated, the composition comprises at least about 0.1 µCi of radioactivity. In another embodiment, M is a radioisotope of $Cu^{2+}$ selected from $^{64}Cu$ and $^{67}Cu$. In yet another embodiment, the composition comprises about 0.01, 1, 2, 3, 4, 5, 10, 15 or 20 µCi of radioactivity. In various embodiments the membranes comprises cholesterol and a phosphatidylcholine. In other embodiments, the liposomes are stable after a storage period of 3 months, 4 months, 5 months, or 6 months, wherein stability is measured by a functional readout, e.g., in vivo stability or loadability. A liposome is considered loadable (stable) if, after loading of $^{64}Cu$:4-DEAP-ATSC into the liposomes, about 90% of $^{64}Cu$:4-DEAP-ATSC is in the liposome fraction after size exclusion chromatography. In one embodiment, the membranes of the liposomes comprise cholesterol and a phosphatidylcholine. In another embodiment, the membranes of the liposomes comprise a non-hydrolysable lipid. An exemplary non-hydrolysable lipid is a sphingolipid. In yet another embodiment, the membranes of the liposomes comprise one or more of sphingomyelin, HSPC, DSPC and a non-hydrolysable lipid.

In various aspects, the liposomes in an aqueous medium are prepared as unloaded liposomes prior to the compound of Formula III being entrapped in the at least one liposome, and the unloaded liposomes are stable after a storage period of 3 months, 4 months, 5 months, or 6 months, wherein stability is measured by a functional readout obtained following loading of the liposomes with the compound of Formula III after the storage period. The functional readout may be loading efficiency, e.g., of $^{64}Cu$:4-DEAP-ATSC into the liposomes, wherein a liposome is stable if, after loading, at least 90% of $^{64}Cu$:4-DEAP-ATSC is in the liposome fraction after size exclusion chromatography. IN other aspects the liposomes in the aqueous medium are prepared as unloaded liposomes prior to the compound of Formula III being entrapped in the at least one liposome, and a plurality of the unloaded liposomes comprise either or both of TEA-SOS and ammonium sulfate in their interior spaces.

In any of the liposomal compositions or methods herein provided, the liposomes may comprise either or both of TEA-SOS and ammonium sulfate in their interior spaces in an amount sufficient to form an electro-chemical gradient across the membrane.

In another embodiment, the compound is a compound of formula III:

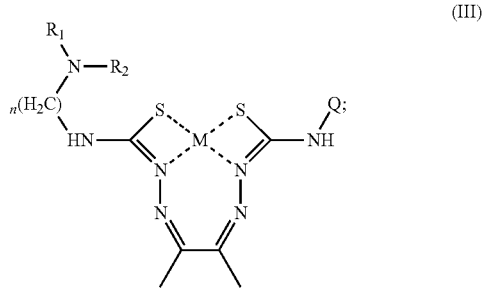

(III)

in which: Q is H, substituted or unsubstituted $C_1$-$C_6$alkyl, or —$(CH_2)_n$—$NR_3R_4$; $R_1$, $R_2$, $R_3$ and $R_4$ are each independently selected from H, substituted or unsubstituted $C_1$-$C_6$alkyl, or substituted or unsubstituted aryl or wherein either or both of (1) $R_1$ and $R_2$ and (2) $R_3$ and $R_4$ are joined to form a heterocyclic ring; M is a metal cation with a valency of 2 or 3 or 4, and n is independently, for each occurrence, an integer from 1 to 5. In various embodiments, Q is —$(CH_2)_n$—$NR_3R_4$. In other embodiments, M is $Cu^{2+}$. In other embodiments the composition comprises at least about 0.1 µCi of radioactivity.

In other embodiments, following storage for at least 90 days at a temperature from 4° C. to 40° C., less than 15% of the compound is degraded. For example, the compound in some embodiments may be stored at a room temperature of about 25° C. or incubated at about 37° C. In one embodiment, the % of the compound that has degraded is measured by high performance liquid chromatography. In some embodiments, following storage for 4 months, 5 months, or 6 months, less than 15% of the compound is degraded.

In another aspect, a method is provided for preparing a liposomal imaging agent, the method comprising:
(a) providing a first solution comprising a quantity of a compound of Formula III,

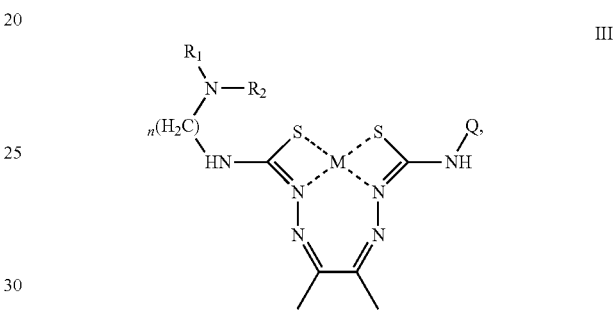

III in which
Q is H, substituted or unsubstituted $C_1$-$C_6$alkyl, or —$(CH_2)_n$—$NR_3R_4$;
$R_1$, $R_2$, $R_3$ and $R_4$ are each independently selected from H, substituted or unsubstituted $C_1$-$C_6$alkyl, or substituted or unsubstituted aryl or wherein either or both of (1) $R_1$ and $R_2$ and (2) $R_3$ and $R_4$ are joined to form a heterocyclic ring;
M absent or is a metal ion, and
n is independently, for each occurrence, an integer from 1 to 5; and
(b) providing a preparation of liposomes in a aqueous medium, a plurality of the liposomes each having an interior space and a membrane separating the interior space from the medium, the interior space comprising a second solution creating an electro-chemical gradient across the membrane, and either (c) where M is present, preparing a mixture by combining the first solution with the preparation of liposomes, and incubating the mixture under conditions such that a fraction of the quantity of the compound of Formula III becomes encapsulated by at least one liposome of the plurality of liposomes, to form a liposomal imaging agent, or
(d) where M is absent, preparing a mixture by combining the first solution with the preparation of liposomes, and incubating the mixture under conditions such that a fraction of the quantity of the compound of Formula III becomes encapsulated by at least one liposome of the plurality of liposomes, and subsequently adding a solution comprising radioactive metal ion to the at least one liposome so that radioactive metal ion becomes encapsulated by the at least one liposome to that to form a liposomal imaging agent. In certain aspects of this method, prior to the mixture being prepared, the second solution is essentially free of any metal chelating moiety. In other aspects, prior to the mixture being prepared, the first solution is essentially free of lipid. In still other aspects, the conditions include a temperature of 40° C. or above, or 60° C. or above. In these aspects, the imaging agent so prepared may be suitable for use by injection into a patient without fractionation, other than sterile filtration, subsequent to the preparation of the mixture. In additional aspects, prior to becoming encapsulated by at least one liposome, the compound of Formula III is uncharged, and subsequent to becoming encapsulated by at least one liposome, the compound of Formula III is charged. In various embodiments, subsequent to the incubating, the mixture is subjected to filtration that is optionally paper filtration, membrane filtration, or gel filtration. In yet another aspect, the fraction of the compound of Formula III in the first solution that does not become encapsulated is less than 15% or less than 10%. In various aspects of this method, the preparation of liposomes of (b) comprises within a plurality of the liposomes therein, an antineoplastic therapeutic agent, which is optionally a chemotherapeutic agent such as doxorubicin or irinotecan.

Another method of preparing a liposomal imaging agent is provided, the method comprising: (a) providing a first solution comprising a quantity of an uncharged composition that is radioactive metal chelated by a chelator; and (b) providing a preparation of liposomes in a aqueous medium, a plurality of said liposomes each having an interior space and a membrane separating said interior space from said medium, said interior space comprising a second solution creating an electro-chemical gradient across the membrane, and (c) preparing a mixture by combining the first solution with the preparation of liposomes, and incubating the mixture under conditions such that a fraction of the quantity of the composition becomes encapsulated by at least one liposome of the plurality of liposomes and becomes charged, to form a liposomal imaging agent.

Also provided is a method of imaging a tissue in a patient, the method comprising:
(a) injecting the patient with a liposomal imaging agent comprising the composition of claim 9 in an amount sufficient to provide a dose of at least 0.1 µCi of radioactivity to the patient; and
(b) within 48 hours following the injection, scanning the location of the tissue using a scanning method that detects radiation emitted by the radioisotope to obtain an image of the tissue. In certain aspects of this method the tissue is a tumor.

Further provided is a method of determining whether a patient having a tumor should be treated with an antineoplastic liposomal therapeutic agent, the method comprises (a) injecting the patient with a liposomal imaging agent comprising the composition of claim 9 in an amount sufficient to provide a dose of at least 0.1 µCi of radioactivity to the patient;
(b) within 48 hours following the injection, scanning the location of the tumor using a scanning method that detects radiation emitted by the radioisotope to obtain an image; and
(c) examining the image. If the image shows that the liposomal imaging agent is deposited in the tumor at levels higher than background, then the patient is determined to be a patient that should be treated with the liposomal therapeutic agent. Background may be determined by scanning tumor-free muscle tissue within 48 hours following the injection. In various aspects, if the image shows that the liposomal imaging agent is deposited in the tumor at levels higher than background, then the patient is treated with the liposomal therapeutic agent and if the image shows that the liposomal imaging agent is not deposited in the tumor at levels higher than background, then the patient is not treated with the liposomal therapeutic agent.

Also provided is a kit for preparing a liposomal imaging agent, the kit comprising a package containing:
(a) a first container comprising a compound of Formula III

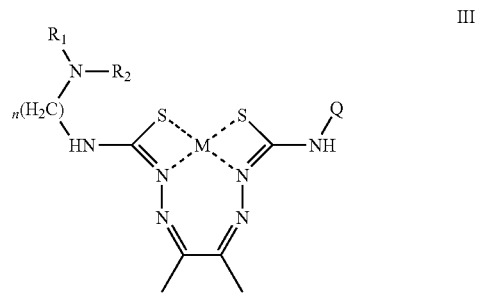

in which
M is absent;
Q is H, substituted or unsubstituted $C_1$-$C_6$alkyl, or —$(CH_2)_n$—$NR_3R_4$; $R_1$, $R_2$, $R_3$ and $R_4$ are each independently selected from H, substituted or unsubstituted $C_1$-$C_6$alkyl, or substituted or unsubstituted aryl or wherein either or both of (1) $R_1$ and $R_2$ and (2) $R_3$ and $R_4$ are joined to form a heterocyclic ring; and n is independently, for each occurrence, an integer from 1 to 5; and
(b) a second container comprising a preparation of liposomes in a pharmaceutically acceptable medium, said liposomes having an interior space and a membrane separating said interior from said medium, said interior space comprising a solution creating an electro-chemical gradient across the membrane. The kit may further comprise instructions for, in sequence: (i) combining the compound of formula III with a metal ion to yield a compound of formula III in which M is not absent and is the metal ion; (ii) preparing a mixture by combining the compound of formula III in which M is the metal ion with the preparation of liposomes, and incubating the mixture under conditions such that the compound of formula III in which M is the metal ion becomes encapsulated in liposomes of the preparation of liposomes; and (iii) administering the encapsulated compound of formula III in which M is the metal ion to the patient.

In additional embodiments, a method of preparing a liposomal imaging agent is provided, the method comprising: (a) providing a first solution comprising a quantity of an uncharged composition that is radioactive metal chelated by a chelator; and (b) providing a preparation of liposomes in a aqueous medium, a plurality of said liposomes each having an interior space and a membrane separating said interior space from said medium, said interior space comprising a second solution creating an electro-chemical gradient across the membrane, and (c) preparing a mixture by combining the first solution with the preparation of liposomes, and incubating the mixture under conditions such that a fraction of the quantity of the composition becomes encapsulated by at least one liposome of the plurality of liposomes and becomes charged, to form a liposomal imaging agent.

BRIEF DESCRIPTION OF THE DRAWINGS

FIG. 20A shows functional stability of HSPC, DSPC, and sphingomyelin formulations at 1 to 6 months storage at varying temperatures, and illustrates that the HSPC—ammonium sulfate formulation is functionally stable for at least 15 months when stored at 4° C.

FIG. 20B shows degradation of lipid in HSPC and DSPC formulations (as measured by HPLC/ELSD) after 1 to 5 months at varying storage temperatures.

FIG. 20C shows stability of a $^{64}$Cu-DEAP-ATSC-loaded HSPC liposome in vivo after up to 6 months storage of the liposome preparation (without radiolabel) at room temperature.

FIG. 20D shows the stability of sphingomyelin formulations up to 3 months of storage at 4° C.

FIG. 20E shows the stability of sphingomyelin formulations up to 3 months of storage at 30° C.

FIG. 20F shows the stability of sphingomyelin formulations up to 3 months of storage at 37° C.

FIG. 20G shows storage stability of PEG-DSGE, PEG-DSG, or a liposomal formulation made by post-insertion of (reduced amount) PEG-DSPE into preformed liposomes.

FIG. 21A shows the effect of loading gradient strengths on the $^{64}$Cu:4-DEAP-ATSC loading efficiency of HSPC liposomes.

FIG. 21B shows the effect of loading gradient strengths on the $^{64}$Cu:4-DEAP-ATSC loading efficiency of DSPC liposomes.

FIG. 21C shows the effect of loading gradient strengths on the $^{64}$Cu:4-DEAP-ATSC loading efficiency of liposomes comprising sphingomyelin.

DETAILED DESCRIPTION

Figure 1:
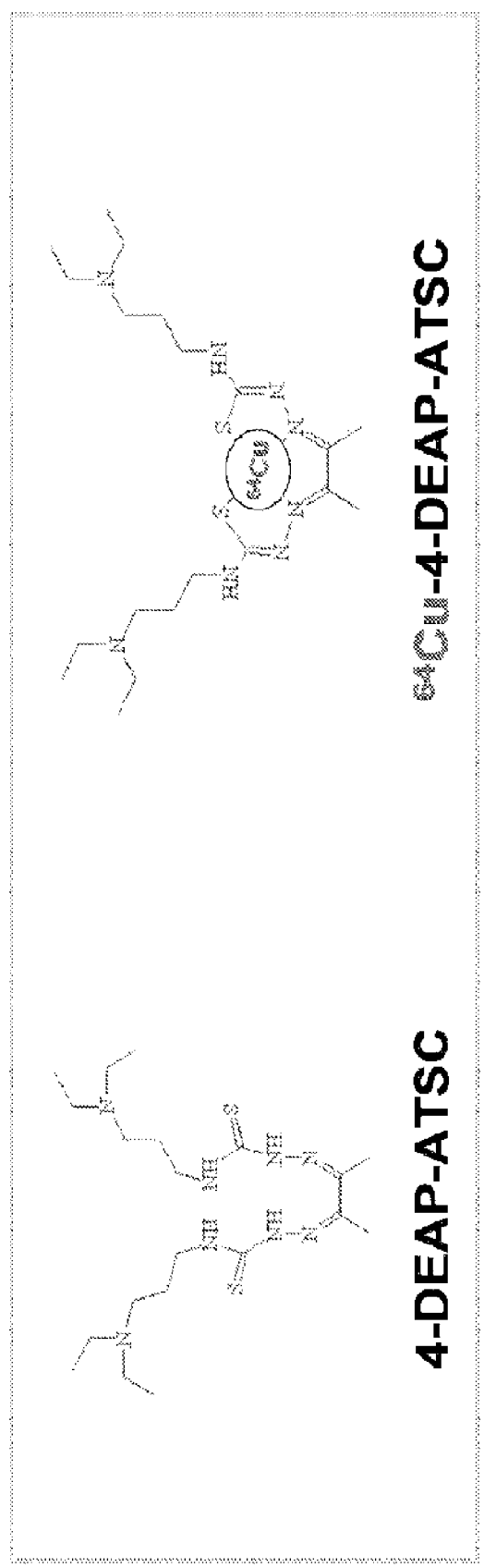
FIG. 1 shows the molecular structure of a representative chelator alone, and when complexed with $^{64}$Cu.

The present invention provides compositions and methods for non-invasive imaging, and more particularly, non-invasive imaging for liposomal therapeutics.

The invention is based, at least in part, on the discovery that diacetyl 4,4'bis (3-(N,N-diethylamino)propyl)thiosemicarbazone (4-DEAP-ATSC) is useful as a non-invasive imaging reagent for determining whether a subject is a candidate for treatment with a liposomal therapeutic, as well as for monitoring treatment of a subject with a liposomal therapeutic.

DEFINITIONS

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

By "loading" is meant the process of incorporating a chelating agent, chemical agent, therapeutic agent, nucleic acid, and/or polypeptide into an exosome, liposome, or vesicle.

By "nanoparticle" is meant a liposome, exosome, polymersome, microvesicle, apoptotic body, or other lipid or polymer shell structure that constitutes a membrane surrounding an aqueous core. Such nanoparticles may be either synthetically made, or endogenously derived from a cell or a population of cells.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Liposomal Imaging Agents

In a general aspect, the invention provides liposomal imaging agents having at least two components: (1) A liposome, which will be suspended or solubilized in a liquid medium (such as a buffer or other pharmaceutically acceptable carrier); (2) a chelator moiety capable of chelating a metal ion; and optionally (3) a metal ion suitable for imaging or otherwise assessing the in vitro or in vivo uptake of the liposomal imaging agent into cells, organs, or tumors. In some embodiments, the metal ion has a valency of 2 or 3 or 4. In exemplary embodiments, the metal ion has a valency of 2.

Liposomes

The liposomes of the liposomal imaging agents disclosed herein can be any liposome known or later discovered in the art. In general, the liposomes can have any liposome structure, e.g., structures having an inner space sequestered from the outer medium by one or more lipid bilayers, or any microcapsule that has a semi-permeable membrane with a lipophilic central part where the membrane sequesters an interior. A lipid bilayer can be any arrangement of amphiphilic molecules characterized by a hydrophilic part (hydrophilic moiety) and a hydrophobic part (hydrophobic moiety). Usually amphiphilic molecules in a bilayer are arranged into two dimensional sheets in which hydrophobic moieties are oriented inward relative to the sheet, while hydrophilic moieties are oriented outward. Amphiphilic molecules forming the liposomes disclosed herein can be any known or later discovered amphiphilic molecules, e.g., lipids of synthetic or natural origin or biocompatible lipids. Liposomes disclosed herein can also be formed by amphiphilic polymers and surfactants, e.g., polymerosomes and niosomes. For the purpose of this disclosure, without limitation, these liposome-forming materials also are referred to as "lipids".

In certain embodiments, the liposome comprises hydrogenated soy phosphatidylcholine (HSPC), cholesterol, and poly(ethylene glycol) (PEG) (Mol. weight 2000)-derivatized distearoylphosphatidylethanolamine (PEG-DSPE) (3:1:0.05 molar ratio).

In certain embodiments, the liposome comprises poly (ethylene glycol)-derivatized phosphatidylethanolamines such as 1,2-distearoyl-sn-glycero-3-phosphatidyl ethanolamine-N-[methoxy(poly(ethylene glycol)-2000)] (ammonium salt); 1,2-dipalmitoyl-sn-glycero-3-phosphatidyl ethanolamine-N-[methoxy(poly(ethylene glycol)-2000)] (ammonium salt); 1,2-dimyristoyl-sn-glycero-3-phosphatidyl ethanolamine-N-[methoxy(poly(ethylene glycol)-2000)] (ammonium salt); or 1,2-dioleoyl-sn-glycero-3-phosphatidyl ethanolamine-N-[methoxy(poly(ethylene glycol)-2000)] (ammonium salt). In certain embodiments, the molecular weight of PEG is 750, 1000, 1500, 2000, 3000, 3500, or 5000.

In certain embodiments the liposome comprises poly (ethylene glycol)-derivatized diacyl glycerols such as such as 1,2-distearoyl-glyceryl-[methoxy(poly(ethylene glycol)-2000)] 1,2-dimyristoyl-glyceryl-[methoxy(poly(ethylene glycol)-2000)], 1,2-dipalmitoyl-glyceryl-[methoxy(poly (ethylene glycol)-2000)]; or 1,2-dioleoyl-glyceryl-[methoxy (poly(ethylene glycol)-2000)]. In certain embodiments, the molecular weight of PEG is 750, 1000, 1500, 2000, 3000, 3500, or 5000.

In certain embodiments the liposome comprises 1,2-dioctadecyl glycero-N-[methoxy(poly(ethylene glycol)-2000)], dihexadecyl glycero-N-[methoxy(poly(ethylene glycol)-2000)] ditetradecyl glycero-N-[methoxy(poly(ethylene glycol)-2000)]. In certain embodiments, the molecular weight of PEG is 750, 1000, 1500, 2000, 3000, 3500, or 5000.

In certain embodiments the liposome comprises PEG-ceramides, such as N-octdecanoyl-sphingosine-1-{succinoyl[methoxy(poly(ethylene glycol)-2000)]}; N-tetradecanoyl-sphingosine-1-{succinoyl[methoxy(poly(ethylene glycol)-2000)]}; N-hexadecanoyl-sphingosine-1-{succinoyl[methoxy(poly(ethylene glycol)-2000)]}; N-octdecanoyl-sphingosine-1-[methoxy(poly(ethylene glycol)-2000)]; N-tetradecanoyl-sphingosine-1-[methoxy(poly(ethylene glycol)-2000)]; or N-hexadecanoyl-sphingosine-1-[methoxy(poly(ethylene glycol)-2000)]. In certain embodiments the molecular weight of PEG is 750, 1000, 1500, 2000, 3000, 3500, or 5000.

Additional examples of suitable nanoparticle or liposome forming lipids that may be used in the compositions or methods include, but are not limited to, the following: phosphatidylcholines such as diacyl-phosphatidylcholine, dialkylphosphatidylcholine, 1,2-dioleoyl-phosphatidylcholine, 1,2-dipalmitoyl-phosphatidylcholine, 1,2-dimyristoyl-phosphatidylcholine, 1,2-distearoyl-phosphatidylcholine, 1-oleoyl-2-palmitoyl-phosphatidylcholine, 1-oleoyl-2-stearoyl-phosphatidylcholine, 1-palmitoyl-2-oleoyl-phosphatidylcholine and 1-stearoyl-2-oleoyl-phosphatidylcholine; phos-phatidylethanolamines such as 1, 2-dioleoyl-phosphatidylethanolamine, 1,2-dipalmitoyl-phosphatidylethanolamine, 1,2-dimyristoyl-phosphatidylethanolamine, 1,2-distearoyl-phosphatidylethanolamine, 1-oleoyl-2-palmitoyl-phosphatidylethanolamine, 1-oleoyl-2-stearoyl-phosphatidylethanolamine, 1-palmitoyl-2-oleoyl-phosphatidylethanolamine, 1-stearoyl-2-oleoyl-phosphatidylethanolamine and N-succinyl-dioleoyl-phosphatidylethanolamine; phosphatidylserines such as 1,2-dioleoyl-phosphatidylserine, 1,2-dipalmitoyl-phosphatidylserine, 1,2-dimyristoyl-phosphatidylserine, 1,2-distearoyl-phosphatidylserine, 1-oleoyl-2-palmitoyl-phosphatidylserine, 1-oleoyl-2-stearoyl-phosphatidylserine, 1-palmitoyl-2-oleoyl-phosphatidylserine and 1-stearoyl-2-oleoyl-phosphatidylserine; phosphatidylglycerols such as 1,2-dioleoyl-phosphatidylglycerol, 1,2-dipalmitoyl-phosphatidylglycerol, 1,2-dimyristoyl-phosphatidylglycerol, 1,2-distearoyl-phosphatidylglycerol, 1-oleoyl-2-palmitoyl-phosphatidylglycerol, 1-oleoyl-2-stearoyl-phosphatidylglycerol, 1-palmitoyl-2-oleoyl-phosphatidylglycerol and 1-stearoyl-2-oleoyl-phosphatidylglycerol; pegylated lipids; pegylated phospoholipids such as phophatidylethanolamine-N-[methoxy(polyethyleneglycol)-1000], phophatidylethanolamine-N-[methoxy(polyethyleneglycol)-2000], phophatidylethanolamine-N-[methoxy(polyethylene glycol)-3000], phophatidylethanolamine-N-[methoxy(polyethyleneglycol)-5000]; lyso-phosphatidylcholines, lyso-phosphatidylethanolamines, lyso-phosphatidylglycerols, lyso-phosphatidylserines, ceramides; sphingolipids, e.g., sphingomyelin; phospholipids; glycolipids such as ganglioside GMI; glucolipids; sulphatides; phosphatidic acid, such as di-palmitoyl-glycerophosphatidic acid; palmitic fatty acids; stearic fatty acids; arachidonic fatty acids; lauric fatty acids; myristic fatty acids; lauroleic fatty acids; physeteric fatty acids; myristoleic fatty acids; palmitoleic fatty acids; petroselinic fatty acids; oleic fatty acids; isolauric fatty acids; isomyristic fatty acids; isostearic fatty acids; sterol and sterol derivatives such as cholesterol, cholesterol hemisuccinate, cholesterol sulphate, and cholesteryl-(4-trimethylammonio)-butanoate, ergosterol, lanosterol; poly-oxyethylene fatty acids esters and polyoxyethylene fatty acids alcohols; poly-oxyethylene fatty acids alcohol ethers; polyoxyethylated sorbitan fatty acid esters, glycerol polyethylene glycol oxy-stearate; glycerol polyethylene glycol ricinoleate; ethoxylated soybean sterols; ethoxylated castor oil; polyoxyethylene polyoxypropyl-ene fatty acid polymers; polyoxyethylene fatty acid stearates; di-oleoyl-sn-glycerol; dipalmitoyl-succinyl glycerol; 1,3-dipalmitoyl-2-succinylglycerol; 1-alkyl-2-acyl-phosphatidylcholines such as i-hexadecyl-2-palmitoyl-phosphatidylcholine; 1-alkyl-2-acyl-phosphatidylethanolamines such as 1-hexadecyl-2-palmitoyl-phosphatidylethanolamine; 1-alkyl-2-acyl-phosphatidylserines such as 1-hexadecyl-2-palmitoyl-phosphatidylserine; 1-alkyl-2-acyl-phosphatidylglycerols such as 1-hexadecyl-2-palmitoyl-phosphatidylglycerol; 1-alkyl-2-alkyl-phosphatidylcholines such as 1-hexadecyl-2-hexadecyl-phosphatidylcholine; 1-alkyl-2-alkyl-phosphatidylethanolamines such as 1-hexadecyl-2-hexadecyl-phosphatidylethanolamine; 1-alkyl-2-alkyl-phosphatidylserines such as 1-hexadecyl-2-hexadecyl-phosphatidylserine; 1-alkyl-2-alkyl-phosphatidylglycerols such as 1-hexadecyl^-hexadecyl-phosphatidylglycerol; N-Succinyl-dioctadecylamine; palmitoylhomocysteine; lauryltrimethylammonium bromide; cetyltrimethyl-ammonium bromide; myristyltrimethylammonium bromide; N-[1,2,3-dioleoyloxy)-propyl]-N,N,Ntrimethylammoniumchloride (DOTMA); 1,2-dioleoyloxy-3 (trimethyl-ammonium)propane (DOTAP); and 1,2-dioleoyl-c-(4'-trimethylammonium)-butanoyl-sn-glycerol (DOTB).

The liposomes contained in the liposomal imaging agents disclosed herein can be untargeted liposomes or targeted liposomes, e.g., liposomes containing one or more targeting moieties or biodistribution modifiers on the surface of the liposomes. A targeting moiety can be any agent that is capable of specifically binding or interacting with a desired target. In one embodiment, a targeting moiety is a ligand. The ligand, according to the present invention, preferentially binds to and/or internalizes into, a cell in which the liposome-entrapped entity exerts its desired effect (a target cell). A ligand is usually a member of a binding pair where the second member is present on, or in, a target cell(s) or in a tissue comprising the target cell. Examples of ligands suitable for the present invention are: folic acid, protein, e.g., transferrin, a growth factor, an enzyme, a peptide, a receptor, an antibody or antibody fragment (such as, e.g., Fab', Fv, single chain Fv, single-domain antibody), or any other polypeptide comprising antigen-binding sequences (CDRs) of an antibody molecule. A ligand-targeted liposome wherein a targeting moiety is an antibody or a target antigen-binding fragment thereof is called an immunoliposome. In a preferred embodiment, the liposome carrying a targeting moiety, e.g., a ligand, is internalized by a target cell. In yet another embodiment, a targeting moiety is a ligand that specifically interacts with a tyrosine kinase receptor such as, for example, EGFR, HER2, HER3, HER4, PDGFR, VEGFR, FGFR or IGFR receptors. In still another embodiment, the targeting moiety specifically interacts with a growth factor receptor, an angiogenic factor receptor, a transferrin receptor, a cell adhesion molecule, or a vitamin receptor.

In certain embodiments, the liposomes of the liposomal imaging agents exhibit a transmembrane gradient formed by a gradient-forming agent such as a substituted ammonium compound. Alternate loading modalities are described, e.g., in U.S. Pat. No. 8,147,867. Preferably, the higher concentration of the gradient forming agent is in the interior (inner) space of the liposomes. In addition, a liposome composition disclosed herein can include one or more trans-membrane gradients in addition to the gradient created by the substituted ammonium and/or polyanion disclosed herein. For example, liposomes contained in liposome compositions disclosed herein can additionally include a transmembrane pH gradient, ion gradient, electro-chemical potential gradient, and/or solubility gradient.

It will be appreciated that when a trapping agent is used, excess gradient forming agent can be removed from the liposomes (e.g., by diafiltration) after the metal chelator moiety has been entrapped within the liposome.

Metal Chelator

The metal chelating moiety of the liposomal imaging agent can be any agent capable of stably chelating a divalent metal cation and being retained in the interior of the liposome. Examples of such metal chelating moieties include the compound:

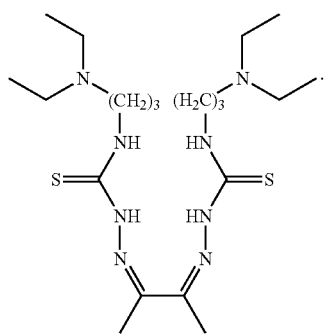

(I)

Additional examples of suitable chelators include compounds represented by Formula (IV):

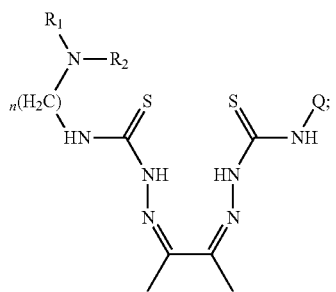

(IV)

in which

Q is H, substituted or unsubstituted $C_1$-$C_6$alkyl or —$(CH_2)_n$—$NR_3R_4$;

$R_1$, $R_2$, $R_3$ and $R_4$ are each independently selected from H, substituted or unsubstituted $C_1$-$C_6$alkyl, or substituted or unsubstituted aryl or wherein either or both of (1) $R_1$ and $R_2$ and (2) $R_3$ and $R_4$ are joined to form a heterocyclic ring;

M is a metal ion, and n is independently, for each occurrence, an integer from 1 to 5.

Divalent Metal Cation

In some embodiments the metal ion is a divalent metal cation. The metal cation for use in the liposomal imaging agents disclosed herein can be any suitable divalent metal cation, e.g., of the alkaline earth, transition metal, lanthanide, or actinide series. A divalent metal cation can be selected according to the intended use of the liposomal imaging agent.

For example, for use in positron emission tomography (PET scanning), a positron-emitting radioisotope (such as a divalent ion of $^{44}Sc^{2+}$, $^{64}Cu^{2+}$, $^{110}In^{2+}$ or $^{128}Cs^{2+}$) can be employed. In certain embodiments, the divalent metal cation is $^{64}Cu^{2+}$.

Alternatively, the divalent metal cation can be a metal cation capable of providing contrast when deposited within a cell or organ (e.g., $Au^{2+}$ or $Ag^{2+}$).

Preparation of Liposomal Imaging Agents

Gradient-based drug loading technologies, in which electrochemical gradients drive the accumulation of drugs in the liposome interior, can be used to prepare liposomes according to the present invention. Thus, a liposome having an electrochemical gradient between the interior and the exterior of the lipid bilayer can be loaded with cationic chelation complexes of divalent metals by addition of the cationic chelator complex to the liposome preparation.

Thus, a transmembrane gradient system can comprise a polymeric anionic trapping agent (such as polyphosphate) or a nonpolymeric anionic trapping agent (sucrose octasulfate). The use of polymeric polyanions such as heparin or dextran sulfate to improve liposomal drug retention has also been reported. However, polyanionic polymers such as heparin and dextran sulfate have notable anticoagulant activity and, thus, heparin and dextran sulfate are less preferred. In many instances, sucrose octasulfate provides better retention of a cationic moiety than polyanionic polymers, resulting in good encapsulation stability. Sucrose octasulfate is a known pharmaceutical ingredient, e.g., of the basic aluminum salt (sucralfate). Advantageously, sucrose octasulfate is chemically well defined, does not have known anticoagulant or anti-macrophage activity, and its salts can be produced in pure crystalline form.

In general, liposomes can be prepared according to any method known in the art. Methods of making and loading liposomes are known in the art. For example, U.S. Pat. No. 4,192,869, describes a method for creating synthetic lipid vesicles loaded with inositol hexaphosphate (IHP). Other methods for producing nanoparticles/liposomes are known to one of skill in the art (see, e.g., U.S. Patent Application Nos. 20030118636; 20080318325; and 20090186074 and U.S. Pat. Nos. 4,192,869; 4,397,846; 4,394,448; 4,394,149; 4,241,046; 4,598,051; 4,429,008; 4,755,388; 4,911,928; 6,426,086; 6,803,053; and 7,871,620.

Alternatively, a liposome can be loaded with a chelator moiety (i.e., without a metal cation complexed to the chelator moiety), followed by addition of the divalent metal cation to the liposomal formulation. In one embodiment, the intraliposomal pH is adjusted so that $^{64}Cu$ enters the lipid bilayer and forms a complex with the chelator inside the liposome.

Diagnostics

The present invention provides methods of patient stratification or determination of the suitability of a patient for a candidate liposome-based therapy. The invention also provides a method of determining whether a patient is a candidate for therapy with a liposomal therapeutic agent, the method comprising:

(a) injecting the patient with a liposomal imaging agent;

(b) imaging the patient to determine the distribution of the liposomal imaging agent within the body of the patient; and (c) determining that the patient is a candidate for therapy with the liposomal therapeutic agent if the liposomal imaging agent is distributed to a location within the body of the patient in need of the liposomal therapeutic agent.

In another aspect, the invention provides a method of monitoring treatment of a location within the patient by a liposomal therapeutic agent, the method comprising:

(a) injecting the patient with a liposomal imaging agent liposomal imaging agent; and (b) imaging the patient, wherein a treatment that reduces or eliminates distribution of the liposomal imaging agent to the location within the patient is identified as effective.

In general, the liposomal imaging agents disclosed herein may be used to image a variety of neoplasias including, but not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, lymphoma, oligodenroglioma, schwannoma, meningioma, melanoma, neuroblastoma, and retinoblastoma.

In another embodiment, liposomal imaging agents may be used to image vascular damage caused by a variety of infectious agents including, but not limited to, bacteria, fungi, and viruses. Likewise, the liposomal imaging agents may be used to monitor a patient during treatment for vascular disorders such as hand-foot syndrome (also known as palmar-plantar erythrodysesthesia (PPE), plantar palmar toxicity, palmoplantar keratoderma, and cutaneous toxicity), which is a side effect of some chemotherapy drugs. Hand-foot syndrome results when a small amount of an anti-neoplastic agent leaks out of the smallest blood vessels in the palms of the hands and soles of the feet. The amount of drug in the capillaries of the hands and feet increases due to the friction and subsequent heat that is generated in those extremities. As a result, more drug may leak out of capillaries in these areas. Once out of the blood vessels, the chemotherapy drug damages surrounding tissues. Liposomal imaging agents may be used to image such damage and treatment of the patient can be adjusted accordingly, either by adjusting the dose of drug or by increasing adjunctive therapies such as administration of anti-inflammatory therapeutics. Liposomal imaging agents may also be used to predict those patients who are most likely to experience such side effects and prophylactic adjunctive therapies may be employed.

The quantity of liposome composition necessary to image a target cell or tissue can be determined by routine in vitro and in vivo methods. Safety testing of such compositions will be analogous to those methods common in the art of drug testing. Typically the dosages for a liposome composition disclosed herein ranges between about 0.0007 and about 10 mg of the liposomes per kilogram of body weight. In an exemplary embodiment, the dosage is about 0.0007 mg of the liposomes per kilogram of body weight.

Typically, the liposome pharmaceutical composition disclosed herein is prepared as a topical or an injectable, either as a liquid solution or suspension. However, solid forms suitable for solution in, or suspension in, liquid vehicles prior to injection can also be prepared.

The liposome composition disclosed herein can be administered in any way which is medically acceptable which may depend on the neoplasia being imaged. Possible administration routes include injections, by parenteral routes such as intramuscular, subcutaneous, intravenous, intraarterial, intraperitoneal, intraarticular, intraepidural, intrathecal, or others, as well as oral, nasal, ophthalmic, rectal, vaginal, topical, or pulmonary, e.g., by inhalation. The compositions may also be directly applied to tissue surfaces.

Kits

The present invention provides kits for use in the diagnostic methods described herein.

In one aspect, the invention provides a kit for determining whether a patient is a candidate for therapy with a liposomal therapeutic agent, the kit comprising:

(a) a container comprising a divalent metal chelating moiety;

(b) a preparation of liposomes in a pharmaceutically acceptable medium, said liposomes having an interior space and a membrane separating said interior from said medium, said interior space comprising a solution having an electro-chemical gradient relative to the pharmaceutically acceptable medium; and (c) instructions for
(i) combining the divalent metal chelating moiety with a divalent metal to form a solution of a divalent metal complexed with a divalent metal chelating moiety;
(ii) combining the solution of the divalent metal complexed with a divalent metal chelating moiety with the preparation of liposomes, under conditions such that a liposomal imaging agent is prepared; and
(iii) administering the liposomal imaging agent to the patient for determining whether the patient is a candidate for therapy with the liposomal therapeutic agent.

In general, the kits are provided so that a technician can prepare a liposomal imaging agent on site before administration to a patient. Thus, the kits will generally include at least a container comprising divalent metal chelating moiety (which can be solution of the divalent metal chelating moiety); a preparation of liposomes in a pharmaceutically acceptable medium; and instructions for combining the divalent metal chelating moiety with a divalent metal to form a solution of a divalent metal complexed with a divalent metal chelating moiety, and combining the solution of the divalent metal complexed with a divalent metal chelating moiety with the preparation of liposomes, under conditions such that a liposomal imaging agent is prepared. If the divalent metal cation is a radioisotope having a short half-life, the kits allow the technician to prepare the liposomal imaging agent immediately before administration of the liposomal imaging agent to the patient. If the divalent metal cation is a stable isotope, then the kit may optionally further include a container comprising the divalent metal cation. Alternatively, if the divalent metal cation is a stable isotope, then the kit may comprise a solution of the divalent metal already complexed with the divalent metal chelating moiety.

The following examples are put forth so as to provide those of ordinary skill in the art with a complete disclosure and description of how to make and use the assay, screening, and therapeutic methods described herein, and are not intended to limit the scope of what the inventors regard as their invention.

EXAMPLES

Example 1: Preparation of diacetyl 4,4'bis (3-(N,N-diethylamino)propyl)thiosemicarbazone (4-DEAP-ATSC)

FIG. 1 shows the chemical structure of diacetyl 4,4'bis (3-(N,N-diethylamino)propyl)thiosemicarbazone (4-DEAP-ATSC), as well as the structure of 4-DEAP-ATSC complexed with $^{64}$Cu. The chelator 4-DEAP-ATSC can be prepared via a two-step synthesis as shown in Scheme 1:

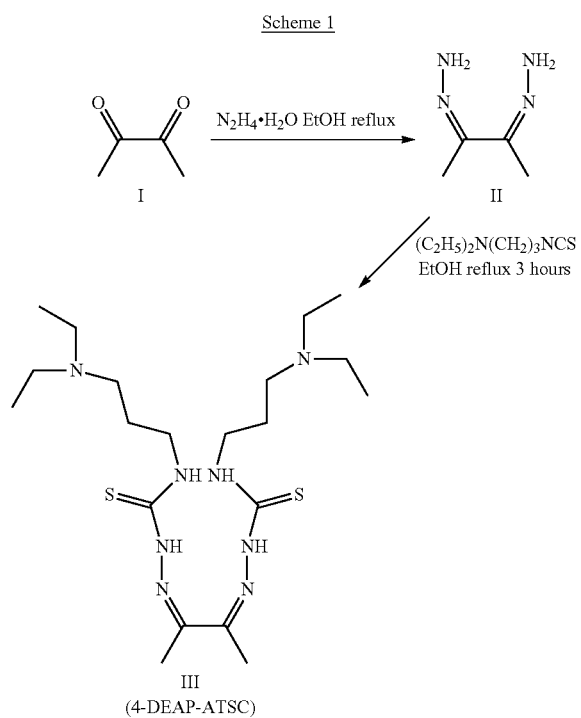

Scheme 1

(4-DEAP-ATSC)

Step 1. Synthesis of Diacetyldihydrazone

The synthesis of diacetyldihydrazone was performed according to the general method described by Busch, D. H. and Bailar, J. C. Jr. (*J. Am. Chem. Soc., v.* 78, p. 1137-1142, 1956).

In a 100-ml round flask with a heating mantle, magnetic stir bar, straight reflux condenser, and a drip funnel attached to the top of the condenser, 60 mL of 200 proof reagent ethanol and 7.7 ml (7.9 g) of hydrazine hydrate (Sigma-Aldrich) were added. The solution was brought to boiling with stirring and reflux, and from the funnel, 5 ml of butane-2,3-dione (diacetyl, I) (Sigma-Aldrich) was added at the rate of about 1 drop in 8 seconds over the course of about 30 minutes, at which point the addition was complete. The reaction mixture was then refluxed for 1 hour, and then 50 ml of distilled water were added. The condenser was changed into distilling position (using a Klaisen-type adapter), and with continuing heating, about 70 ml of the solvent (ethanol) were distilled out at ambient pressure (boiling range 80-95° C.). The residue was briefly placed on a rotary evaporator, and shortly after applying vacuum, the solution crystallized copiously. After 2 hours in the refrigerator (about 4° C.), the crystals were filtered off on a polypropylene frit funnel under suction and air-dried. The yellow product was dissolved in 75 ml of the boiling 200 proof ethanol and allowed to cool down and recrystallized. After an overnight incubation in the refrigerator (about 4° C.), the recrystallized product was filtered off under suction, washed 4 times with 4 ml of cold ethanol, air-dried, and then incubated for 1 hour at 110 µm Hg. This synthesis yielded of 4.27 g (63% based on the diacetyl) of almost colorless crystals of II, with a calculated molecular weight 114.

Step 2. Synthesis of 4,4-bis-(3-diethylamino)propyl)thiocarbazone of diacetyl The synthesis of the 4,4-bis-(3-diethylamino)propyl)thiocarbazone of diacetyl was based on the general procedure for preparing thiosemicarbazones by reaction of diketones with substituted isothiocyanates as described in, for example, French Patent No. 1.528.968, filed May 6, 1967, to Farbwerke Hoechst A.G.

The same reflux-addition assembly as in Step 1 was used. 1.171 g of bis-hydrazone of diacetyl were suspended in 10 ml of 200 proof reagent ethanol, brought to boiling, and more ethanol was added until all solids were dissolved (total 18 ml of ethanol). 3.8 ml (3.6 g) of diethylaminopropyl isothiocyanate (Sigma, 97%) were dissolved in 2.5 ml of ethanol and passed through a layer of Celite® 545 filter aid under suction. The Celite® was rinsed 2 times with 2 ml of ethanol, and the rinses were combined with the isothiocyanate solution. This solution was added drop wise at a rate of approximately 1 drop/second to the boiling solution of diacetyl bis-hydrazone, and the reflux was continued for a total of 2.5 hours. The reflux was then changed to distillation, and about 13 ml of ethanol was distilled out. The remaining reaction mixture was chilled on ice, and the reaction product crystallized from the chilled mixture. After 1 hour in the refrigerator (about 4° C.) the crystalline precipitate was filtered off with suction on the PP porous plate funnel, washed with 2 times with 4 ml of the cold ethanol, and air dried. Yield of the crude product III was 2.05 g as a tan powder.

1.03 g of the crude product III was then mixed with 1.5 ml of 3 N HCl and 3 ml of water. Upon addition of 1 drop of 3 N HCl, the solution was clear, with a pH of about 3 (as determined by paper indicator). The solution was filtered through Whatman® No. 2 paper filter, and concentrated $Na_2CO_3$ was added to raise the pH to about 9.5. The precipitated product was filtered out on a PP funnel, washed 2 times with 2 ml of cold water, briefly air-dried, and the resulting paste was transferred into a 20-ml vial and dissolved in 4 ml of boiling ethanol. Upon chilling, the product crystallized. After 30 minutes on an ice bath, the precipitate was filtered off on the funnel under suction, washed 2 times with 2 ml of cold ethanol, 2 times with 2 ml of anhydrous ether, and dried in vacuum for about 1 hour. This stage of the synthesis yielded 0.701 g, with a calculated molecular weight of 458. Upon addition of a $CuSO_4$ solution to the aqueous solution of III, a yellow-brown color (tea-like) develops, which signifies the formation of the copper complex. Addition of copper sulfate solution to the aqueous solution of II produces a complex having a green color.

Synthesis of ATSM

Figure 2:
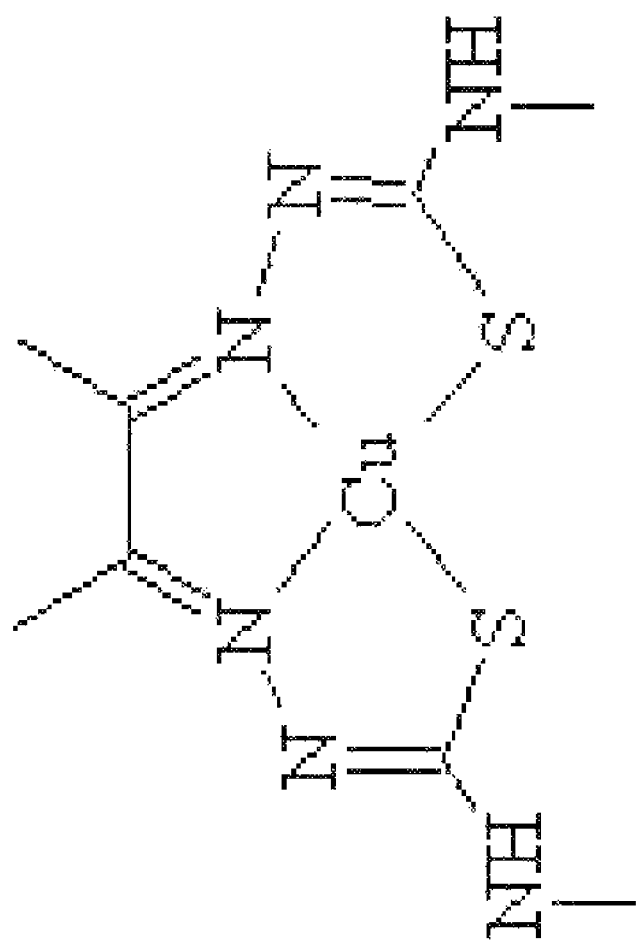
FIG. 2 shows the molecular structure of the ATSM chelator complexed with Cu.

For comparison, diacetyl 4-methylthiosemicarbazone (ATSM) was synthesized essentially as described in Gingras, et al., *Can. J. Chem.*, v. 40, p. 1053-1059, 1962. First, 0.087 ml (86 mg, d=0.990, 1 mMol) of diacetyl were dissolved in 5 ml of ethanol. 0.21 g of 4-methylthiosemicarbazone (Sigma-Aldrich) was then dissolved in 5 ml of water and 0.4 ml glacial acetic acid, and added to the diacetyl solution with stirring at about 40° C. In about 1 minute crystalline precipitate began to form. After stirring for 1 hour at room temperature the reaction mix was placed in the refrigerator (about 4° C.) overnight. The next day the precipitate was filtered off on the PP frit funnel under suction, washed 2 times with 3 ml water, 2 times with 3 ml ethanol, 1 time with 3 ml acetone (it was observed that the precipitate partially dissolved at this stage), and air-dried. After additional drying in 110 µm Hg vacuum for 30 minutes, the yield was 0.1934 g (74% theory) with a molecular weight of 260 (calculated). The structure of ATSM complexed with $^{64}$Cu is shown in FIG. 2.

Example 2: Preparation of a Liposomal Imaging Agent

A liposomal imaging agent was prepared for injection by combining three components (e.g., in the radiopharmacy):
1. $^{64}$Cu, supplied as a radiochemical (e.g., from Washington University);
2. The chelator 4-DEAP-ATSC (e.g., from Albany Molecular Research, Inc. (Albany, N.Y., or prepared as described herein); and
3. Excipient liposomes (i.e., liposomes not containing chelated $^{64}$Cu).

Figure 3:
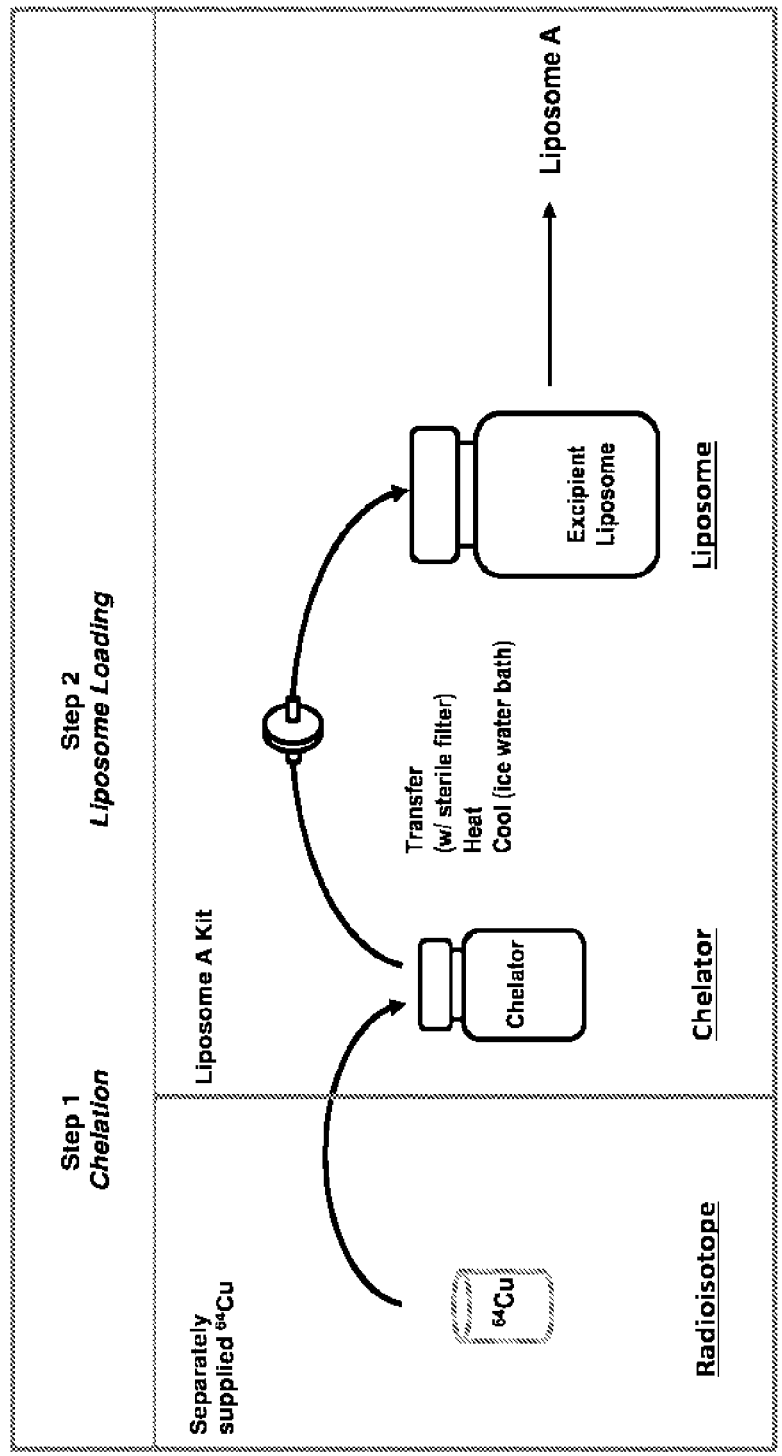
FIG. 3 is a schematic depicting a protocol for preparing labeled liposomes.
Figure 4:
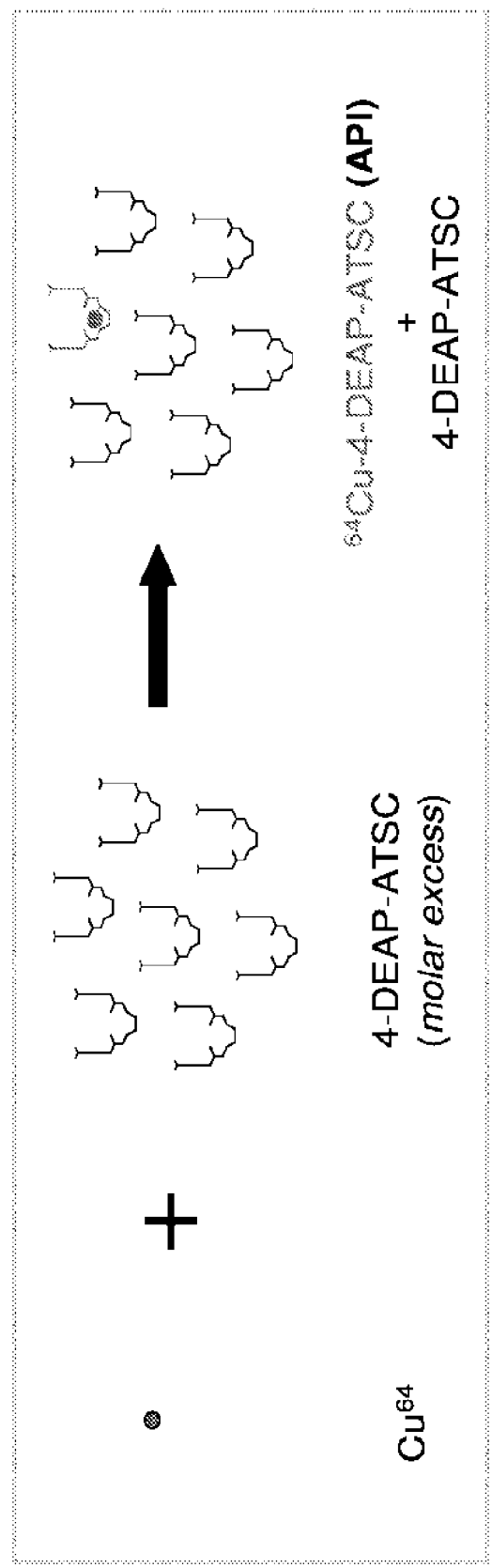
FIG. 4 is a schematic depicting chelation of 4-DEAP-ATSC with a molar excess of $^{64}$Cu.
Figure 5:
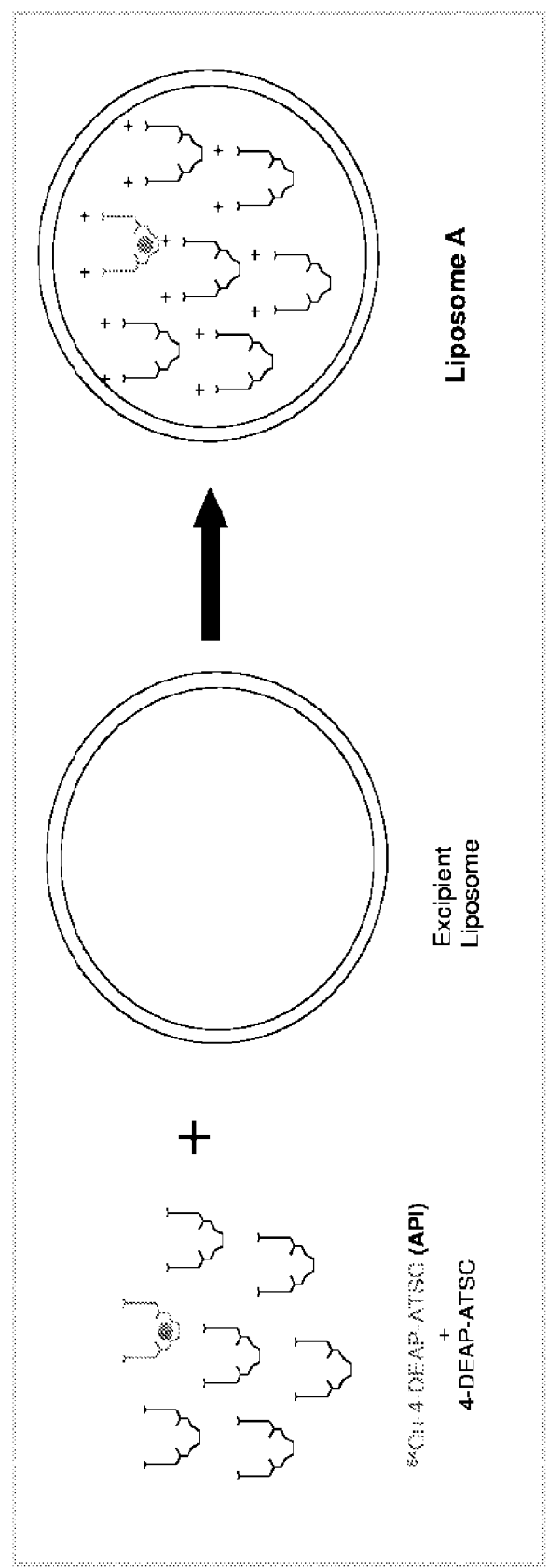
FIG. 5 is a schematic showing the process of liposome loading.

These components were sequentially combined to prepare a liposomal imaging agent for clinical use, according to a two-step procedure (see FIG. 3). In the first step, uncomplexed $^{64}$Cu supplied in 0.1 M HCl as a radiochemical was added to a pH-buffered solution containing the chelating agent, 4-DEAP-ATSC, to prepare complexed $^{64}$Cu:4-DEAP-ATSC. FIG. 1 shows the chemical structures of the uncomplexed and complexed chelating agent. In one embodiment, chelation of $^{64}$Cu to 4-DEAP-ATSC is facilitated by heating the mixture briefly at 65° C. with subsequent cooling in an ice water bath. In another embodiment, chelation of $^{64}$Cu to 4-DEAP-ATSC is performed at room temperature (22-25° C.). FIG. 4 shows the schematic of the reaction in which a molar excess of the chelator is reacted with the $^{64}$Cu. In the second step, the chelated $^{64}$Cu solution is then added through a 0.2 µm filter to PEGylated liposomes prepared with a chemical gradient that enables >90% loading of the $^{64}$Cu:4-DEAP-ATSC into the liposomes to create liposomal imaging agent. FIG. 5 shows a schematic of the liposomal loading depicting complexed and uncomplexed chelator entering the excipient liposomes, which contain an ammonium sulfate pH gradient. As indicated in FIG. 5, the two chelator species become positively charged after they pick up a proton from the ammonium ion and become trapped in the liposome while the free uncharged ammonia is able to exit the liposome.

Preparing 4-DEAP-ATSC Solution for Testing Using Radiometals.

In a 1-dr glass vial with PTFE-lined screw cap, 16.9 mg of 4-DEAP-ATSC (Example 1) was dissolved in 1.85 ml DMSO, and 24 µl of 3 N HCl was added, yielding a solution with a final concentration of 4-DEAP-ATSC of 20 mM. The solution, at first yellow, turned colorless upon addition of the acid. Alternatively, 4-DEAP-ATSC solution can also be prepared in the absence of DMSO for in vivo study purposes. In one example, 10 mg of 4-DEAP-ATSC was dissolved in 1 mL of 0.05 M citric acid (10 mg/mL final concentration of 4-DEAP-ATSC). The concentrated solution can then be diluted into other pH-buffered solutions (e.g., 0.02-0.1M citrate buffer, pH 5-8) at desired concentrations for use.

Validation of Loadability of Cu-III into Gradient-Bearing Liposomes

To test the loadability of Cu-III in gradient-bearing liposomes, the following working solutions were prepared:
1. 20 mM $CuSO_4$ in water; 5.0 mg/ml of $CuSO_4.5H_2O$ in distilled water; 16.7 mg $CuSO_4.5H_2O$ dissolved in 3.34 ml distilled $H_2O$.
2. 20 mM DEAPATSC (III): 9.16 mg/ml DEAPATSC in DMSO+equivalent amount of 3N HCl to titrate the free base of III into dihydrochloride. (Free base solution is yellow, dihydrochloride almost colorless.) 28.2 mg of III dissolved in 3.08 ml DMSO (Aldrich 471267 lot 52596AK), and added 43 µl of 3 N HCl.
3. 20 mM ATSM 5.2 mg/ml in DMSO. 14.8 mg dissolved in 2.84 ml DMSO.
4. 10 mM histidine-100 g/L sucrose buffer, pH 6.5 (HS buffer). In a tared, dry 250-ml volumetric flask, Sucrose (Sigma) 25.03 g (theory, 25 g) and L-Histidine USP (Spectrum Chemicals) 0.3867 g (theory 0.388 g) were added, and then distilled water added, the Sucrose and L-Histidine were dissolved and brought to the 250-ml mark. The volumetric flask was than weighed, and the solution weight was 259.0 g. The calculated density was 1.036, based on the weight of the water being 233.6 g. The solution was transferred into a beaker, and the pH was adjusted to 6.50 with 1 drop of concentrated HCl and 3 drops of 3 N HCl. The solution was filtered using SteriTop®/SteriCup® 250 ml, 0.22 µm, under vacuum.
5. Liposomes: HSPC-Chol-PEG(2000)DSPE (3:1:0.05 molar ratio) liposomes were prepared by extrusion of the ethanol-injected MLVs at 100 mM HSPC in a 10 vol % ethanol/90 vol % 250 mM $(NH_4)_2SO_4$ and 65° C. via 1×200 nm and 6×100 nm stacked PCTE membranes 2 times.

Cu2+ Complexation and Loading into Ammonium-Gradient Liposomes.

Gradient-bearing liposomes were created as follows. A fresh PD-10 column with Sephadex G25M was equilibrated with 2 CV of HS buffer. One ml of HSPC-Chol-PEG(2000) DSPE (3:1:0.05 molar ratio) liposomes (see above) was applied and eluted with HS. The liposome fraction was collected between 3 and 5.5 ml, and adjusted to 7.5 ml with HS, resulting in approximately 12.5 mM phospholipid.

Cu:4-DEAP-ATSC and Cu:ATSM complexes were formed as follows. In 1 mL HS were added 5 µL of 20 mM $CuSO_4$ and 5 µl of 20 mM 4-DEAP-ATSC (in DMSO) or 5 µL of 20 mM ATSM (in DMSO). The ATSM sample became turbid and developed a brown precipitate. The 4-DEAP-ATSC sample developed a yellow-brown color, but remained clear, without any signs of precipitation. The chelator and Cu concentration was 0.1 mM.

2 mM working solution of 4-DEAP-ATSC-Cu was prepared as follows. 0.8 ml of HS, 0.1 mL of 20 mM 4-DEAP-ATSC solution, and 0.1 mL 20 mM $CuSO_4$ solution were mixed, heated for 1 minute at 60° C., and cooled to ambient room temperature. A yellow-brown solution was obtained.

The liposomes were loaded as follows. 0.5 mL of the gradient-bearing liposomes (step 1 above) were mixed with 0.1 ml of 2 mM DEAP-ATSC-Cu chelate and heated in a water bath at 60° C. for 5 minutes, and then chilled on ice. The liposomes were applied on a PD-10 column equilibrated with HS buffer. All visibly detectable color of Cu:DEAP-ATSC complex was eluted in the void volume fraction (between 3 and 4.5 ml). This fraction was collected and saved. These results show that the Cu:DEAP-ATSC was effectively loaded into the ammonium-gradient bearing liposomes.

Chromatography of Cu:4-DEAP-ATSC complex on a PD-10 column (Sephadex G25). 0.1 ml of 2 mM DEAPATS-Cu was diluted with 0.5 mL of HS buffer and chromatographed on a PD-10 column as above. The complex moves as a clearly visible yellow-brown band, and begins to appear in the eluate at about 10 ml (full column bed volume) and eluted in approximately 3.5 ml.

Figure 6:
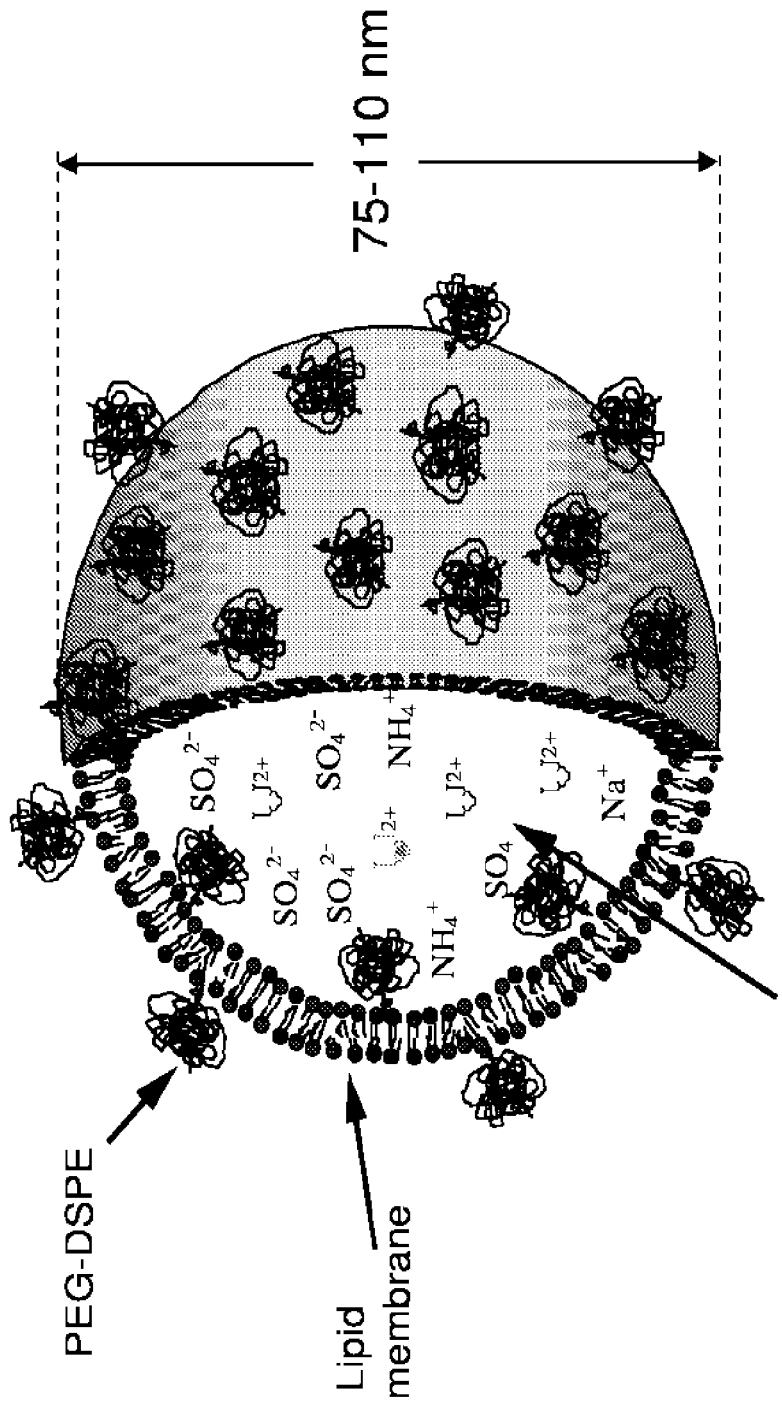
FIG. 6 shows a schematic representation of the structure of Liposome A. $^{64}$Cu:4-DEAP-ATSC chelation complex is in red color. Non-complexed, protonated 4-DEAP-ATSC is depicted as V2$^+$. The internal aqueous space contains $^{64}$Cu:4-DEAP-ATSC, 4-DEAP-ATSC, ammonium sulfate, and sodium sulfate.

When prepared in the radiopharmacy, the liposomal imaging agent is a sterile, injectable parenteral liquid formulation of long-circulating nanoliposomes containing $^{64}$Cu. The unilamellar liposome particles have an average size in the range of 75-100 nm, and consist of a bilayer membrane composed of fully hydrogenated soy phosphatidylcholine (HSPC), cholesterol, and a small amount of poly(ethylene glycol)(Mol. weight 2000)-derivatized distearoylphosphatidylethanolamine (PEG-DSPE). The liposome membrane encloses an interior space where the chelated $^{64}$Cu is contained. A schematic representation of the liposomal imaging agent is shown in FIG. 6. The liposomal imaging agent contains no pharmacologically active pharmaceutical ingredient. In addition to the $^{64}$Cu, it contains 10.2 mg/mL of HSPC, 3.39 mg/ml of cholesterol, 0.18 mg/mL of methoxy-terminated polyethylene glycol (MW2000)-distearoylphosphatidylethanolamine (PEG-DSPE), 10 mM Hepes buffer (pH 6.5), 150 mM sodium chloride to maintain isotonicity, ammonium sulfate in a concentration of less than 0.8 mg/mL, sodium sulfate in a concentration of less than 0.8 mg/mL, and sodium citrate in a concentration of less than 1.5 mg/ml.

Example 3: 4-DEAP-ATSC Chelates $^{64}$Cu and is Loaded into a Liposome

The following data demonstrate the ability of 4-DEAP-ATSC to chelate $^{64}$Cu and to be subsequently loaded into a liposome according to the steps described in FIG. 3.

Under conditions outlined in an exemplary radiopharmacy protocol, 109 nmol of 4-DEAP-ATSC was used to chelate 20 millicuries (mCi) of $^{64}$Cu for 1 minute at 65° C., resulting in a targeted specific radioactivity of approximately 0.2 mCi/nmol. An instant thin layer chromatography (ITLC) assay was used for quantifying the fractions of uncomplexed $^{64}$Cu and $^{64}$Cu(II)-4-DEAP-ATSC complex in the chelation mixture. The uncomplexed $^{64}$Cu can be detected at the solvent front, while the $^{64}$Cu(II)-4-DEAP-ATSC complex remained at the origin where the sample is spotted.

Figure 7:
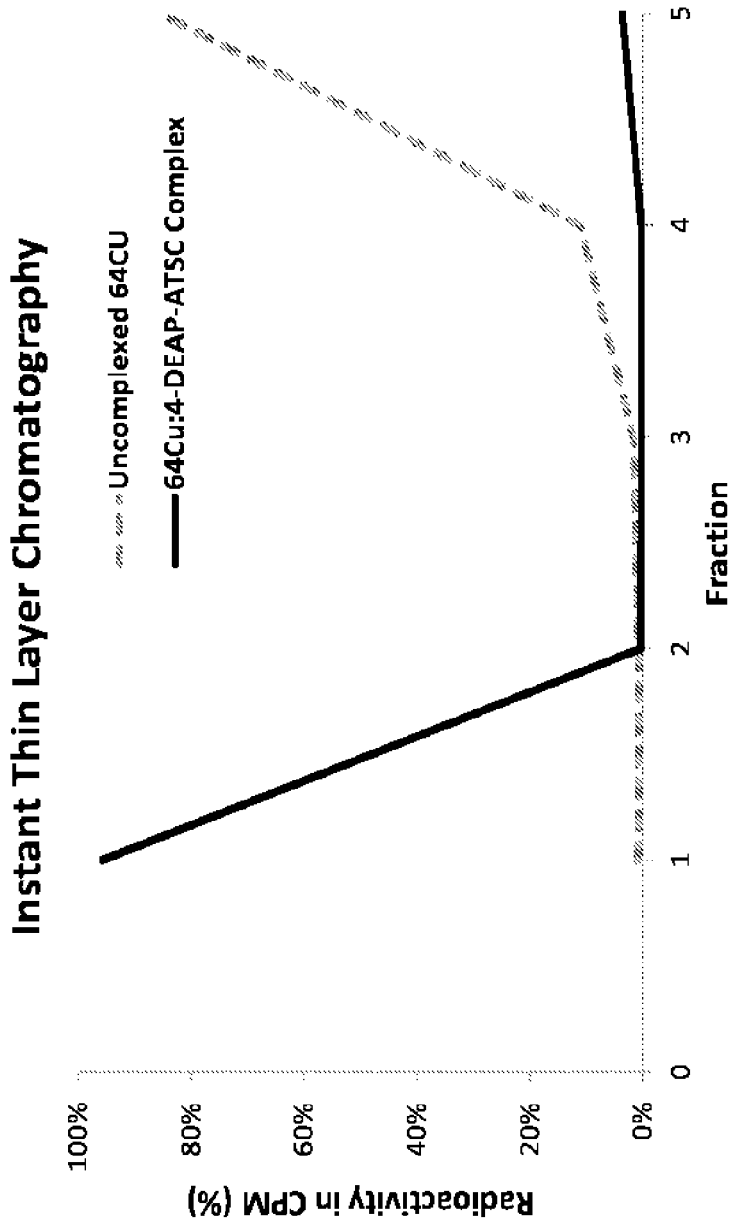
FIG. 7 is a graph showing the $^{64}$Cu chelating efficiency of 4-DEAP-ATSC as assessed by instant thin layer chromatography.

Using the ITLC assay described above (FIG. 7), the efficiency of chelation has been observed to be in the range of 94-99% for preparations of $^{64}$Cu with specific radioactivities ranging from 0.07-0.3 mCi/nmol (see Table 1).

TABLE 1

Chelation Efficiencies of 4-DEAP-ATSC in Step 2 for $^{64}$Cu Preparations.

| Specific Radioactivity (mCi/nmol) | Chelation Efficiency |
| --- | --- |
| 0.01 | 11-46% |
| 0.04 | 98% |
| 0.07 | 68-97% |
| 0.08 | 99% |
| 0.09 | 99% |
| 0.1 | 99-100% |

TABLE 1-continued

Chelation Efficiencies of 4-DEAP-ATSC in Step 2 for $^{64}$Cu Preparations.

| Specific Radioactivity (mCi/nmol) | Chelation Efficiency |
| --- | --- |
| 0.15 | 98-99% |
| 0.17 | 96% |
| 0.18 | 94% |
| 0.2 | 96-99% |
| 0.3 | 98% |
| 0.65 | 99% |
| 13.1 | 99% |

More generally, the key components to prepare the liposomal imaging agent can be combined according to the steps outlined in FIG. 3. Prior to beginning the labeling procedure, the following preparation steps should be followed: Prepare heat bath @ 65° C. and an ice water bath. Add contents of the $^{64}$Cu vial to the chelator vial. Place $^{64}$Cu-chelator vial either in a 65° C. heat bath for 1 min or incubate at room temperature for 1 min. Cool to room temp using ice bath if heated. Transfer the entire contents to the liposome vial, e.g., with a filtration syringe. Place the liposome vial in 65° C. heat bath for 10 min and then cool to room temp with the ice bath. A sample is taken to check loading efficiency.

Example 4: Efficiency of $^{64}$Cu Loading into Liposomes

The efficiency of liposome loading for Step 2 (see FIG. 3) was determined. Liposomes were loaded with $^{64}$Cu:4-DEAP-ATSC over a range of 4-DEAP-ATSC:lipid ratios of 0.013-4.2 mole %. Encapsulated (liposomal) radioactivity was separated from total radioactivity using size exclusion chromatography. From this it was determined that >90% of the $^{64}$Cu was loaded into the liposome at 4-DEAP-ATSC:lipid ratios <2 mol % as shown in Table 2. From these data, the 4-DEAP-ATSC to lipid ratio was chosen to be 0.07 mol %.

TABLE 2

Efficiency of $^{64}$Cu Loading into Liposomes as a Function of Varying Chelator to Lipid Ratios.

| 4-DEAP-ATSC:Lipid Ratio (mol %) | $^{64}$Cu Loading Efficiency |
| --- | --- |
| 0.01% | 96-98% |
| 0.04% | 96-98% |
| 0.10% | 95-97% |
| 0.15% | 92-97% |
| 0.25% | 92-97% |
| 0.40% | 94-98% |
| 0.50% | 92-96% |
| 0.67% | 96% |
| 0.75% | 92% |
| 1% | 93-98% |
| 2% | 91-97% |
| 4.20% | 86% |
| 5.00% | 92-93% |
| 10% | 82-92% |
| 25% | 90% |
| 50% | 71% |

In an exemplary embodiment, $^{64}$Cu meets the specifications shown in Table 3.

TABLE 3

$^{64}$Cu radioisotope purity

| Identity | Purity |
|---|---|
| $^{55}$Co | <0.176% |
| $^{60}$Cu | n/a |
| $^{61}$Co | <6.600% |
| $^{61}$Cu | <0.550% |

Radionuclide purity is assessed by the measurement of $^{40}$K, $^{55}$Co, $^{56}$Co, $^{57}$Co, $^{58}$Co, $^{60}$Co, and $^{67}$Ga, as indicated on their Certificates of Analysis. $^{64}$Cu in 0.1 M HCl is provided in a plastic vial with volumes 20 to 100 μL and specific activity of 50-400 mCi/μg.

Example 5: Lipid Components

Figure 8:
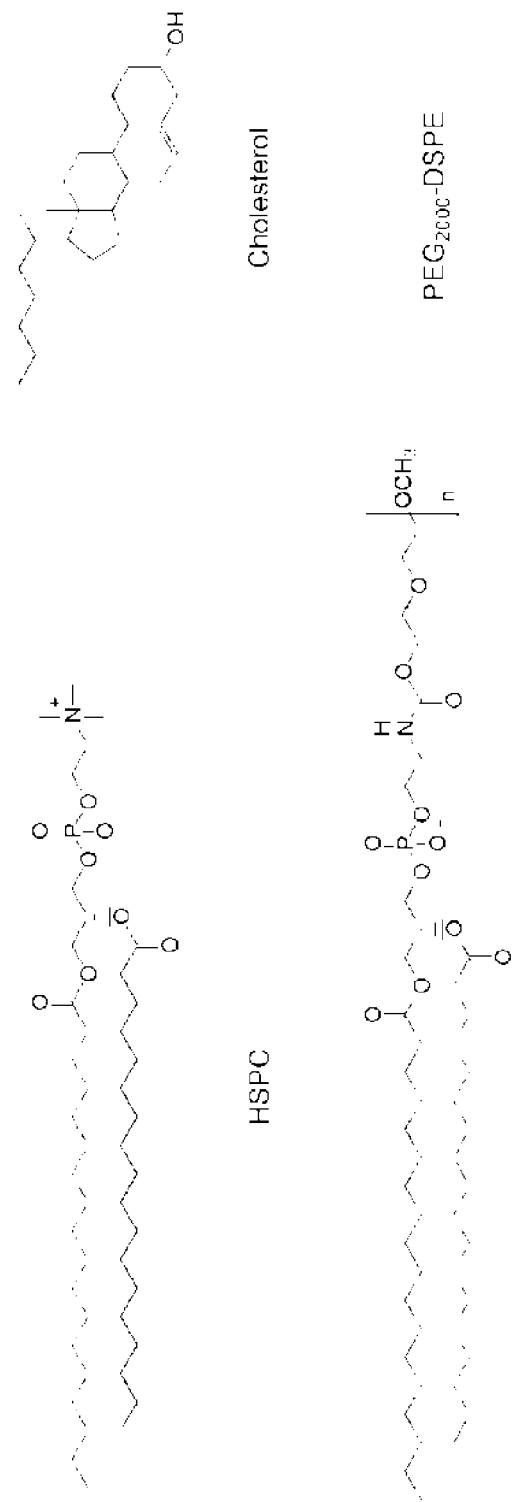
FIG. 8 depicts the chemical structures of exemplary lipid components of a liposome.

The liposomes described herein can be formed using a variety of lipid components. The structures of representative lipids are shown FIG. 8. The selection of lipids is not meant to be limiting.

Table 4 shows the composition of the liposomal excipients and the composition of the excipient liposomes for the 10 mL solution in the final container (Excipient Liposome in FIG. 3).

TABLE 4

Qualitative and Quantitative Composition of the Liposomal Excipients

| Component | Concentration, mg/mL | Concentration, mg/vial (10 mL) |
|---|---|---|
| HSPC | 10.2 | 102 |
| Cholesterol | 3.4 | 34 |
| PEG-DSPE | 0.18 | 1.8 |
| Sodium chloride | 8.77 | 87.7 |
| Hepes | 2.38 | 23.8 |
| Ammonium sulfate | <0.8 | <8 |
| Sodium sulfate | <0.8 | <8 |
| Sodium Hydroxide | For pH adjustment | For pH adjustment |
| Water for Injection | QS to 1.0 mL | QS to 10.0 mL |

Table 5 shows the functions of the components in the liposomal excipient.

TABLE 5

Functions of the Components in the liposomal excipient

| Component | Function |
|---|---|
| HSPC | Lipid |
| Cholesterol | Lipid |
| PEG-DSPE | Lipid |
| Hepes | Buffer |
| Sodium Chloride | Isotonicity |
| Ethanol* | Solvent for lipids |
| Ammonium sulfate** | drug loading and trapping agent |
| Sodium sulfate** | osmolarity adjusting agent |
| NaOH, HCl | pH adjustment |

*removed by diafiltration
**extraliposomal ammonium sulfate and sodium sulfate removed during diafiltration Other excipient liposome formulations comprised of different lipid components and loading gradients have been prepared for loading of $^{64}$Cu:4-DEAP-ATSC. The liposome compositions and loading efficiencies of samples stored at 4° C. (Table 6) and at 4° C., 30° C., and 37° C. (Table 7) are listed below:

TABLE 6

Liposome compositions and loading efficiencies

| Sample | Lipid Composition | External pH | Loading Gradient | Loading Efficiency (samples stored at 4° C.) (%) |
|---|---|---|---|---|
| D1 | DSPC:Cholesterol:PEG-DSPE (3:1:1 wt ratio) | 6.5 | 50 mM Ammonium Sulfate + 50 mM Sodium Sulfate | 96% |
| D2 | DSPC:Cholesterol:PEG-DSPE (3:1:1 wt ratio) | 6.5 | 125 mM Ammonium Sulfate | 97% |
| D3 | DSPC:Cholesterol:PEG-DSPE (3:1:1 wt ratio) | 6.5 | 250 mM Ammonium Sulfate | 97% |
| D4 | DSPC:Cholesterol:PEG-DSPE (3:1:1 wt ratio) | 7.2 | 0.142N Triethylammonium Sucrose Octasulfate | 96% |
| D5 | DSPC:Cholesterol:PEG-DSPE (3:1:1 wt ratio) | 7.2 | 0.215N Triethylammonium Sucrose Octasulfate | 96% |
| D5 | DSPC:Cholesterol:PEG-DSPE (3:1:1 wt ratio) | 7.2 | 0.43N Triethylammonium Sucrose Octasulfate | 96% |
| SM1 | Sphingomyelin:Cholesterol:PEG-DSPE (3:1:1 wt ratio) | 6.5 | 50 mM Ammonium Sulfate + 50 mM Sodium Sulfate | 97% |
| SM2 | Sphingomyelin:Cholesterol:PEG-DSPE (3:1:1 wt ratio) | 6.5 | 125 mM Ammonium Sulfate | 97% |
| SM3 | Sphingomyelin:Cholesterol:PEG-DSPE (3:1:1 wt ratio) | 6.5 | 250 mM Ammonium Sulfate | 97% |

TABLE 6-continued

Liposome compositions and loading efficiencies

| Sample | Lipid Composition | External pH | Loading Gradient | Loading Efficiency (samples stored at 4° C.) (%) |
|---|---|---|---|---|
| SM4 | Sphingomyelin:Cholesterol:PEG-DSPE (3:1:1 wt ratio) | 7.4 | 50 mM Ammonium Sulfate + 50 mM Sodium Sulfate | 98% |
| SM5 | Sphingomyelin:Cholesterol:PEG-DSPE (3:1:1 wt ratio) | 7.4 | 125 mM Ammonium Sulfate | 96% |
| SM6 | Sphingomyelin:Cholesterol:PEG-DSPE (3:1:1 wt ratio) | 7.4 | 250 mM Ammonium Sulfate | 97% |
| SM7 | Sphingomyelin:Cholesterol:PEG-DSG (3:1:1 wt ratio) | 6.5 | 50 mM Ammonium Sulfate + 50 mM Sodium Sulfate | 97% |
| SM8 | Sphingomyelin:Cholesterol:PEG-DSG (3:1:1 wt ratio) | 6.5 | 125 mM Ammonium Sulfate | 95% |
| SM9 | Sphingomyelin:Cholesterol:PEG-DSG (3:1:1 wt ratio) | 7.4 | 50 mM Ammonium Sulfate + 50 mM Sodium Sulfate | 96% |
| SM10 | Sphingomyelin:Cholesterol:PEG-DSG (3:1:1 wt ratio) | 7.4 | 125 mM Ammonium Sulfate | 96% |
| SM11 | Sphingomyelin:Cholesterol:PEG-DSGE (3:1:1 wt ratio) | 6.5 | 50 mM Ammonium Sulfate + 50 mM Sodium Sulfate | 96% |
| SM12 | Sphingomyelin:Cholesterol:PEG-DSGE (3:1:1 wt ratio) | 6.5 | 125 mM Ammonium Sulfate | 91% |
| SM13 | Sphingomyelin:Cholesterol:PEG-DSPE (3:1:0.5 wt ratio) [PEG-DSPE Inserted post-extrusion] | 7.4 | 50 mM Ammonium Sulfate + 50 mM Sodium Sulfate | 94% |
| SM14 | Sphingomyelin:Cholesterol:PEG-DSPE (3:1:0.5 wt ratio) [PEG-DSPE Inserted post-extrusion] | 7.4 | 125 mM Ammonium Sulfate | 92% |

TABLE 7

Liposome compositions and loading efficiencies

| Sample | Lipid Composition | External pH | Loading Gradient | 4° C. Storage - Loading Efficiencies | 30° C. Storage - Loading Efficiencies | 37° C. Storage - Loading Efficiencies |
|---|---|---|---|---|---|---|
| D5 | DSPC:Cholesterol:PEG-DSPE (3:1:1 wt ratio) | 7.2 | 0.215N Triethylammonium Sucrose Octasulfate | 96% | 95% | N/A |
| D6 | DSPC:Cholesterol:PEG-DSPE (3:1:1 wt ratio) | 7.2 | 0.43N Triethylammonium Sucrose Octasulfate | 96% | 95% | N/A |
| SM4 | Sphingomyelin:Cholesterol:PEG-DSPE (3:1:1 wt ratio) | 7.4 | 50 mM Ammonium Sulfate + 50 mM Sodium Sulfate | 99% | 98% | 98% |
| SM5 | Sphingomyelin:Cholesterol:PEG-DSPE (3:1:1 wt ratio) | 7.4 | 125 mM Ammonium Sulfate | 97% | 98% | 96% |
| SM6 | Sphingomyelin:Cholesterol:PEG-DSPE (3:1:1 wt ratio) | 7.4 | 250 mM Ammonium Sulfate | 98% | 96% | 97% |
| SM7 | Sphingomyelin:Cholesterol:PEG-DSG (3:1:1 wt ratio) | 6.5 | 50 mM Ammonium Sulfate + 50 mM Sodium Sulfate | 96% | 96% | 97% |

TABLE 7-continued

Liposome compositions and loading efficiencies

| Sample | Lipid Composition | External pH | Loading Gradient | 4° C. Storage - Loading Efficiencies | 30° C. Storage - Loading Efficiencies | 37° C. Storage - Loading Efficiencies |
|---|---|---|---|---|---|---|
| SM8 | Sphingomyelin:Cholesterol:PEG-DSG (3:1:1 wt ratio) | 6.5 | 125 mM Ammonium Sulfate | 96% | 96% | 95% |
| SM9 | Sphingomyelin:Cholesterol:PEG-DSG (3:1:1 wt ratio) | 7.4 | 50 mM Ammonium Sulfate + 50 mM Sodium Sulfate | 96% | 97% | 96% |
| SM10 | Sphingomyelin:Cholesterol:PEG-DSG (3:1:1 wt ratio) | 7.4 | 125 mM Ammonium Sulfate | 97% | 96% | 96% |
| SM11 | Sphingomyelin:Cholesterol:PEG-DSGE (3:1:1 wt ratio) | 6.5 | 50 mM Ammonium Sulfate + 50 mM Sodium Sulfate | 96% | 95% | 96% |
| SM12 | Sphingomyelin:Cholesterol:PEG-DSGE (3:1:1 wt ratio) | 6.5 | 125 mM Ammonium Sulfate | 90% | 91% | 91% |
| SM13 | Sphingomyelin:Cholesterol:PEG-DSPE (3:1:0.5 wt ratio) [PEG-DSPE Inserted post-extrusion] | 7.4 | 50 mM Ammonium Sulfate + 50 mM Sodium Sulfate | 96% | 96% | 94% |
| SM14 | Sphingomyelin:Cholesterol:PEG-DSPE (3:1:0.5 wt ratio) [PEG-DSPE Inserted post-extrusion] | 7.4 | 125 mM Ammonium Sulfate | 96% | 95% | 92% |

Example 6: Use of $^{64}$Cu:4-DEAP-ATSC in Untargeted Liposomal Imaging Agents

As described herein, in one embodiment, the liposomal imaging agent is an untargeted liposome containing entrapped chelator (4-DEAP-ATSC) and a $^{64}$Cu chelation complex ($^{64}$Cu:4-DEAP-ATSC) (herein after, "Liposome A"). 4-DEAP-ATSC is derived from the ATSM structure by adding two diethylamino(propyl) groups (compare structures in FIGS. 1 and 2). $^{64}$Cu-ATSM (see structure in FIG. 2) is currently being clinically tested as a PET imaging agent in cancer patients. 4-DEAP-ATSC is similar to ATSM in that it retains the $^{64}$Cu chelating activity of ATSM; however, it has the unexpected property of being rapidly entrapped within PEGylated liposomes containing a chemical gradient, thereby creating a liposomal imaging agent, as described above.

Example 7: Effect of Liposome Targeting on Tumor Deposition

Figure 25:
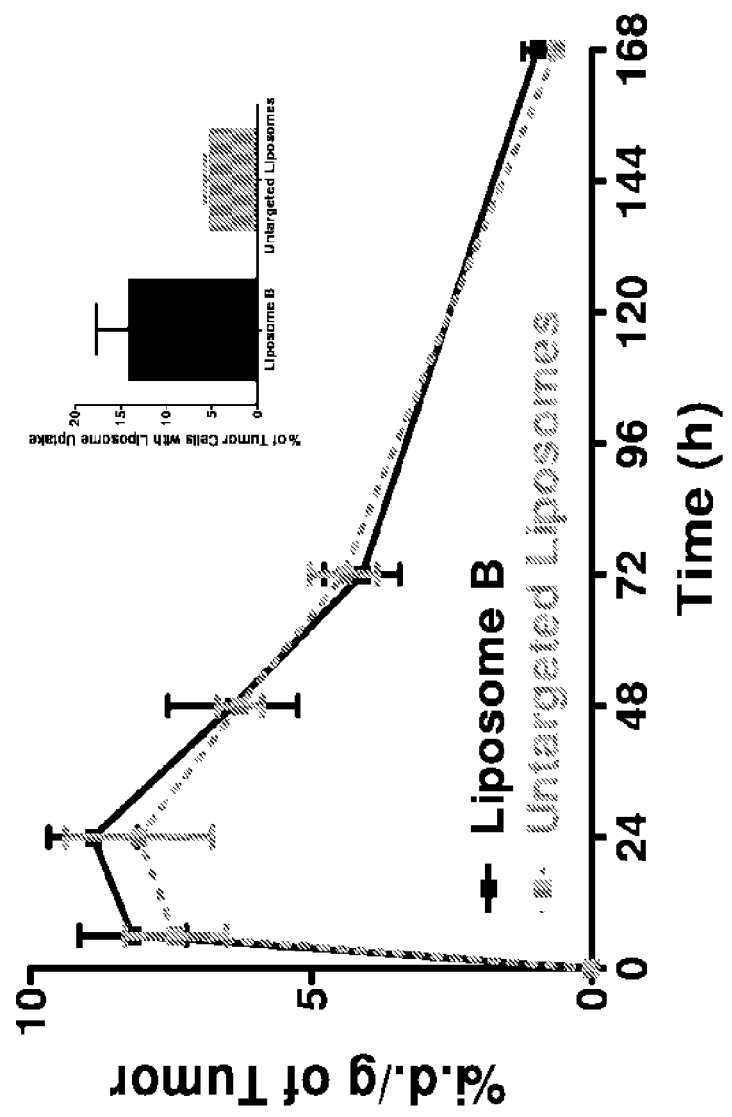
FIG. 25 is a graph showing that liposome targeting has no effect on the total tumor deposition of Liposome B and its untargeted counterpart, but rather, increases the liposome uptake by tumor cells within the tumors (insert).
Figure 26:
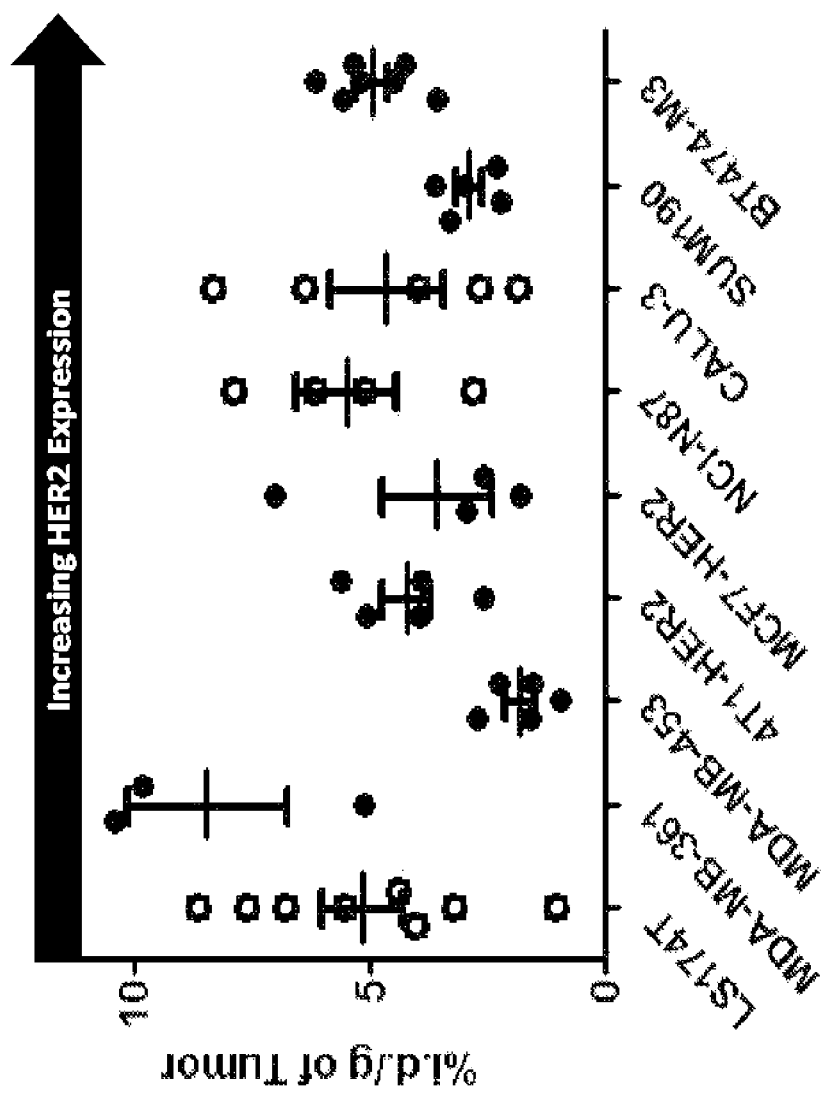
FIG. 26 is a graph showing tumor deposition of Liposome B in mouse xenograft models expressing various levels of HER2. Tumor depositions of Liposome B were found to vary with no correlation with HER2 expression in the tumors.

Preclinical studies have examined the effect of liposome targeting on total tumor deposition. These studies have shown that the targeting of PEGylated liposomes to the HER2 receptor on tumors did not affect its pharmacokinetics or overall tumor deposition compared to an untargeted liposome. Kirpotin et al labeled liposomes with $^{67}$Ga and showed similar tumor deposition % injected dose per gram (% i.d./g) for a HER2-targeted liposome and a corresponding untargeted liposome (*Cancer Research* (66)6732 (2006). Similar results were obtained by comparing tumor deposition by HER2-targeted Liposome B and untargeted liposomes (disclosed in co-pending Patent Application Serial No. PCT/US2011/064496) in an NCI-N87 (ATCC® #CRL-5822™) gastric carcinoma mouse xenograft model, as well as in BT474-M3 breast carcinoma mouse xenograft model in which the two liposome formulations only result in difference in tumor cell uptake (FIG. 25 insert) with no significant difference detected in total liposome deposition in the tumors (FIG. 25). FIG. 26 further illustrates that liposome targeting does not have any obvious effect on tumor deposition as no correlation can be established between tumor depositions of Liposome B in tumors with varying HER2 expression. Similarly, in the BT474-M3 tumor model (HER2-overexpressing tumors), the HER2-targeted liposome B were shown to have similar tumor deposition as the non-targeted liposome A The importance of liposome deposition in dictating total delivery of drug to tumors is also supported by results from kinetic computational modeling. The inventors have developed a physiologically-based pharmacokinetic model of liposome delivery to tumors based on literature data. The model includes liposome and free drug pharmacokinetics, as well as a physiologically-based tumor compartment that captures vascular, interstitial, and cellular spaces.

Figure 9A:
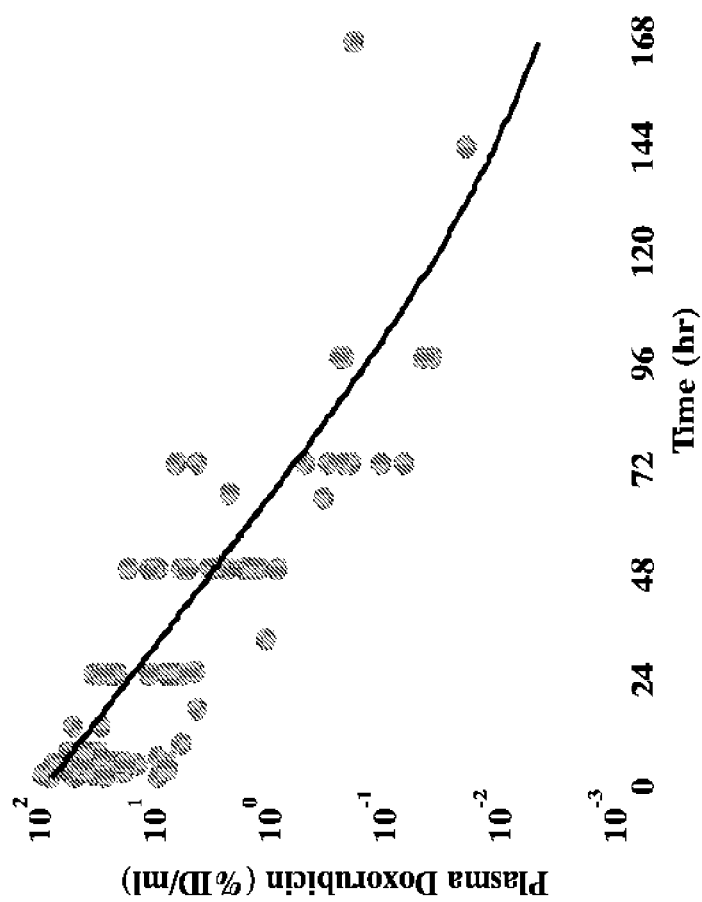
FIG. 9A is a graph of a fitting of model results (plasma doxorubicin) to published pharmacokinetic data for Doxil®.
Figure 9B:
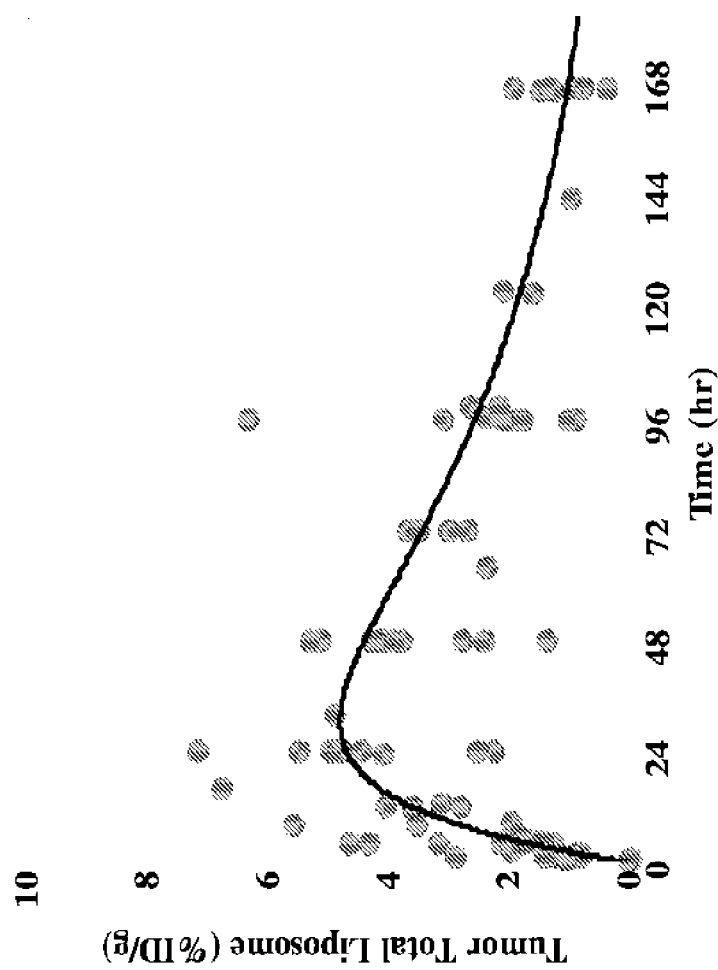
FIG. 9B is a graph of a fitting of model results (tumor total liposome) to published pharmacokinetic data for Doxil®.
Figure 9C:
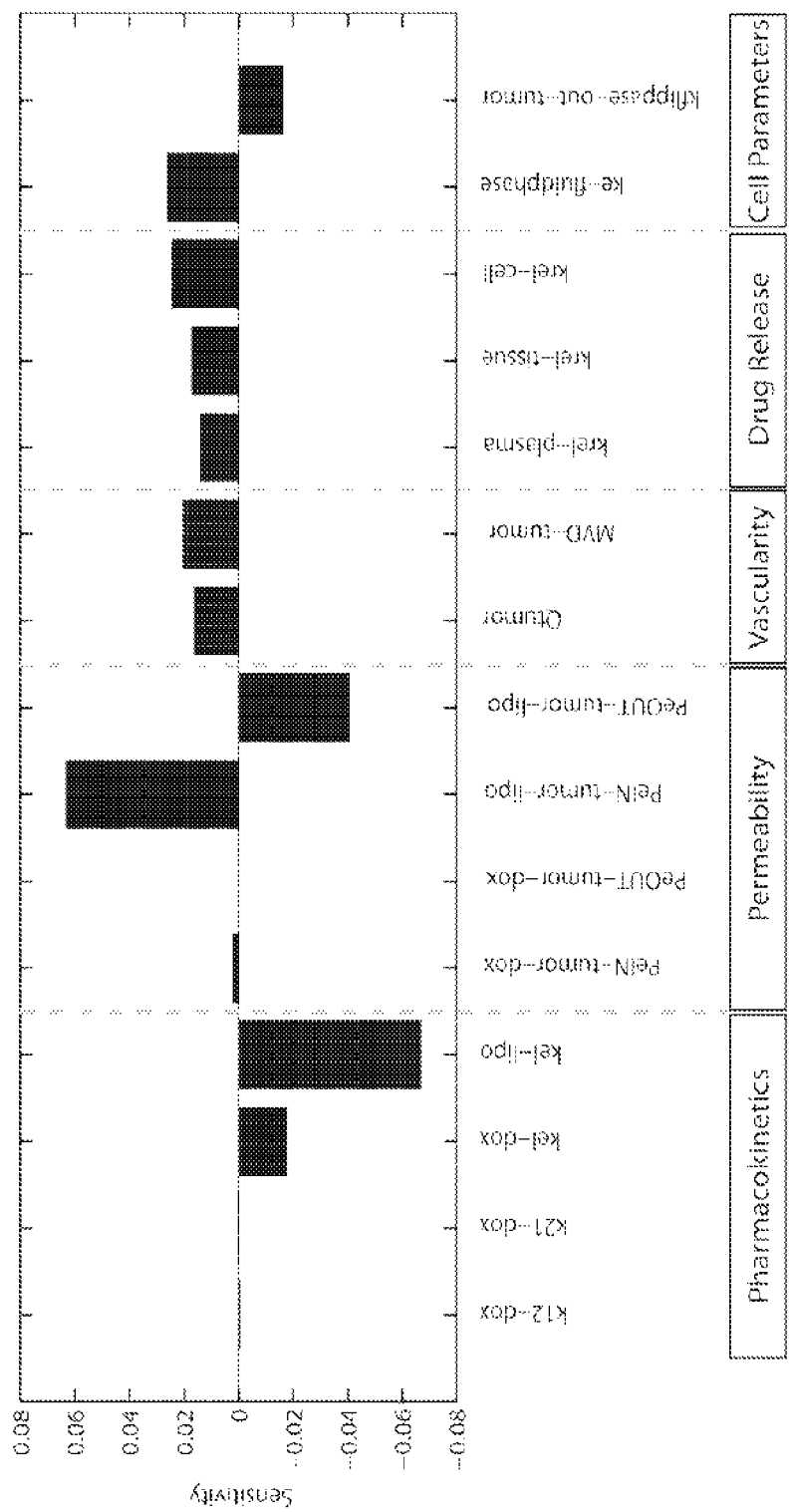
FIG. 9C is a bar chart depicting the fitting of model results to the published pharmacokinetic data for Doxil® and a corresponding sensitivity analysis.

The model was trained on literature data. As shown in FIG. 9, a sensitivity analysis of the model indicated that factors related to liposome deposition such as, e.g., vascular surface area and permeability of vasculature to liposomes, are the most important determinants of total delivery of drug to tumor cells.

Figure 10A:
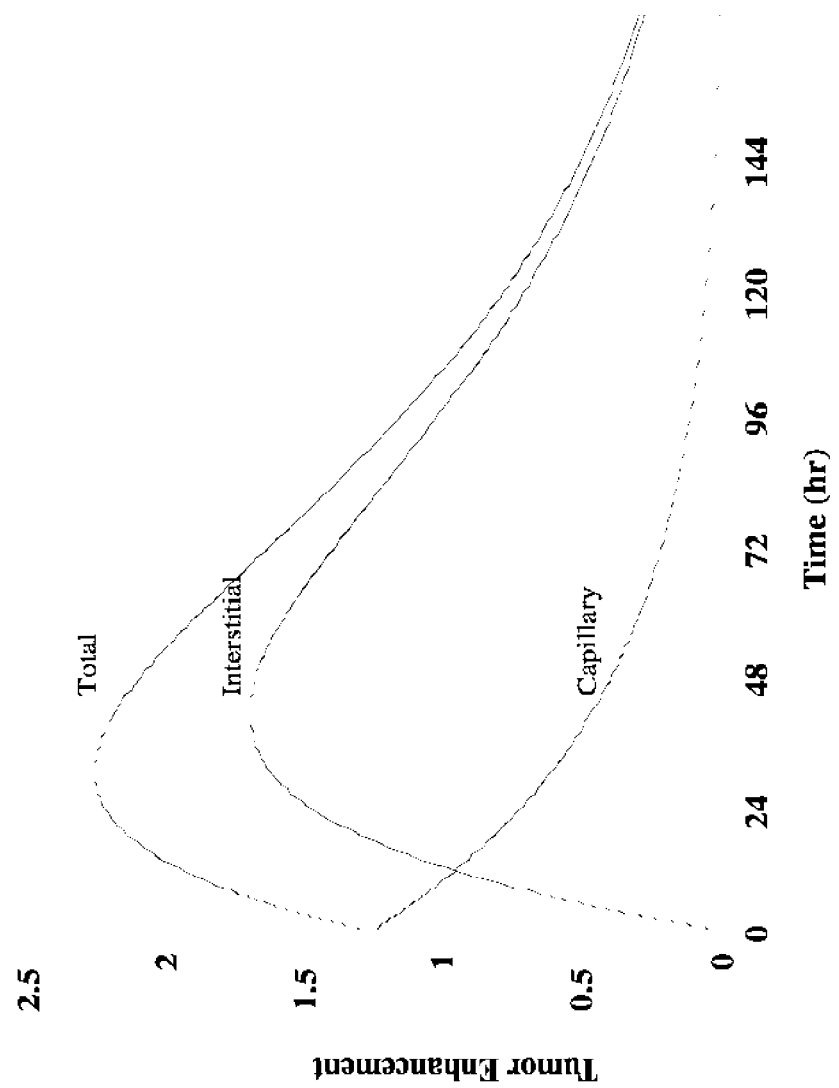
FIG. 10A is a graph depicting Liposome A kinetics (tumor enhancement) of deposition and anticipated variability of deposition based on simulations derived from reported literature data.
Figure 10B:
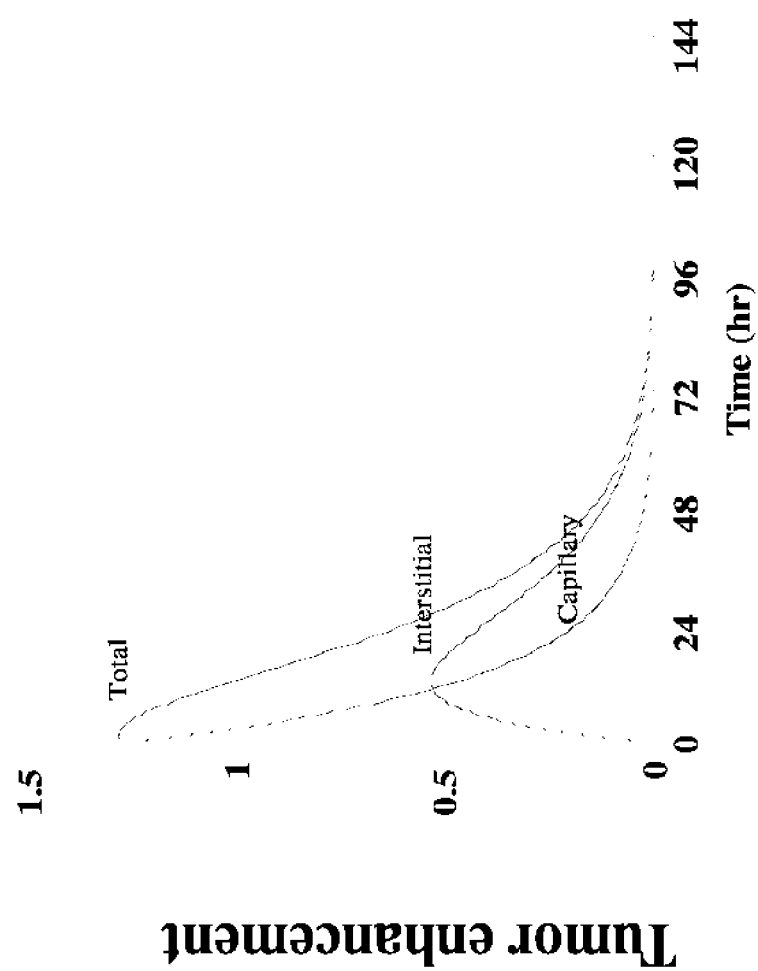
FIG. 10B is a graph depicting Liposome A kinetics (tumor enhancement) of deposition and anticipated variability of deposition based on simulations derived from reported literature data.
Figure 10C:
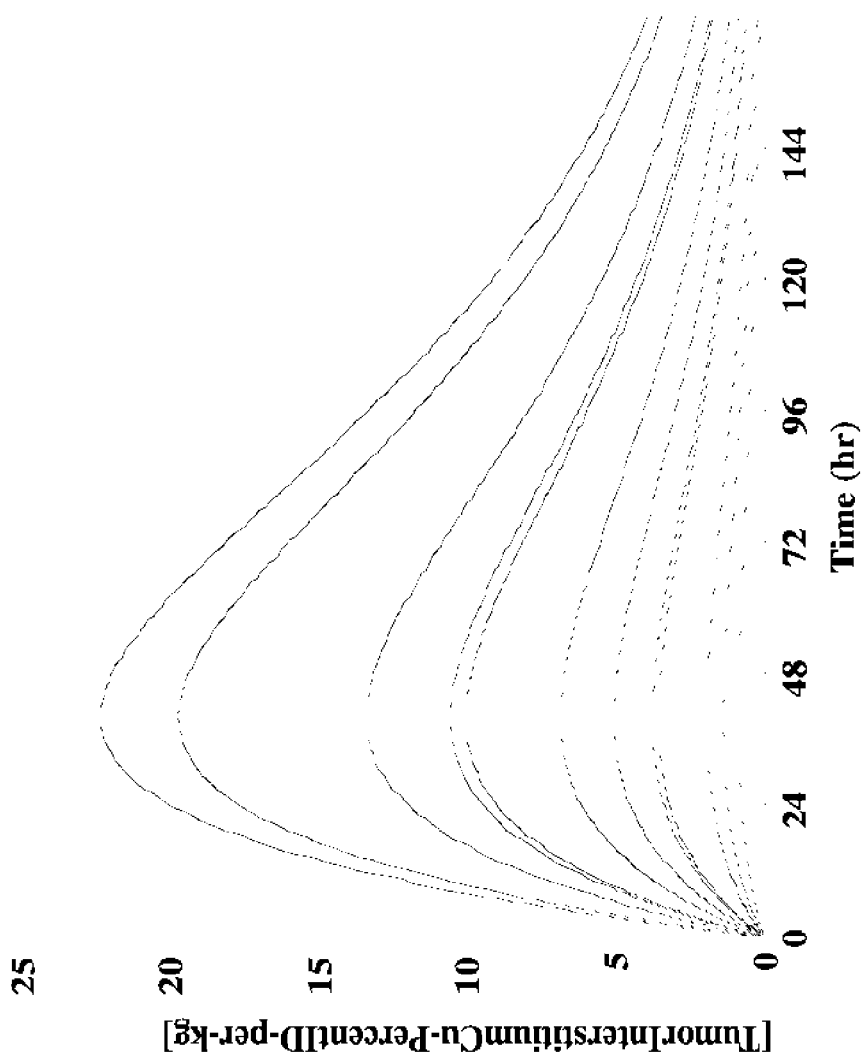
FIG. 10C is a graph depicting Liposome A kinetics (tumor interstitium Cu) of deposition and anticipated variability of deposition based on simulations derived from reported literature data.

This kinetic model was adapted to create a model of Liposome A deposition in tumors. As shown in FIG. 10, the model simulated profiles of Liposome A concentration in plasma, tumor vasculature, and tumor interstitium. This model allowed estimation of the fraction of total tumor signal expected to arise from deposited (interstitial) liposomes vs. liposomes in the tumor vascular space. Further-more, it also allowed simulation of the effect of $^{64}$Cu decay on signal (FIG. 10B), as well as the anticipated variability across patients (FIG. 10C), based on patient data from Harrington, et al., *Clin. Cancer Res.* (2001) February; 7(2): 243-54. Variability in tumor deposition was also observed across multiple preclinical xenograft models with Liposome B (FIG. 26), as well as other $^{64}$Cu-loaded liposomes.

Figure 11:
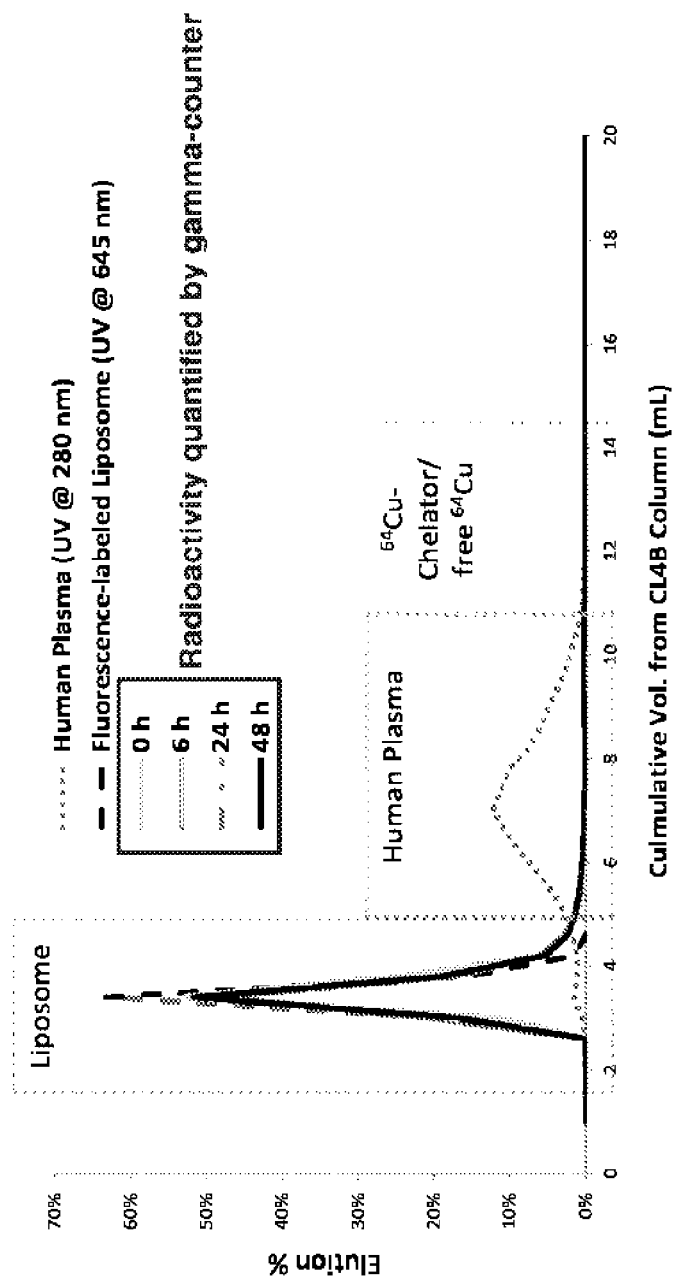
FIG. 11 is a graph depicting the stability of Liposome A in human plasma after 48 hours.

Example 8: In Vitro Stability of $^{64}$Cu:4-DEAP-ATSC-Loaded Liposome (Liposome A) in Human Plasma $^{64}$Cu was shown to be effectively retained in the liposome after incubation of $^{64}$Cu:4-DEAP-ATSC-loaded liposome (Liposome A) in human plasma for 48 hours (FIG. 11). The in vitro stability of Liposome A was examined by incubating the $^{64}$Cu:4-DEAP-ATSC-loaded liposome with human plasma at 37° C. At the designated incubation time (up to 48 hours), encapsulated (liposomal) radioactivity was separated from released/unencapsulated radioactivity using size exclusion chromatography (CL4B column which allows for separating liposomal, protein, and $^{64}$Cu:4-DEAP-ATSC/uncomplexed $^{64}$Cu fractions). The data show that Liposome A is highly stable in human plasma at physiological temperature, with <5% of unencapsulated $^{64}$Cu detected up to 48 hours.

Example 9: In Vivo Imaging of $^{64}$Cu-Loaded Liposome B

Figure 12:
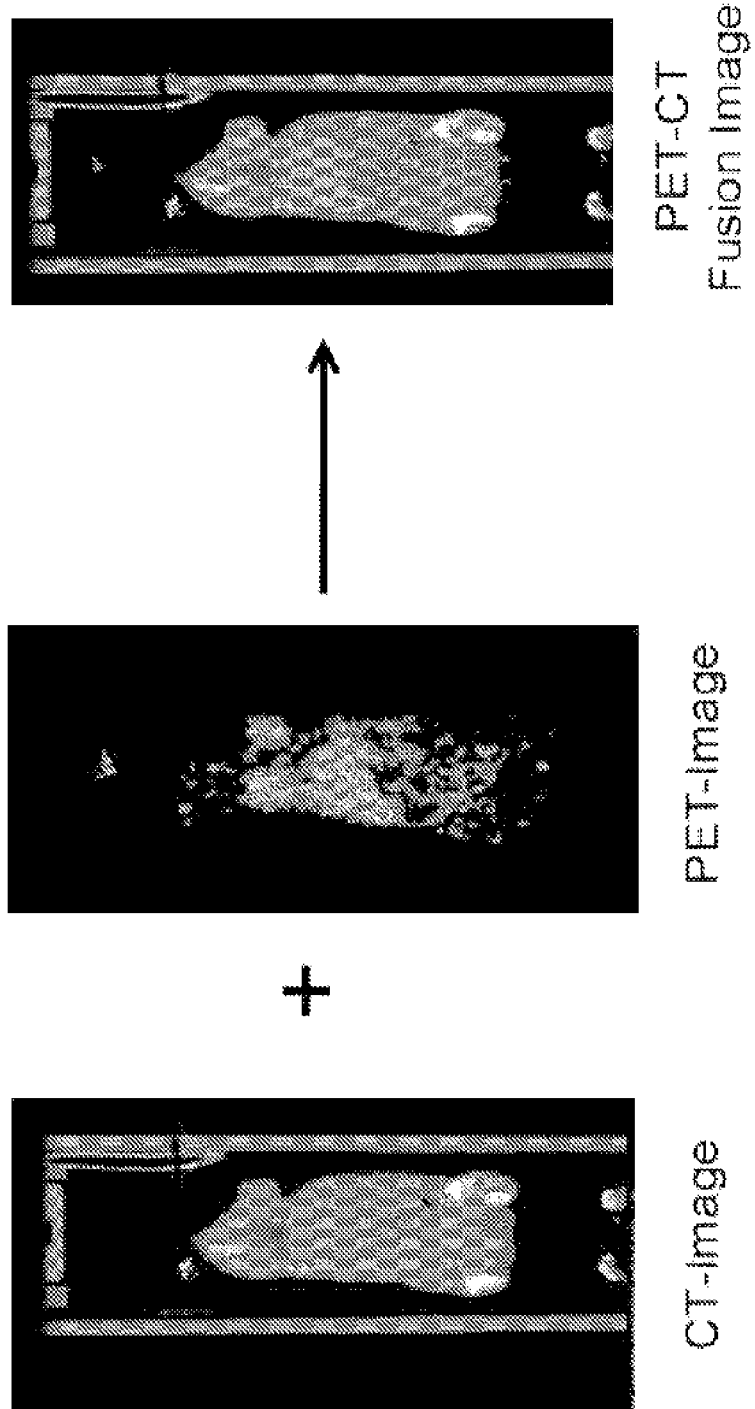
FIG. 12 shows an example of PET-CT image registration to produce a PET-CT fusion image.
Figure 13:
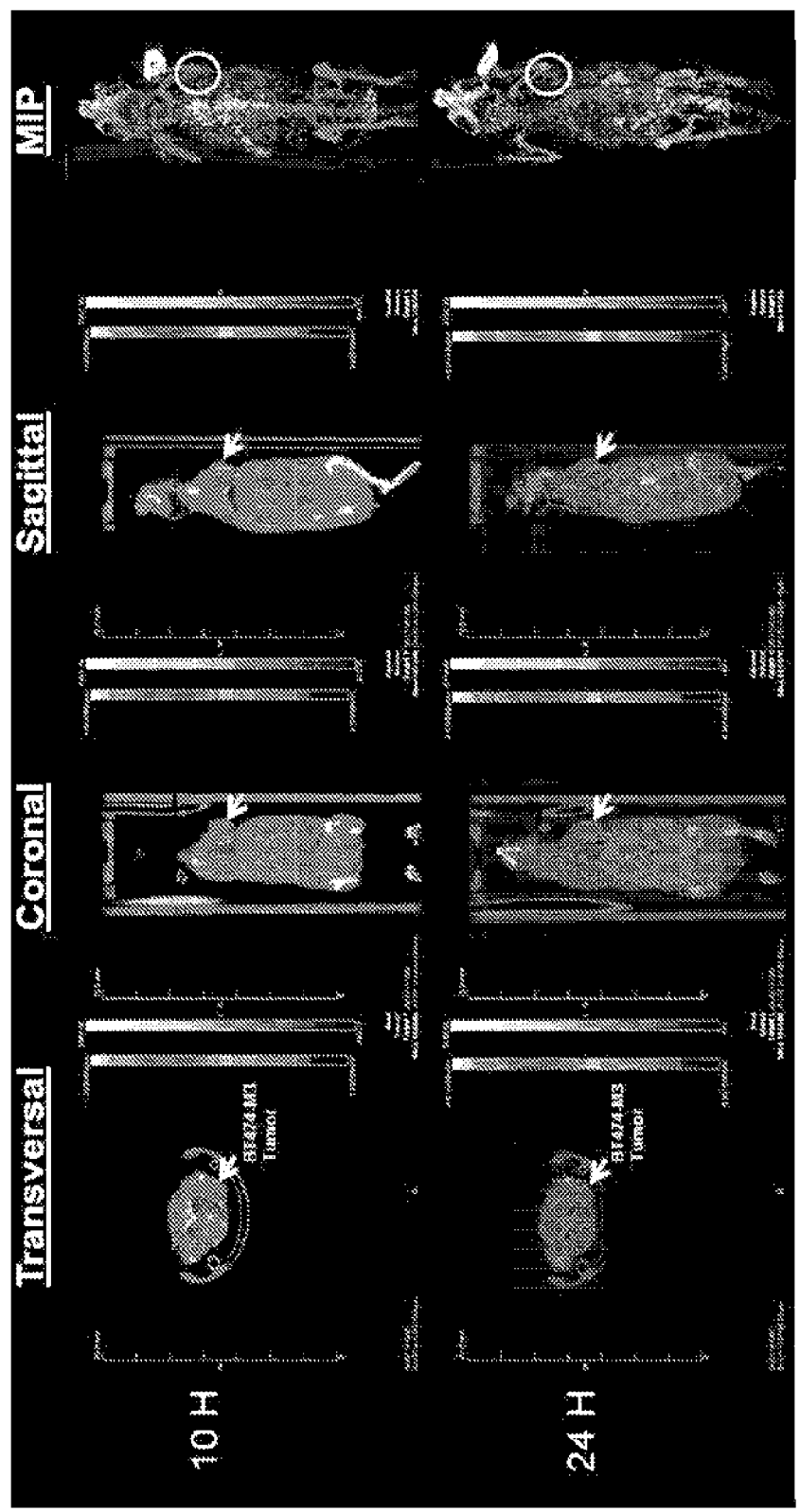
FIG. 13 depicts PET-CT imaging of $^{64}$Cu-loaded Liposome B in tumor bearing mice.

FIG. 12 shows the process by which PET-CT fusion images are generated by registration of a CT-image with a PET-image. The ability to image $^{64}$Cu-loaded liposomes was shown using $^{64}$Cu-loaded Liposome B. PET/CT imaging was performed in BT474-M3 tumor bearing mice (inoculated at mammary fat pad) injected intravenously with Liposome B loaded with $^{64}$Cu:4-DEAP-ATSC. As shown in FIG. 13, $^{64}$Cu-loaded Liposome B accumulated mainly in the liver and spleen, as well as in the circulatory system as a result of the long-circulating characteristics of liposome. Significant accumulation of $^{64}$Cu-loaded Liposome B was also detected at the tumor site at 10 and 24 hours post-injection.

Example 10: Pharmacokinetics and Biodistribution of Liposome A

Figure 14A:
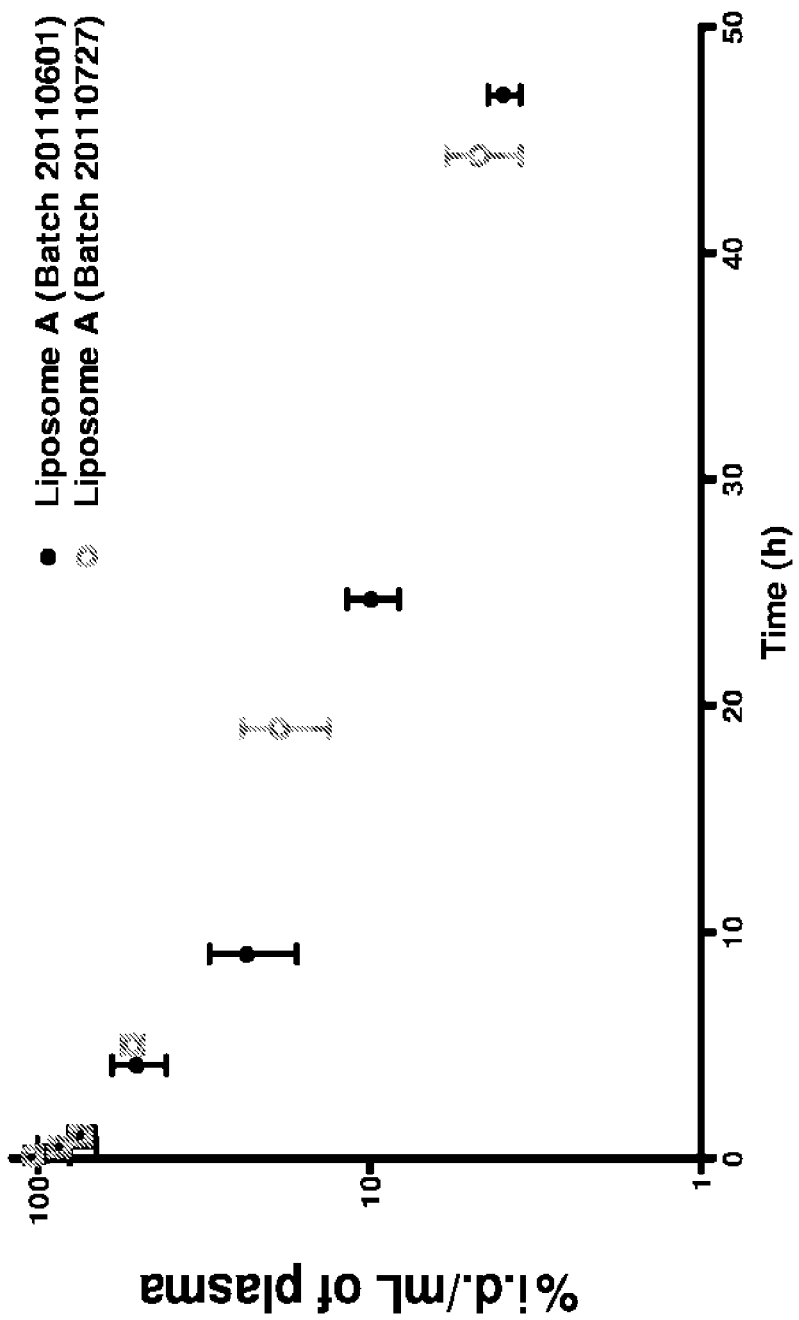
FIG. 14A is a graph depicting the pharmacokinetics of two batches of Liposome A in CD-1 mice.
Figure 14B:
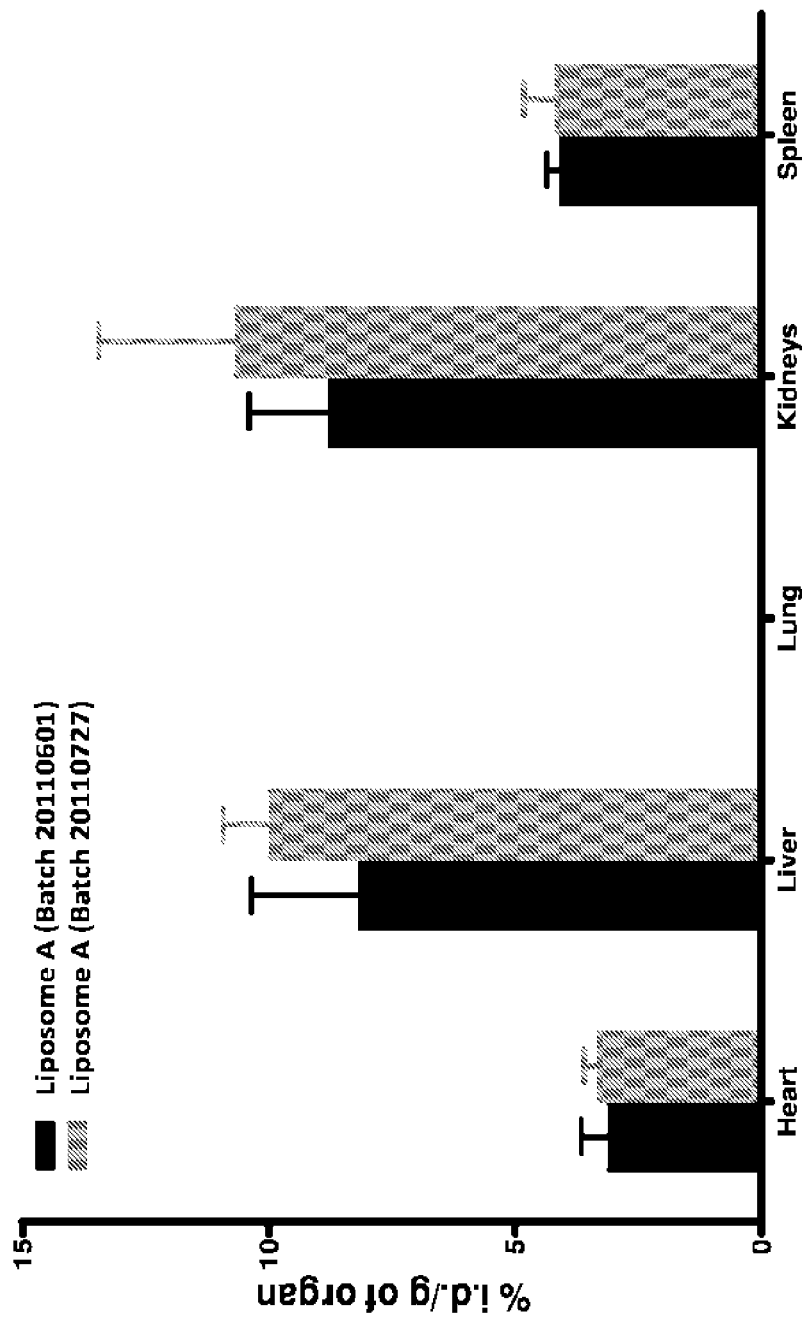
FIG. 14B is a bar chart depicting the bio-distribution of Liposome A in heart, liver, lung, kidney, and spleen of CD-1 mice.

The pharmacokinetics and biodistribution of Liposome A was evaluated in non-tumor bearing CD-1® mice (Charles River Laboratories, Wilmington Mass.). Mice were injected with one of two batches of Liposome A (100-200 µCi/mouse, 20 µmol phospholipid/kg). Blood samples were withdrawn from the saphenous vein at the indicated time points. Plasma concentration of $^{64}$Cu was measured using the gamma-counter (FIG. 14A). Data are also included for comparison from pharmacokinetic studies with $^{64}$Cu-loaded Liposome B in CD-1 mice (quantified $^{64}$Cu radioactivity and doxorubicin content), as well as Liposome B administered in NCI-N87 and BT474-M3 mouse xenograft models (quantified doxorubicin content). The pharmacokinetics of Liposome A was shown to be highly reproducible between different batches, and was consistent with plasma clearance profiles of Liposome B, which has similar formulation properties. Biodistribution of Liposome A was studied by quantifying the amount of $^{64}$Cu in different organs using a gamma-counter. The liver, spleen, and kidneys were found to show significant accumulation of Liposome A (FIG. 14B).

Figure 15A:
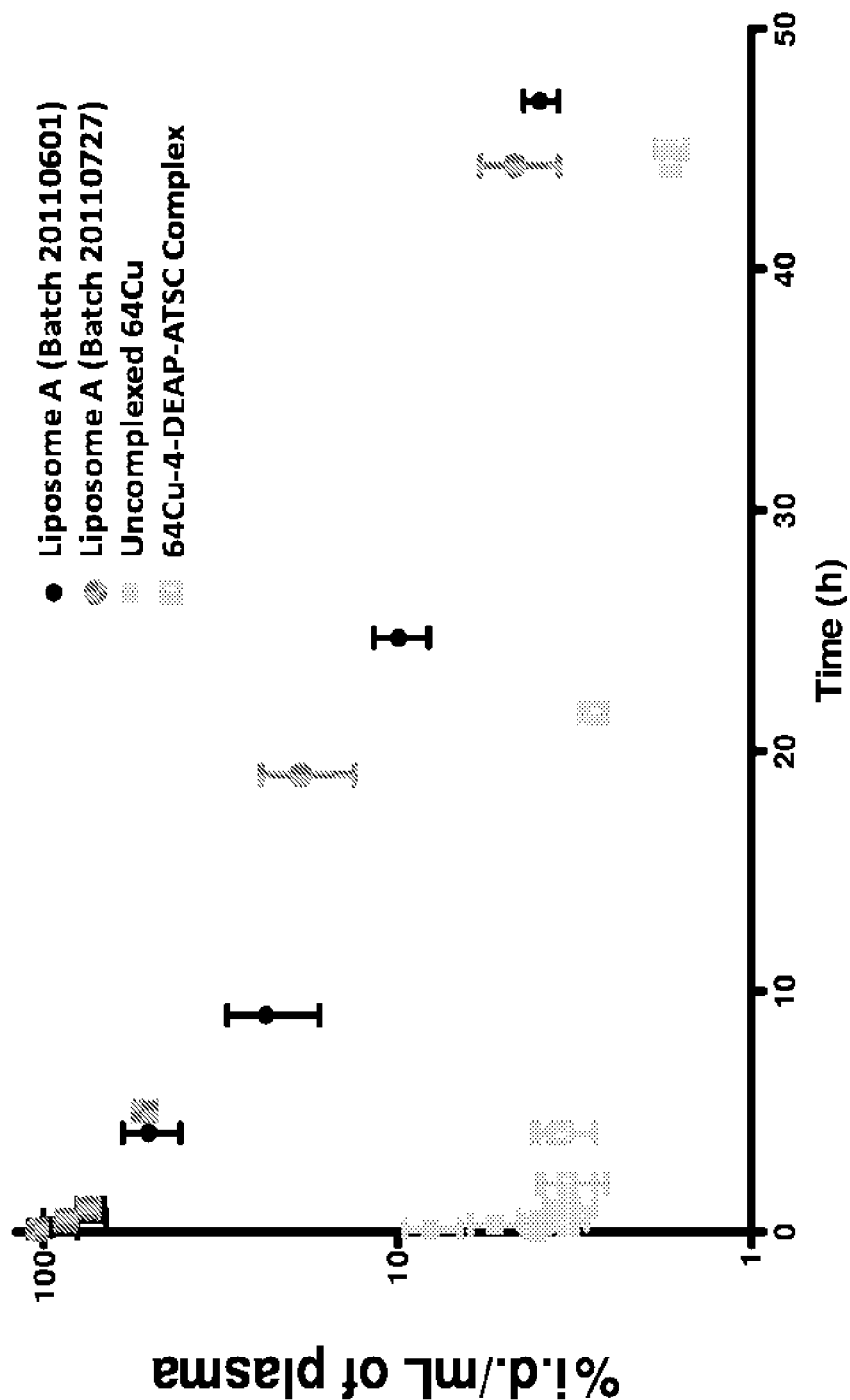
FIG. 15A is a graph depicting the pharmacokinetics of two batches of Liposome A, uncomplexed $^{64}$Cu or $^{64}$Cu:4-DEAP-ATSC in CD-1 mice.
Figure 15B:
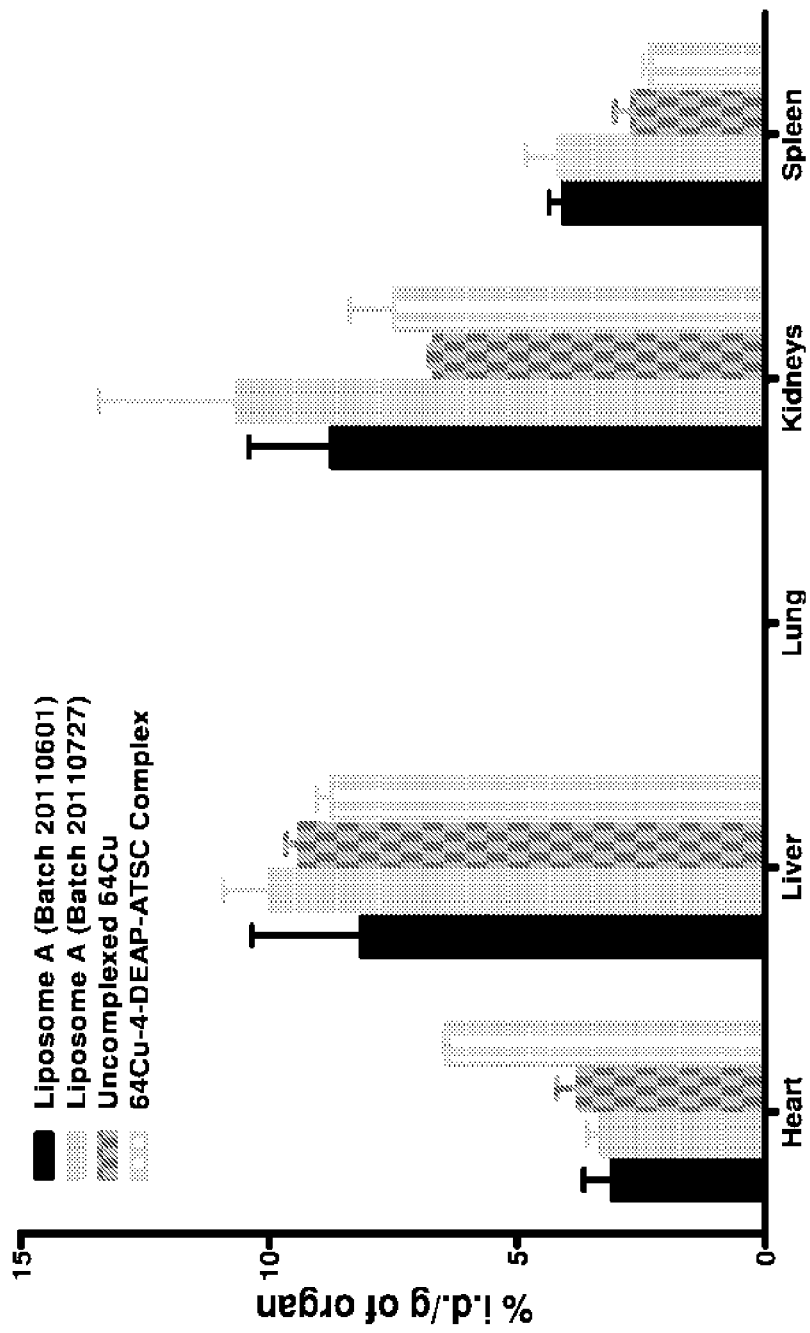
FIG. 15B is a bar chart depicting the biodistribution of two batches of Liposome A, uncomplexed $^{64}$Cu or $^{64}$Cu:4-DEAP-ATSC in heart, liver, lung, kidney, and spleen of CD-1 mice.

Example 11: In Vivo PK and Biodistribution of Liposome A Compared to Uncomplexed $^{64}$Cu and $^{64}$Cu:4-DEAP-ATSC Complex CD-1 mice were injected intravenously with uncomplexed $^{64}$Cu or $^{64}$Cu:4-DEAP-ATSC complex A (100-200 µCi/mouse). As shown in FIG. 15A, plasma clearances of uncomplexed $^{64}$Cu and $^{64}$Cu:4-DEAP-ATSC complexes were significantly faster than Liposome A, suggesting that the $^{64}$Cu:4-DEAP-ATSC complexes are stably encapsulated within the excipient liposomes. Biodistribution of Liposome A was evaluated using the same method as in the previous Example. The heart liver, spleen, and kidneys were found to show significant accumulation of Liposome A (FIG. 15B).

Figure 16A:
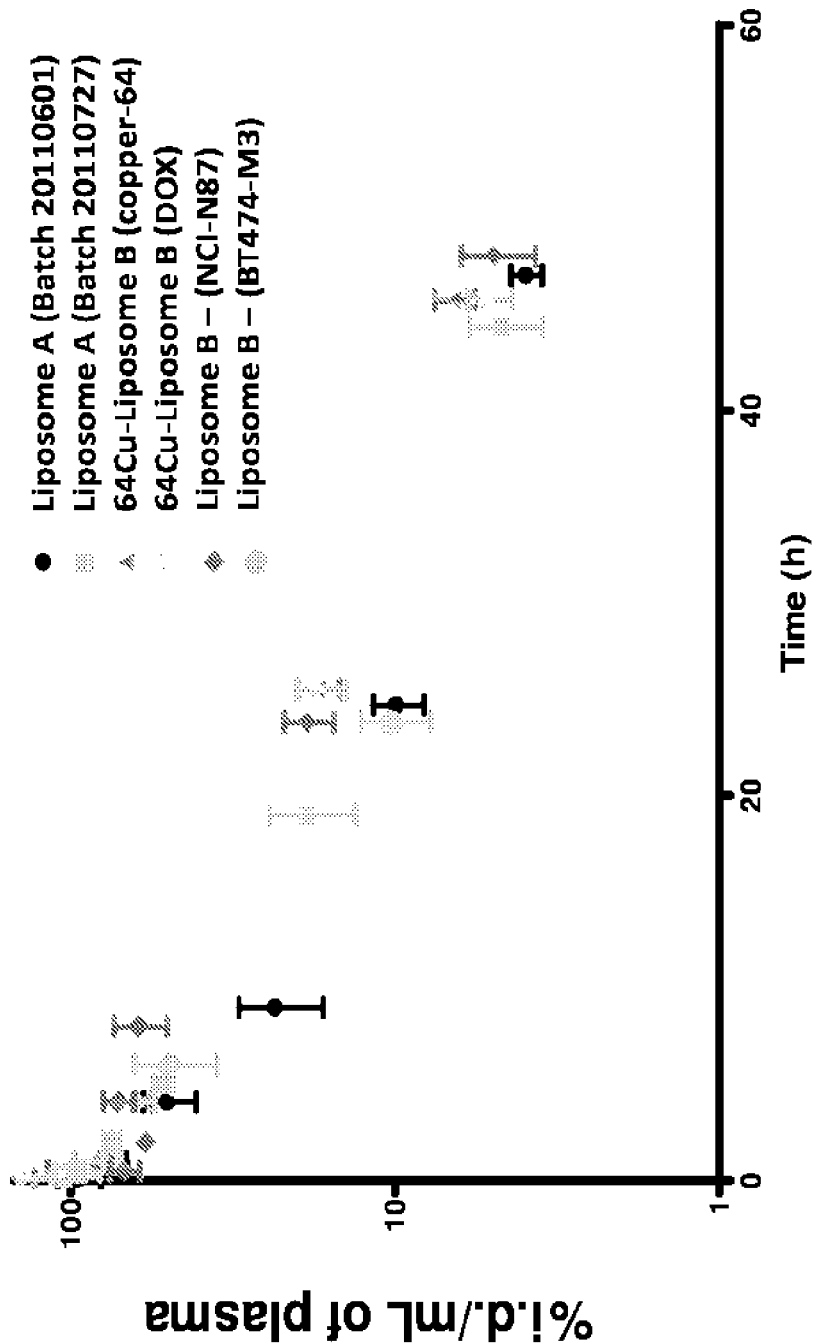
FIG. 16A is a graph depicting the pharmacokinetics of Liposome A in comparison to $^{64}$Cu-labeled Liposome B containing doxorubicin in CD-1 mice, as well as Liposome B in both an NCI-N87 and BT474-M3 mouse xenograft models.
Figure 16B:
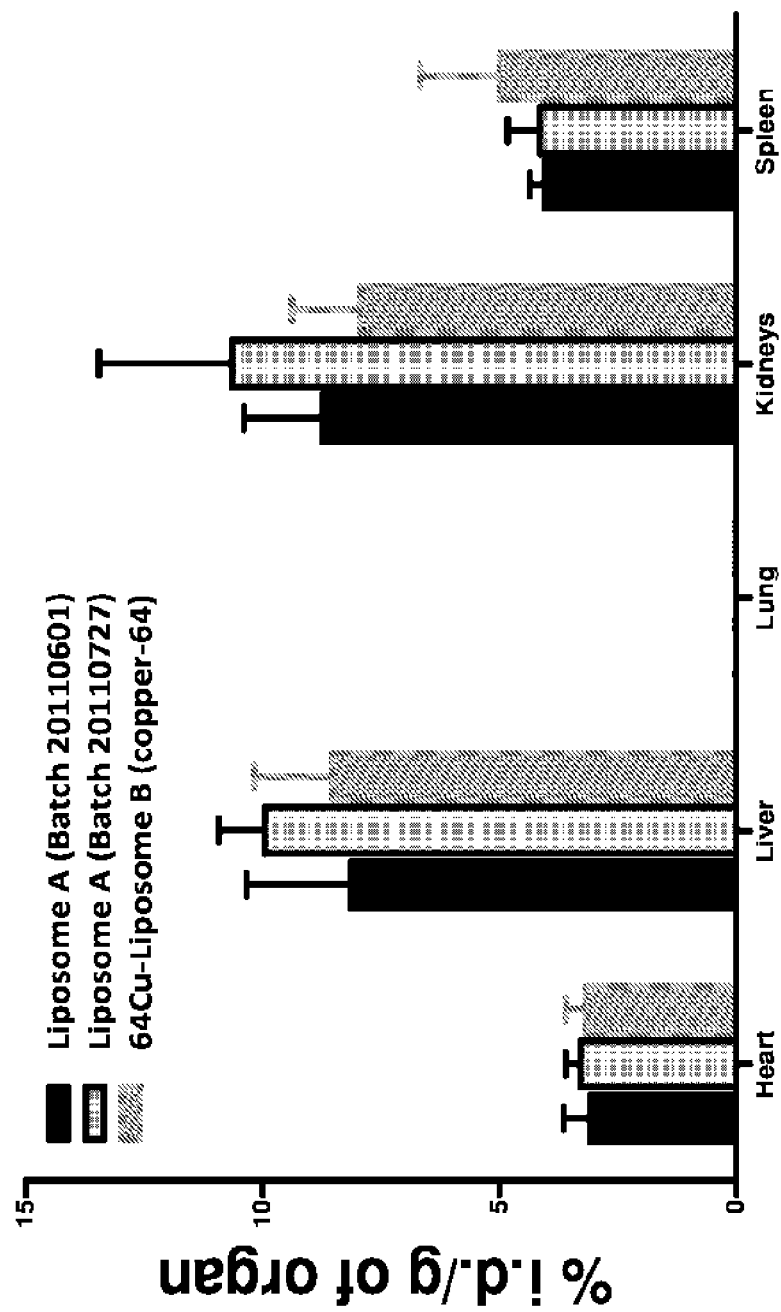
FIG. 16B is a bar chart depicting the biodistribution of Liposome A in comparison to $^{64}$Cu-labeled Liposome B in CD-1 mice.

Example 12: In Vivo PK and Biodistribution of Liposome A Compared to Other Liposomal Formulations The Her2-targeted liposomal doxorubicin, Liposome B, was loaded with $^{64}$Cu:4-DEAP-ATSC complex using the same protocol as described for Liposome A. Unexpectedly, it was found that the residual pH gradient in the liposome following loading with doxorubicin was sufficient to induce stable entrapment of the $^{64}$Cu:4-DEAP-ATSC complex within the liposome. Pharmacokinetics of $^{64}$Cu-loaded Liposome B was studied by quantifying both the plasma levels of $^{64}$Cu and doxorubicin using gamma-counter and HPLC, respectively. As shown in FIG. 16A, there was no significant difference between the plasma clearance of $^{64}$Cu and doxorubicin, indicating that the $^{64}$Cu:4-DEAP-ATSC complex is stably entrapped within the liposome in vivo. In addition, the plasma clearance of $^{64}$Cu-loaded Liposome B was comparable to the plasma clearance of Liposome B in tumor-bearing mice. Importantly, the pharmacokinetics of Liposome A resembles that of $^{64}$Cu-loaded Liposome B. The biodistribution of Liposome A was also similar to that of $^{64}$Cu-loaded Liposome B in CD-1 mice (FIG. 16B). Importantly, these results suggest that the $^{64}$Cu:4-DEAP-ATSC complex is highly stable within the liposome and is representative of the in vivo distribution of the liposome.

Figure 16C:
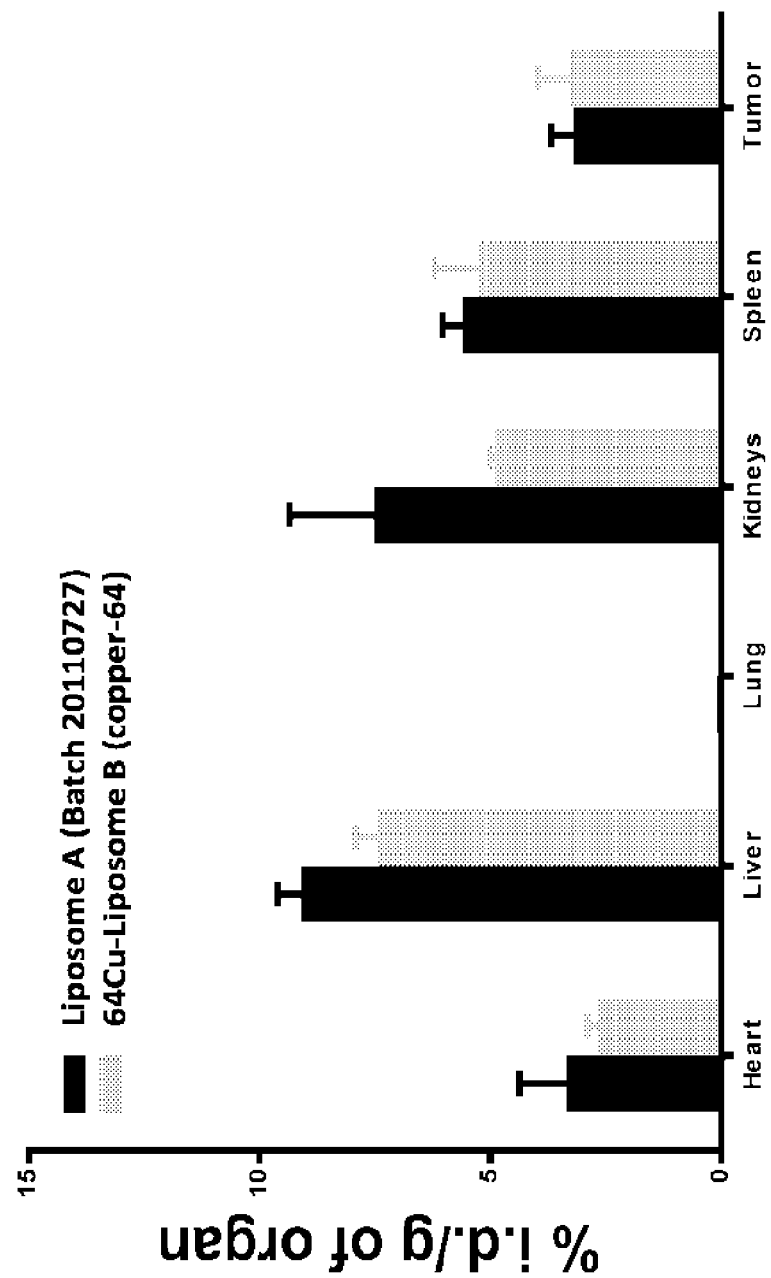
FIG. 16C is a bar chart depicting the biodistribution of Liposome A in comparison to $^{64}$Cu-labeled Liposome B in BT474-M3 mouse xenograft models.

Liposome A or Liposome B loaded with $^{64}$Cu:4-DEAP-ATSC was administered intravenously in BT474-M3 tumor bearing mice (inoculated at mammary fat pad). After 48 hours post-injection, tumor accumulations of $^{64}$Cu-loaded Liposome B and Liposome A were found to be approximately 4% injected dose per gram of tissue (i.d./g), similar to that previously reported by Kirpotin et al., as well as data obtained with Liposome B in the BT474-M3 breast cancer and NCI-N87 gastric cancer mouse xenograft tumor models. These results show that $^{64}$Cu remains stably-associated with liposomes for at least 48 hours (FIG. 16C). This suggests that 4-DEAP-ATSC provides an effective means for radiolabeling liposomes and is suitable as a PET agent for tracking tumor deposition of a liposomal imaging agent.

Example 13: $^{64}$Cu:4-DEAP-ATSC Toxicity Estimates and Dose Levels

The reference range for copper (Cu) in human blood is 70-150 µg/dL (ATSDR Toxicological Profile for Copper, 2004). Toxic dose levels are estimated to be >10 mg/person/day (~154 µg/kg; 65 kg adult) over several weeks. Liposome A will be dosed at 0.2 µg/patient (~0.003 µg/kg), which is ~51,000 times lower than the potentially toxic repeat dose range for copper. Additionally, all Liposome A associated copper will be chelated and encapsulated prior to administration.

Figure 17:
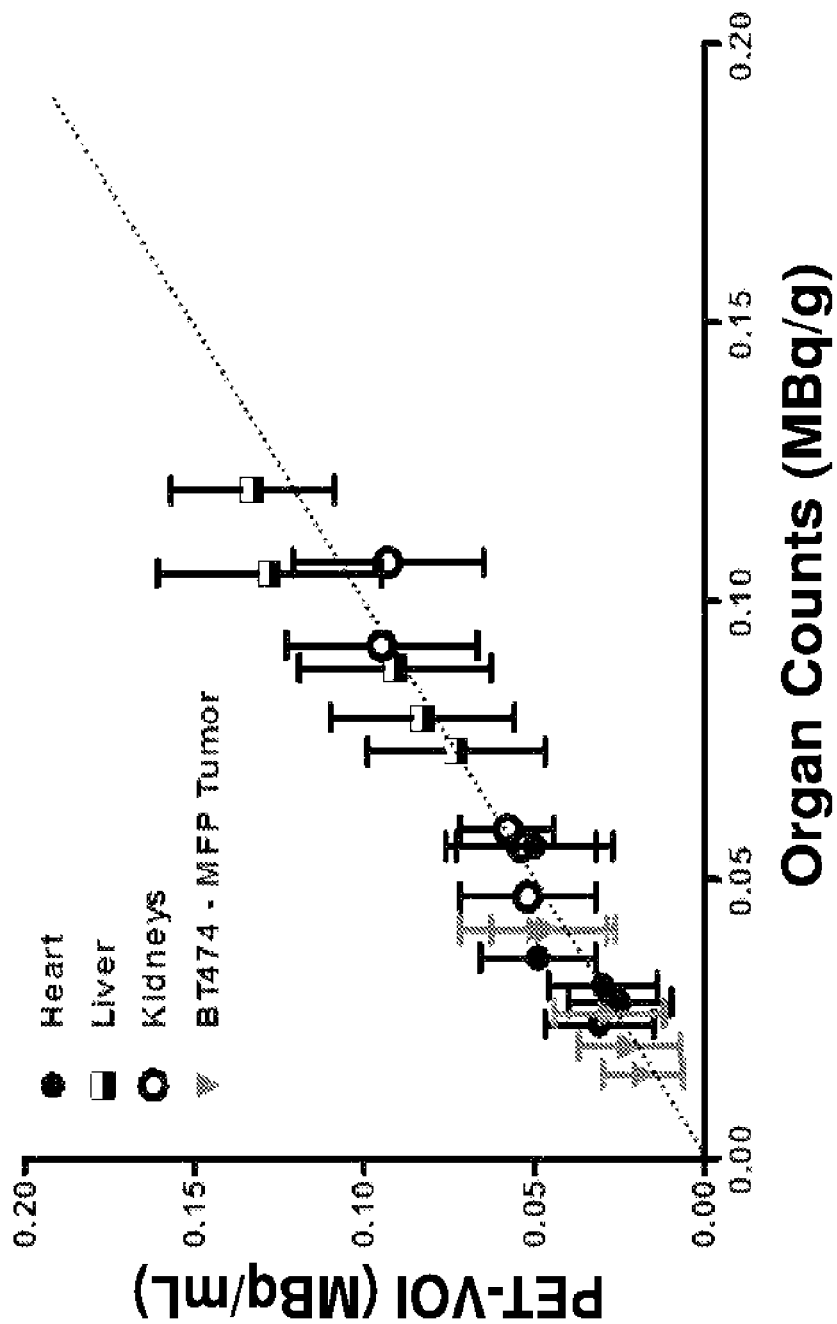
FIG. 17 is a graph showing quantification of Liposome A in liver (square), heart (solid circle), kidneys (open circle) and BT474-MFP Tumor. The y-axis is intensity in mega-Becquerels (MBq) per mL, and the x-axis is organ counts in MBq per gram.

Example 14: Validating Liposome A as a Quantifiable PET Agent for Accurately Measuring Liposome Biodistribution Organ uptake of Liposome A in tumor-bearing mice was quantified using volume of interest (VOI)-based analysis of PET images, as well as gamma-counting of the excised organs (i.e. traditional biodistribution study). The mice were imaged using PET at 48 hours after injected with Liposome A. Immediately following imaging the mice were sacrificed for organ collection. Each individual organ was then subjected to gamma-counting for quantifying the amount of radioactivity (i.e. $^{64}$Cu). VOI analyses on the PET images were performed by contouring the organs based on the CT-images registered on the PET images. As shown in FIG. 17, the radioactivity measured for each organ on the PET images correlates well with the radioactivity measured via gamma-counting for the corresponding organs. A similar study was performed on a set of PET images acquired at 18 hours post-injection; the results obtained were in agreement with the aforementioned data set collected at 48 hours post-injection. This demonstrates that biodistribution of Liposome A can be studied via PET scan of subject injected with Liposome A.

Figure 18:
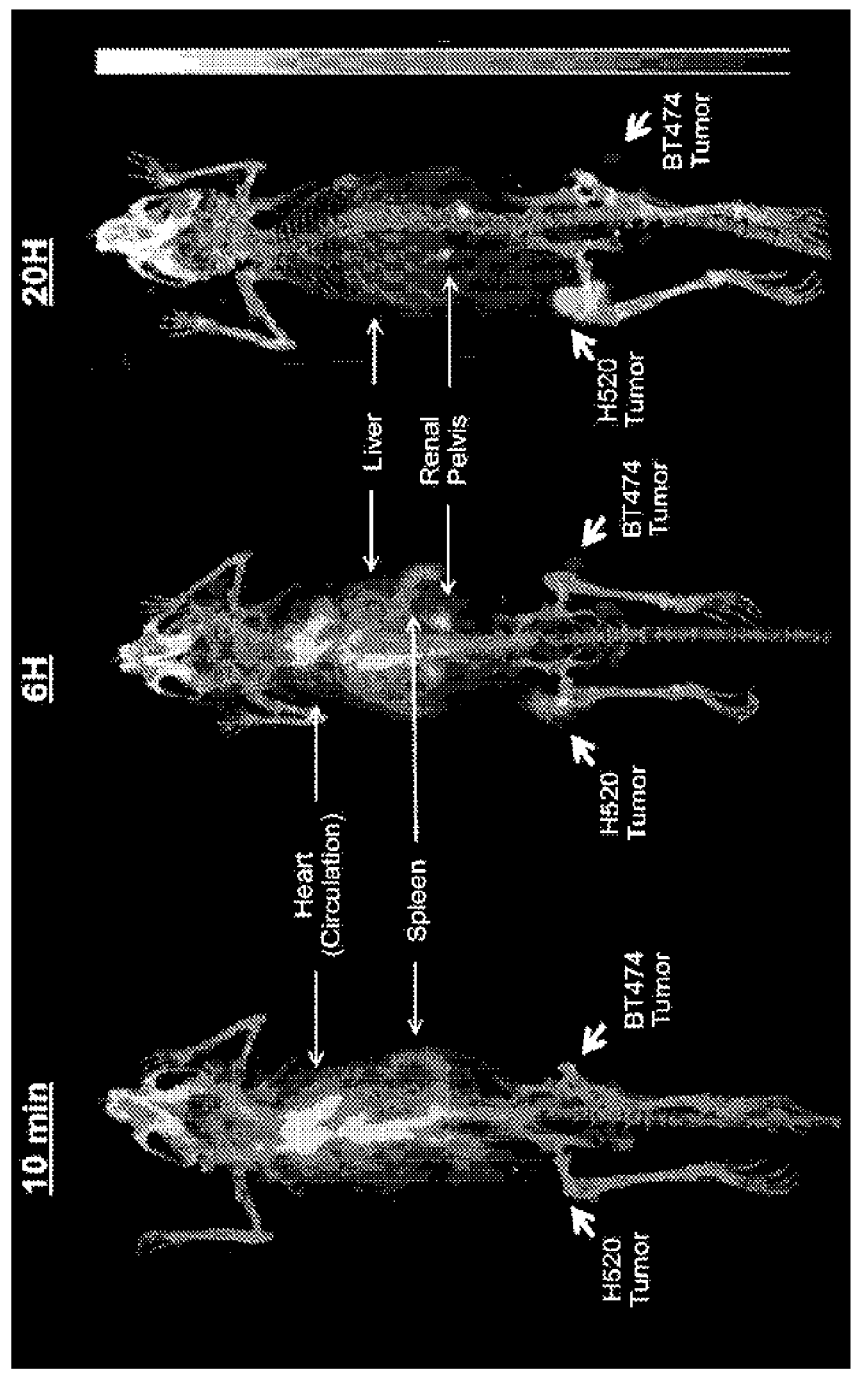
FIG. 18 is a composite of images showing PET-CT images of H520 (NSCLC) and BT474-M3 (breast) tumor-bearing mice injected with Liposome A. Images were taken at 10 minutes, 6 hours, and 20 hours post-injection.

Example 15: Liposome a as a Tool for Measuring Tumor Deposition of Liposomal Drugs In order to demonstrate that Liposome A can be used as a tool for measuring the variability of liposomal drugs in tumors; PET-CT imaging was performed on xenografts bearing two different types of tumor. Mice inoculated with H520 (NSCLC model cell line ATCC® #HTB-182™) and BT474-M3 (breast cancer model cell line, see (see Noble, *Cancer Chemother. Pharmacol.* 2009 64:741-51) cells on the right and left flanks, respectively, were injected with Liposome A. PET-CT imaging was performed at 10 minutes, 6 hours, and 20 hours, post-injection. As shown in FIG. 18, at 10 minutes post-injection, Liposome A was seen mainly in circulation, which is known to be characteristics of long-circulating liposome. At 6 hours post-injection, accumulation of Liposome A was clearly visible in the spleen and liver, along with significant deposition in the H520 tumor. At 20 hours post-injection, accumulation of Liposome A in the H520 and BT474-M3 tumors reached 23% i.d./g and 3% i.d./g according to VOI analysis on the PET images; demonstrating that variability of liposomal deposition in tumors can be measured using Liposome A and PET imaging. The amounts of tumor deposition of Liposome A in the two tumors were also confirmed via organ excision and gamma-scintillation counting.

Example 16: $^{64}$Cu Loading into Drug-Containing Liposomes (Liposome B, Liposome C)

Using a similar loading procedure as described above for Liposome A, $^{64}$Cu:4-DEAP-ATSC has also been successfully loaded into other liposomal formulations that contain chemotherapeutic agents via the residual chemical gradient. Examples of such liposomal formulations include the HER2-targeted doxorubicin-loaded Liposome B, the irinotecan-loaded Liposome C, as well as the commercially available doxorubicin-loaded Doxil®. $^{64}$Cu:4-DEAP-ATSC with chelation efficiency >90% was mixed with varying amounts of Liposome B, Liposome C, or $^{Doxil}$®. The mixture was then incubated in a water bath at 65° C. for 10 minutes and the loading procedure was subsequently quenched in an ice water bath. Using size exclusion chromatography, it was determined that more than 90% of $^{64}$Cu:4-DEAP-ATSC can be loaded into Liposome B (Table 8), Liposome C (Table 9), and Doxil® (Table 10) below.

TABLE 8

$^{64}$Cu-loaded Liposome B

| 4-DEAP-ATSC:Doxorubicin Ratio (mol %) | $^{64}$Cu Loading Efficiency |
|---|---|
| 0.16 mol % | 98% |
| 0.7 mol % | 95% |
| 1.0 mol % | 92% |
| 1.6 mol % | 95% |
| 2.0 mol % | 92% |
| 2.7 mol % | 96% |
| 4.0 mol % | 93% |
| 8.0 mol % | 93% |
| 40 mol % | 90% |

TABLE 9

$^{64}$Cu-loaded Liposome C

| 4-DEAP-ATSC:Irinotecan Ratio (mol %) | $^{64}$Cu Loading Efficiency |
|---|---|
| 0.01 mol % | 97% |
| 0.2 mol % | 95% |
| 0.6 mol % | 97% |
| 2.5 mol % | 97% |
| 12.5 mol % | 90% |

TABLE 10

$^{64}$Cu-loaded Doxil ®

| 4-DEAP-ATSC:Doxorubicin Ratio (mol %) | $^{64}$Cu Loading Efficiency |
|---|---|
| 0.6 mol % | 94% |
| 2.0 mol % | 96% |
| 4.0 mol % | 96% |
| 8.0 mol % | 96% |
| 40 mol % | 91% |

Example 17: Storage Stability of 4-DEAP-ATSC Formulations

Various 4-DEAP-ATSC formulations (see Table 10 below) were stored under different conditions. At designated time points, samples were collected where their storage stability were evaluated by functional readouts.

TABLE 11

4-DEAP-ATSC Formulations and Storage Conditions

| Sample | Buffer | Buffer Strength | pH | Formulation | Fill | Temperature |
|---|---|---|---|---|---|---|
| C1 | Citrate Buffer | 0.1M | 6 | Liquid | Air | −20° C., 4° C., 30° C., 37° C. |
| C2 | Citrate Buffer | 0.1M | 6 | Liquid | Argon | −20° C., 4° C., 30° C., 37° C. |

TABLE 11-continued

4-DEAP-ATSC Formulations and Storage Conditions

| Sample | Buffer | Buffer Strength | pH | Formulation | Fill | Temperature |
|---|---|---|---|---|---|---|
| C3 | Citrate Buffer | 0.1M | 6 | Lyophilized | Air | −20° C., 4° C., 30° C., 37° C. |
| C4 | Citrate Buffer | 0.1M | 6 | Lyophilized | Argon | −20° C., 4° C., 30° C., 37° C. |
| C5 | Citrate Buffer | 0.1M | 6.5 | Liquid | Air | −20° C., 4° C., 30° C., 37° C. |
| C6 | Citrate Buffer | 0.1M | 7 | Liquid | Air | −20° C., 4° C., 30° C., 37° C. |
| C7 | Citrate Buffer | 0.1M | 7 | Liquid | Argon | −20° C., 4° C., 30° C., 37° C. |
| C8 | Citrate Buffer | 0.005M | 6 | Liquid | Air | −20° C., 4° C., 30° C., 37° C. |
| C9 | Citrate Buffer | 0.005M | 7 | Liquid | Air | −20° C., 4° C., 30° C., 37° C. |
| C10 | Citrate Buffer | 0.005M | 7 | Liquid | Argon | −20° C., 4° C., 30° C., 37° C. |
| C11 | Water | (Contains 0.0005M Citric acid) | | Liquid | Air | −20° C., 4° C., 30° C., 37° C. |
| C12 | Water | (Contains 0.0005M Citric acid) | | Liquid | Argon | −20° C., 4° C., 30° C., 37° C. |
| C13 | Water | (Contains 0.0005M Citric acid) | | Lyophilized | Argon | −20° C., 4° C., 30° C., 37° C. |
| C14 | Citrate Buffer | 0.1M (with 20 mg/mL mannitol) | 6 | Lyophilized | Air | −20° C., 4° C., 30° C., 37° C. |
| C15 | Citrate Buffer | 0.005M (with 20 mg/mL mannitol) | 6 | Lyophilized | Air | −20° C., 4° C., 30° C., 37° C. |
| C16 | Citrate Buffer | 0.1M | 4 | Liquid | Air | 4° C., 37° C. |
| C16 | Citrate Buffer | 0.1M | 5 | Liquid | Air | 4° C., 37° C. |
| C17 | Citrate Buffer | 0.02M | 4 | Liquid | Air | 4° C., 37° C. |
| C16 | Citrate Buffer | 0.02M | 5 | Liquid | Air | 4° C., 37° C. |

Effect of Storage pH

Figure 19A:
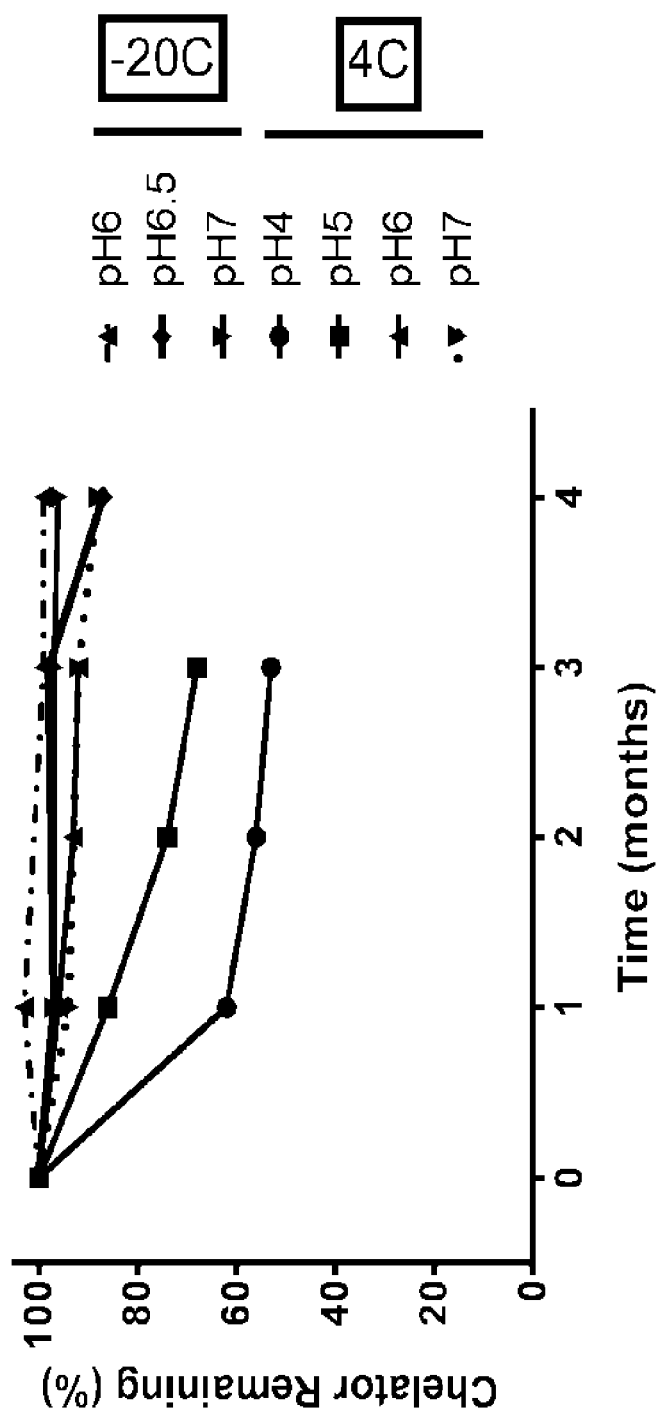
FIG. 19A is a graph showing stability of a 4-DEAP-ATSC formulation stored under varying pH.

4-DEAP-ATSC was formulated in citrate buffer in a range of pH (pH 4-7). As seen in FIG. 19A, the amount of 4-DEAP-ATSC degradation decreases as the storage pH increases in the formulation. At a pH of between 6 and 7, the rates of degradation were very similar, with less than 15% degradation observed over a 4-month period when stored at −20° C. or 4° C.

Effect of Storage Temperature

Figure 19B:
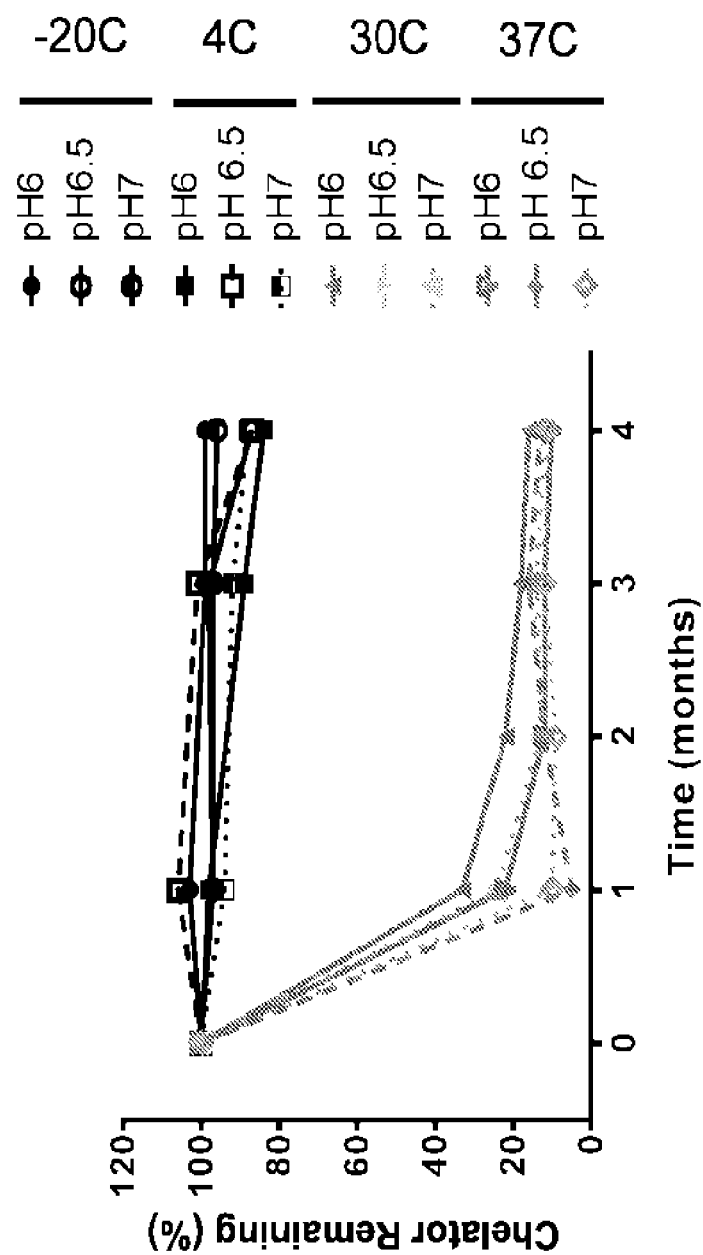
FIG. 19B is a graph showing stability of a 4-DEAP-ATSC formulation stored under varying temperature.

4-DEAP-ATSC formulated in citrate buffer was stored at 4 different temperatures (−20° C., 4° C., 30° C., and 37° C.). As seen in FIG. 19B, significant degradation was observed when the 4-DEAP-ATSC formulations were stored at 30° C. and 37° C. (>60%) over a 1-month period. On the other hand, 4-DEAP-ATSC formulations stored at −20° C. and 4° C. can be stably preserved with less than 15% of degradation detected over a period of 4 months.

Lyophilized Formulations

Figure 19C:
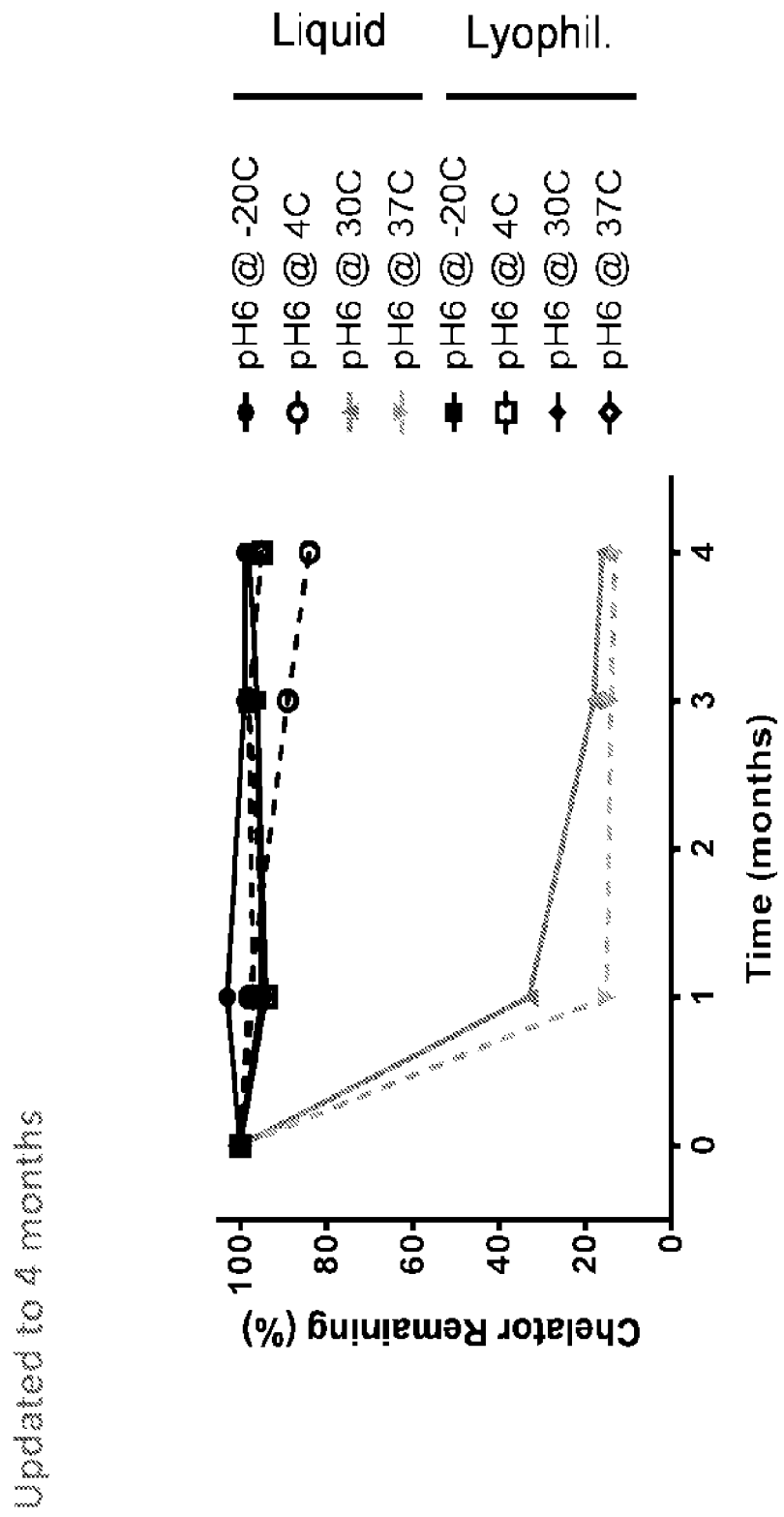
FIG. 19C is a graph showing stability of a 4-DEAP-ATSC formulation stored under lyophilization.
Figure 19D:
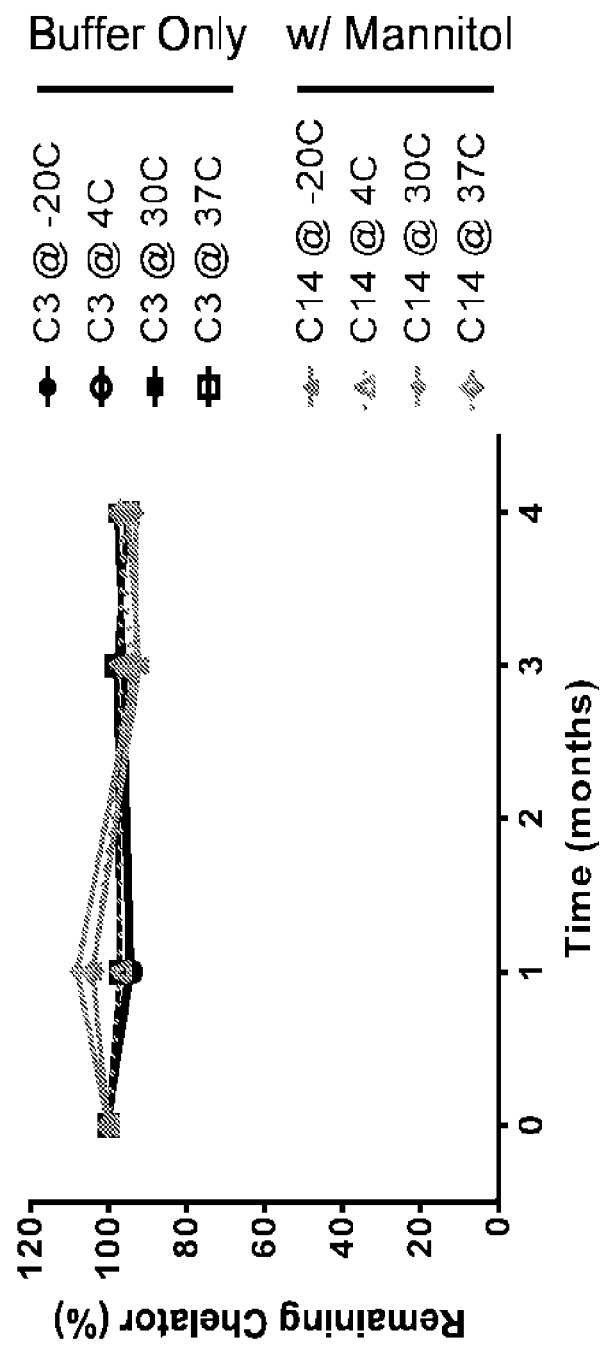
FIG. 19D is a graph showing stability of a 4-DEAP-ATSC formulation stored under lyophilization with mannitol (D).

Various 4-DEAP-ATSC formulations were lyophilized and stored under different conditions to study the effect of lyophilization on their storage stability. FIG. 19C illustrates that lyophilization is an effective method to inhibit degradation of 4-DEAP-ATSC, reversing any temperature-related degradation process as described previously. In addition, mannitol was added to the formulation to serve as a bulking agent for lyophilization. As shown in FIG. 19D, mannitol has no effect on the storage stability of 4-DEAP-ATSC.

Storage Under Inert Gas Atmosphere

Figure 19E:
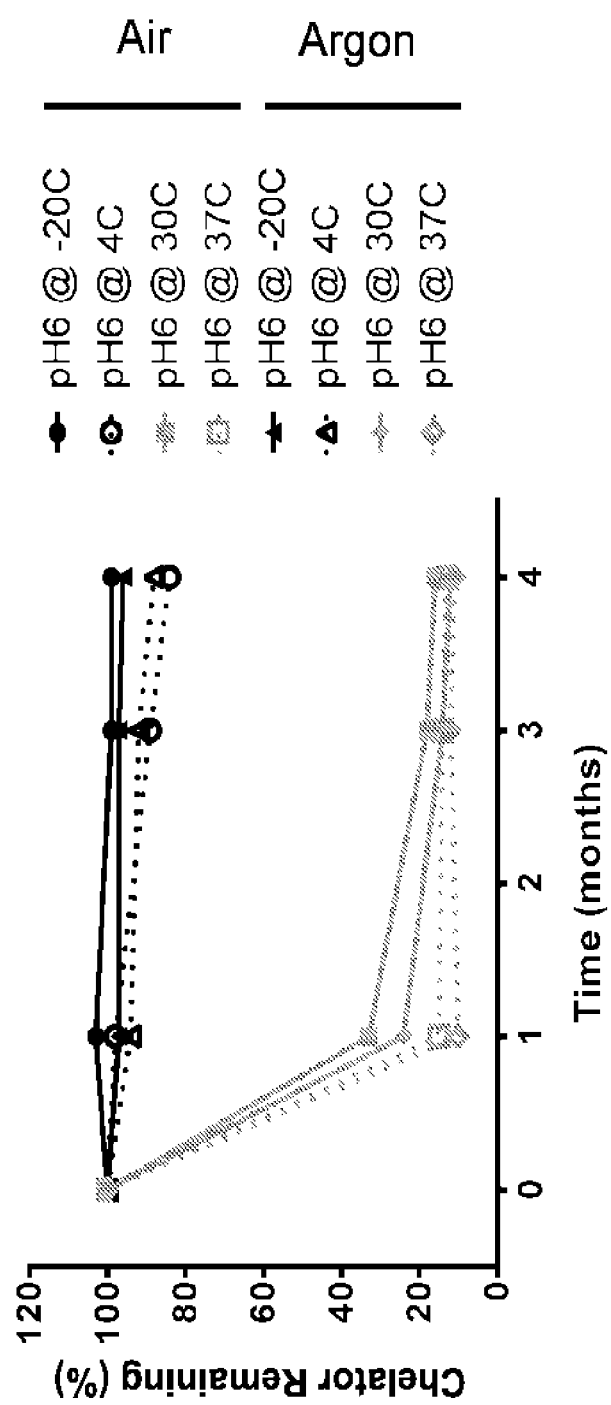
FIG. 19E is a graph showing stability of a 4-DEAP-ATSC formulation stored under inert gas/air atmosphere.
Figure 19F:
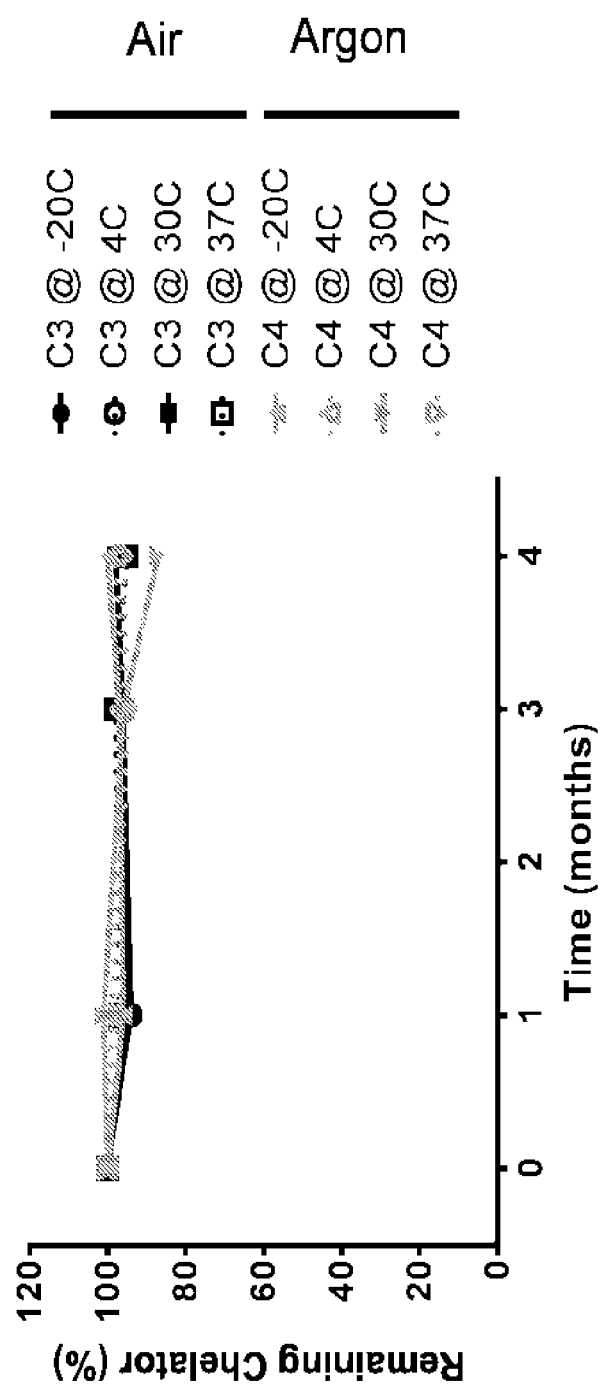
FIG. 19F is a graph showing stability of a 4-DEAP-ATSC formulation stored under inert gas/air-filled lyophilization.

A set of 4-DEAP-ATSC formulations was filled with argon as an alternative means to improve storage stability of the liquid formulations. FIG. 19E illustrates that storage under inert gas atmosphere did not improve storage stability of 4-DEAP-ATSC liquid formulations. Significant degradation was still detected in formulations stored at elevated temperatures (30° C. and 37° C.). Additionally, storage stability of inert gas-filled lyophilized formulations was similar to air-filled lyophilized formulations (FIG. 19F).

Example 18: Storage Stability of Excipient Liposome of Various Compositions

Various excipient liposome formulations (see Table 12 and 13 below) were stored under different conditions. At designated time points, samples were collected and their storage stability was evaluated by functional readouts (loading of $^{64}$Cu:4-DEAP-ATSC and in vivo stability of $^{64}$Cu:4-DEAP-ATSC-loaded liposomes), as well as degradation of lipid components, as determined by HPLC/ELSD (high performance liquid chromatography coupled to an evaporative light scattering detector).

TABLE 12

Excipient Lipid Formulations with Ammonium Sulfate Gradients and Storage Conditions

| Sample | Lipid Composition | External pH | Ammonium Sulfate | Sodium Sulfate | Temperature |
|---|---|---|---|---|---|
| L1 | HSPC:Cholesterol:PEG-DSPE (3:1:1 wt ratio) | 6.5 | 20 mM | 70 mM | 4° C., 37° C. |
| L2 | HSPC:Cholesterol:PEG-DSPE (3:1:1 wt ratio) | 6.5 | 50 mM | 50 mM | 4° C., RT, 37° C. |
| L3 | DSPC:Cholesterol:PEG-DSPE (3:1:1 wt ratio) | 6.5 | 50 mM | 50 mM | 4° C., 30° C., 37° C. |
| L4 | DSPC:Cholesterol:PEG-DSPE (3:1:1 wt ratio) | 6.5 | 125 mM | — | 4° C., 30° C., 37° C. |
| L5 | DSPC:Cholesterol:PEG-DSPE (3:1:1 wt ratio) | 6.5 | 250 mM | — | 4° C., 30° C., 37° C. |
| L6 | Sphingomyelin:Cholesterol:PEG-DSPE (3:1:1 wt ratio) | 6.5 | 50 mM | 50 mM | 4° C., 30° C., 37° C. |
| L7 | Sphingomyelin:Cholesterol:PEG-DSPE (3:1:1 wt ratio) | 6.5 | 125 mM | — | 4° C., 30° C., 37° C. |

TABLE 12-continued

Excipient Lipid Formulations with Ammonium Sulfate Gradients and Storage Conditions

| Sample | Lipid Composition | External pH | Ammonium Sulfate | Sodium Sulfate | Temperature |
|---|---|---|---|---|---|
| L8 | Sphingomyelin:Cholesterol:PEG-DSPE (3:1:1 wt ratio) | 6.5 | 250 mM | — | 4° C., 30° C., 37° C. |
| L9 | Sphingomyelin:Cholesterol:PEG-DSPE (3:1:1 wt ratio) | 7.4 | 50 mM | 50 mM | 4° C., 30° C., 37° C. |
| L10 | Sphingomyelin:Cholesterol:PEG-DSPE (3:1:1 wt ratio) | 7.4 | 125 mM | — | 4° C., 30° C., 37° C. |
| L11 | Sphingomyelin:Cholesterol:PEG-DSPE (3:1:1 wt ratio) | 7.4 | 250 mM | — | 4° C., 30° C., 37° C. |
| L12 | Sphingomyelin:Cholesterol:PEG-DSG (3:1:1 wt ratio) | 6.5 | 50 mM | 50 mM | 4° C., 30° C., 37° C. |
| L13 | Sphingomyelin:Cholesterol:PEG-DSG (3:1:1 wt ratio) | 6.5 | 125 mM | — | 4° C., 30° C., 37° C. |
| L14 | Sphingomyelin:Cholesterol:PEG-DSG (3:1:1 wt ratio) | 7.4 | 50 mM | 50 mM | 4° C., 30° C., 37° C. |
| L15 | Sphingomyelin:Cholesterol:PEG-DSG (3:1:1 wt ratio) | 7.4 | 125 mM | — | 4° C., 30° C., 37° C. |
| L16 | Sphingomyelin:Cholesterol:PEG-DSGE (3:1:1 wt ratio) | 6.5 | 50 mM | 50 mM | 4° C., 30° C., 37° C. |
| L17 | Sphingomyelin:Cholesterol:PEG-DSGE (3:1:1 wt ratio) | 6.5 | 125 mM | — | 4° C., 30° C., 37° C. |
| L18 | Sphingomyelin:Cholesterol:PEG-DSPE (3:1:0.5 wt ratio) [PEG-DSPE Inserted post-extrusion] | 7.4 | 50 mM | 50 mM | 4° C., 30° C., 37° C. |
| L19 | Sphingomyelin:Cholesterol:PEG-DSPE (3:1:0.5 wt ratio) [PEG-DSPE Inserted post-extrusion] | 7.4 | 125 mM | — | 4° C., 30° C., 37° C. |

TABLE 13

Excipient Lipid Formulations with Triethylammonium Sucrose Octasulfate Gradients and Storage Conditions

| Sample | Lipid Composition | External pH | Triethylammonium Sucrose Octasulfate | Temperature |
|---|---|---|---|---|
| L20 | DSPC:Cholesterol:PEG-DSPE (3:1:1 wt ratio) | 7.2 | 0.142N | 4° C., 30° C. |
| L21 | DSPC:Cholesterol:PEG-DSPE (3:1:1 wt ratio) | 7.2 | 0.215N | 4° C., 30° C. |
| L22 | DSPC:Cholesterol:PEG-DSPE (3:1:1 wt ratio) | 7.2 | 0.43N | 4° C., 30° C. |
| L23 | DSPC:Cholesterol:PEG-DSPE (3:1:1 wt ratio) | 6.5 | 0.43N | 4° C., 30° C. |
| L24 | DSPC:Cholesterol:PEG-DSPE (3:1:1 wt ratio) | 7.4 | 0.43N | 4° C., 30° C. |
| L25 | HSPC:Cholesterol:PEG-DSPE (3:1:1 wt ratio) | 7.2 | 0.043N | 4° C., 30° C. |
| L26 | HSPC:Cholesterol:PEG-DSPE (3:1:1 wt ratio) | 7.2 | 0.086N | 4° C., 30° C. |

TABLE 13-continued

Excipient Lipid Formulations with Triethylammonium Sucrose Octasulfate Gradients and Storage Conditions

| Sample | Lipid Composition | External pH | Triethylammonium Sucrose Octasulfate | Temperature |
|---|---|---|---|---|
| L27 | HSPC:Cholesterol:PEG-DSPE (3:1:1 wt ratio) | 7.2 | 0.142N | 4° C., 30° C. |
| L28 | HSPC:Cholesterol:PEG-DSPE (3:1:1 wt ratio) | 7.2 | 0.215N | 4° C., 30° C. |
| L29 | HSPC:Cholesterol:PEG-DSPE (3:1:1 wt ratio) | 7.2 | 0.43N | 4° C., 30° C. |
| L30 | Sphingomyelin:Cholesterol:PEG-DSPE (3:1:1 wt ratio) | 7.2 | 0.215N | 4° C., 30° C. |
| L31 | Sphingomyelin:Cholesterol:PEG-DSPE (3:1:1 wt ratio) | 7.2 | 0.43N | 4° C., 30° C. |

Excipient Liposome with Various Lipid Compositions

Figure 20A:
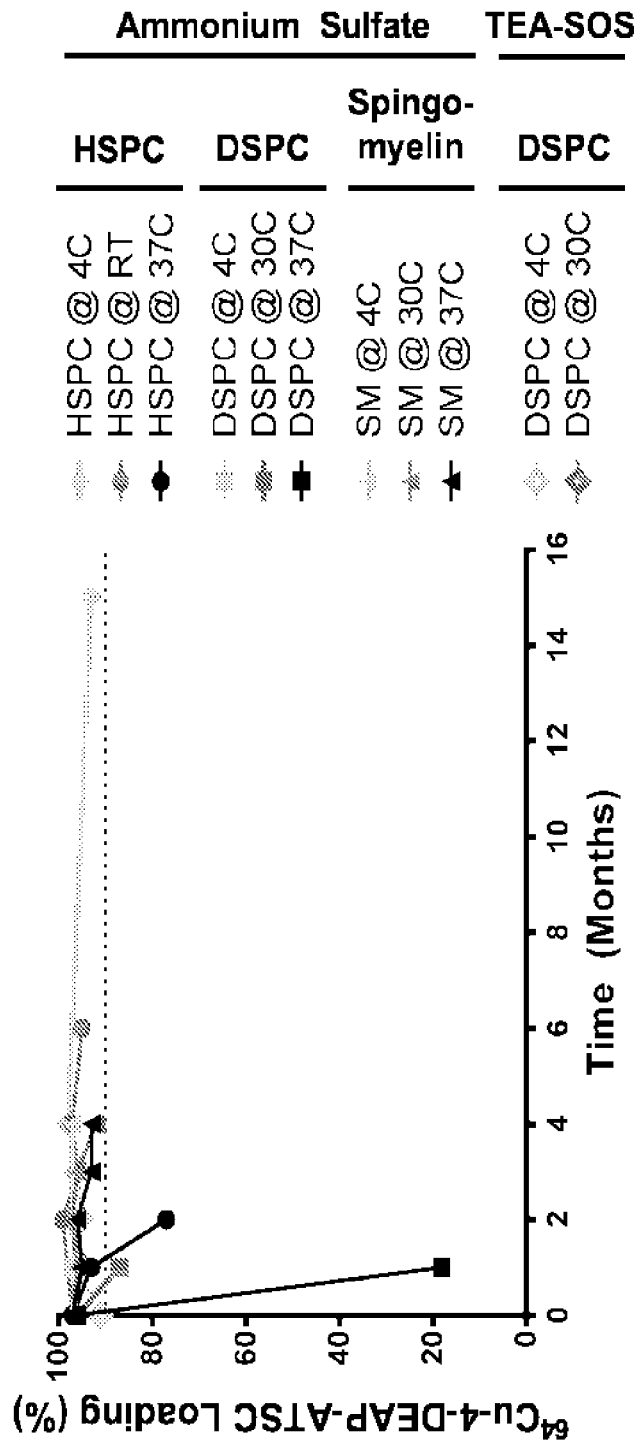
FIGS. 20A-20G are a series of graphs showing storage stability of various excipient liposome formulations. Multiple lipid compositions and two distinct internal buffers (ammonium sulfate and triethylammonium sucrose octasulfate (TEA-SOS) were tested.

All liposome formulations listed above were shown to result in acceptable $^{64}$Cu:4-DEAP-ATSC loading (>95%) at the beginning of the study. HSPC—Ammonium Sulfate formulations were demonstrated to retain the ability to load $^{64}$Cu:4-DEAP-ATSC over a 6-month storage period when stored at room temperature (room temperature (RT) is defined as temperatures varying between 22-25° C.), and for at least 15 months when stored at 4° C. At 1-month, DSPC—Ammonium Sulfate formulations did not retain an acceptable level of $^{64}$Cu:4-DEAP-ATSC loading (acceptable level of loading defined as >90%) (FIG. 20A). All sphingomyelin formulations retained the ability to load $^{64}$Cu:4-DEAP-ATSC at all storage temperatures for at least four months. DSPC formulations encapsulating triethylammonium sucrose octasulfate (TEA-SOS) maintained the ability to load $^{64}$Cu:4-DEAP-ATSC for at least 4 months when stored at 4° C.

Figure 20B:
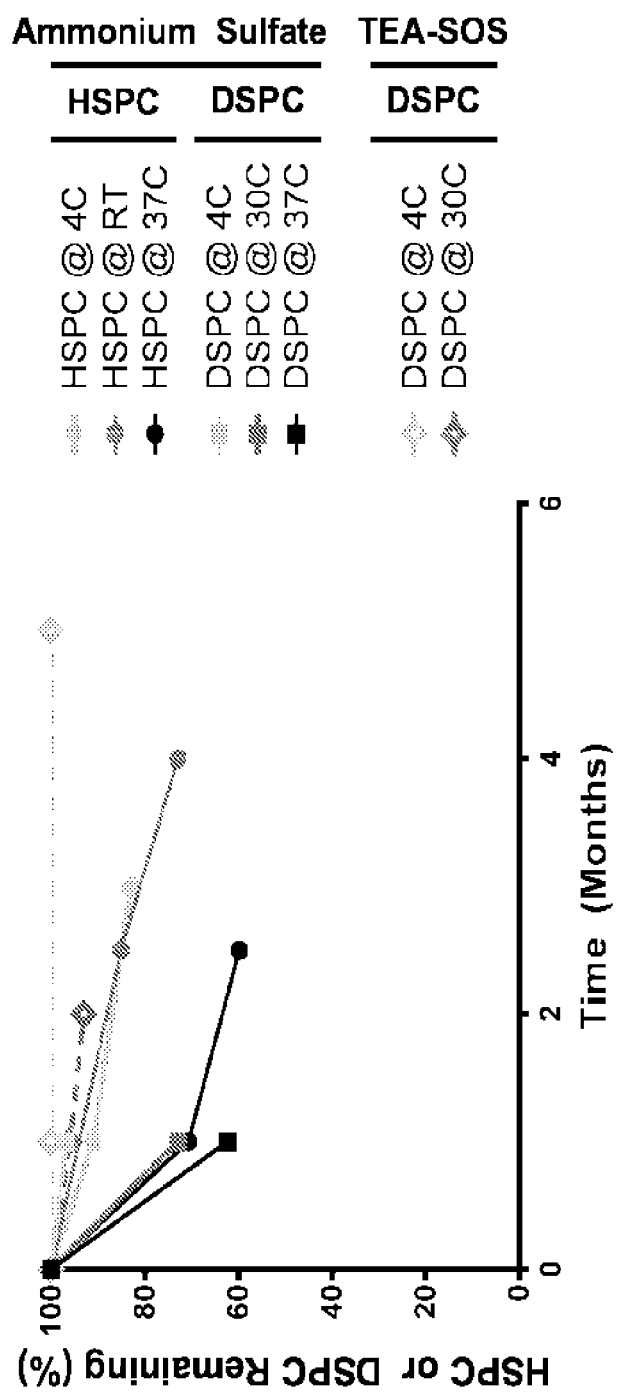

HPLC/ELSD results support the above observation where significant amounts of lipid degradation were detected in both HSPC and DSPC formulations encapsulating ammonium sulfate (FIG. 20B). Lipid breakdown in the sphingomyelin formulations was minimal with a small amount of stearic acid detected at 2-months onwards, which may be attributed to the degradation of PEG-DSPE located on the inner liposomal membrane. Similarly, lipid breakdown in DSPC formulations encapsulating TEA-SOS was minimal over a period of 2 months at 30° C. storage, with no lipid degradation detected over 5 months at 4° C. storage (FIG. 20B).

Figure 20C:
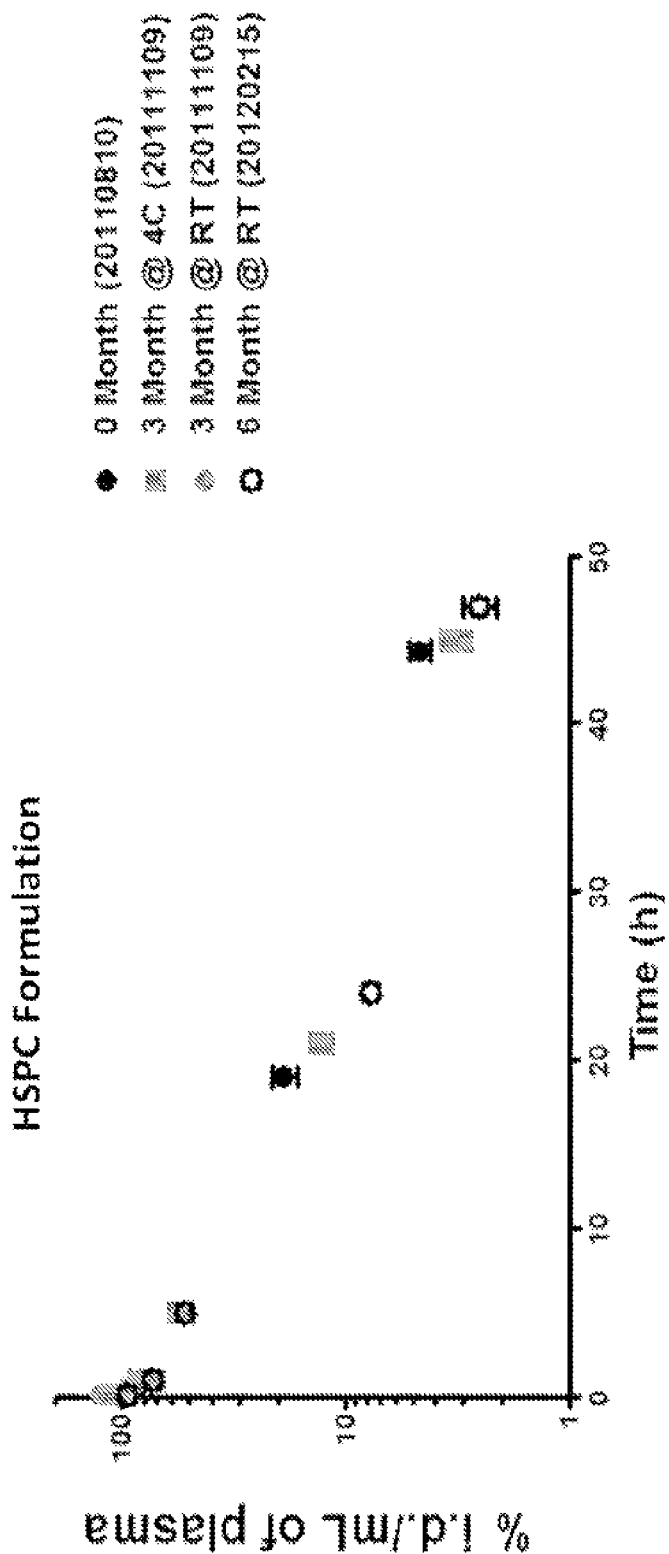
Figure 20D:
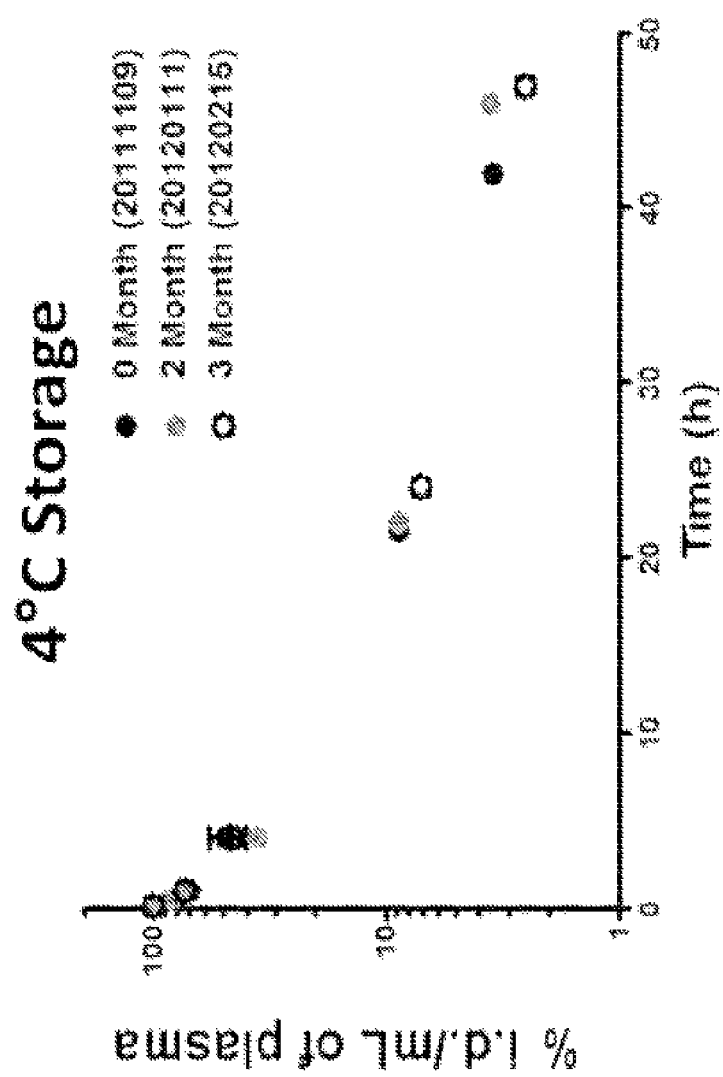
Figure 20E:
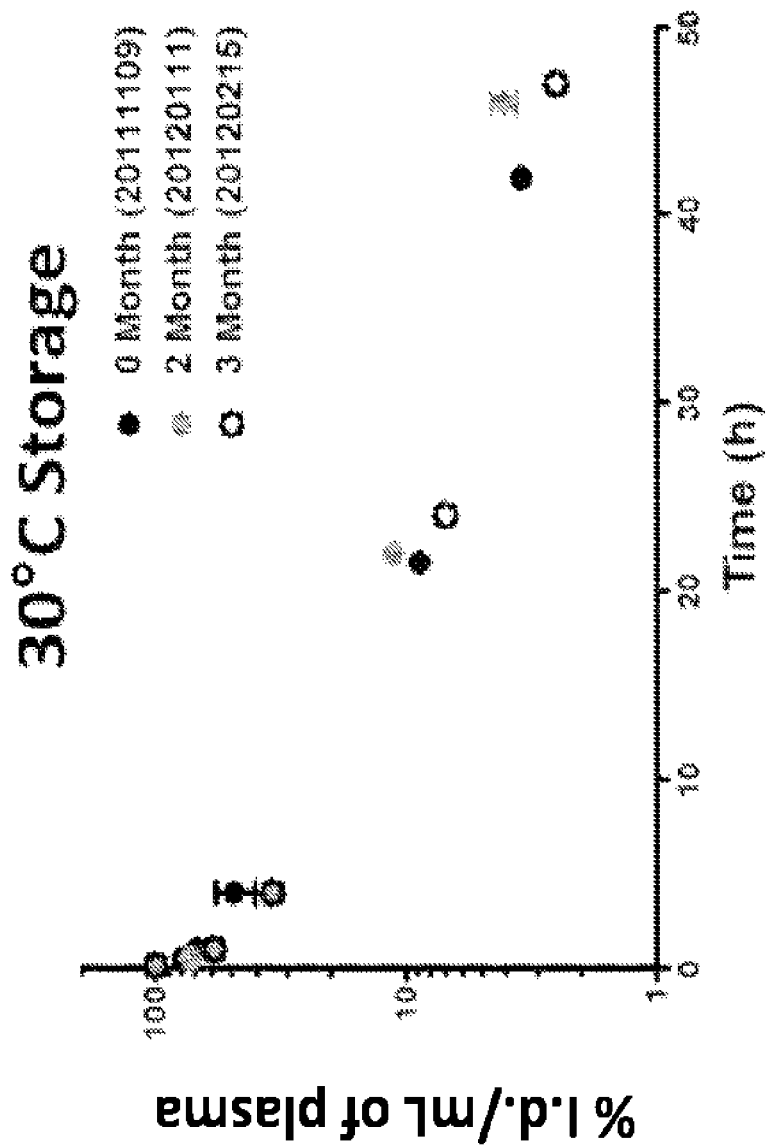
Figure 20F:
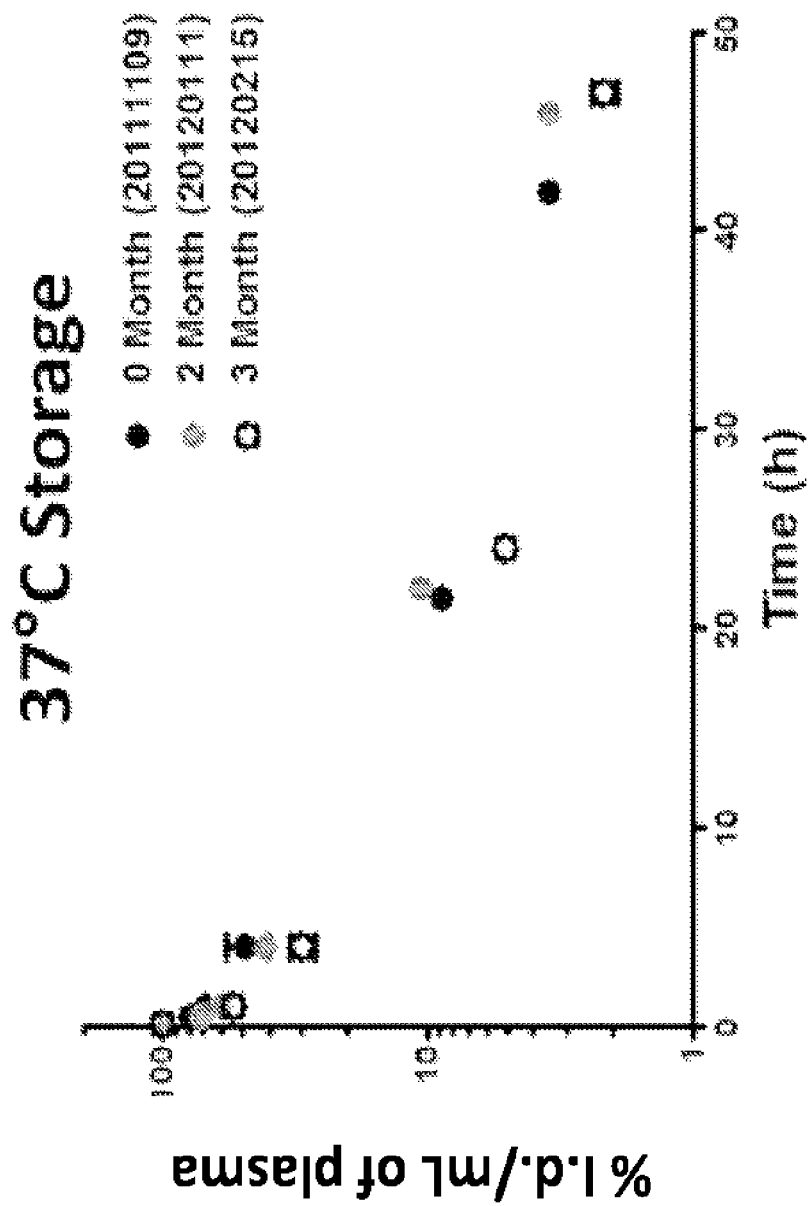

An in vivo stability study was performed as described in Example 10 to investigate the pharmacokinetics profiles of the liposome formulations that were stored under the aforementioned conditions. Even though a significant amount of lipid was degraded in the HSPC formulations, the $^{64}$Cu-DEAP-ATSC-loaded HSPC liposome still performed stably in vivo after 6-month storage at room temperature (FIG. 20C). Similar results were obtained for the sphingomyelin formulations over a 3-month storage period at elevated temperatures (FIG. 20D (4° C.), 20E (30° C.), and 20F (37° C.)).

Figure 20G:
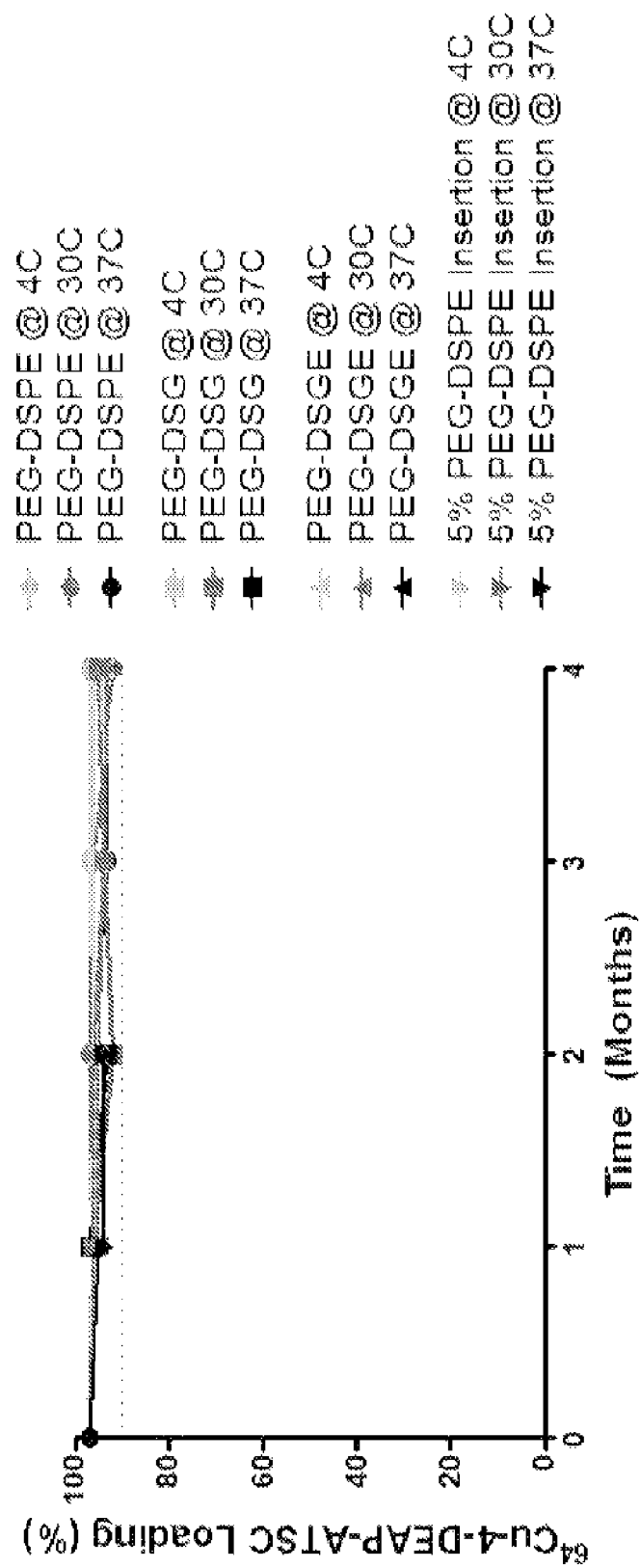

Additional formulations were also studied by varying the types and amount of PEG-lipid. Since sphingomyelin was not susceptible to hydrolysis, the PEG-DSPE in the sphingomyelin formulation remains the source of lipid degradation induced by the low intraliposomal pH (presence of ammonium sulfate as a loading gradient). In place of the PEG-DSPE lipid, variations of the sphingomyelin formulations were studied, including PEG-DSGE, PEG-DSG, or post-insertion of (reduced amount) PEG-DSPE into preformed liposomes. All these formulations were shown to result in excellent $^{64}$Cu:4-DEAP-ATSC loading (>90%) following 4-months of storage at elevated temperatures (FIG. 20G).

Figure 21A:
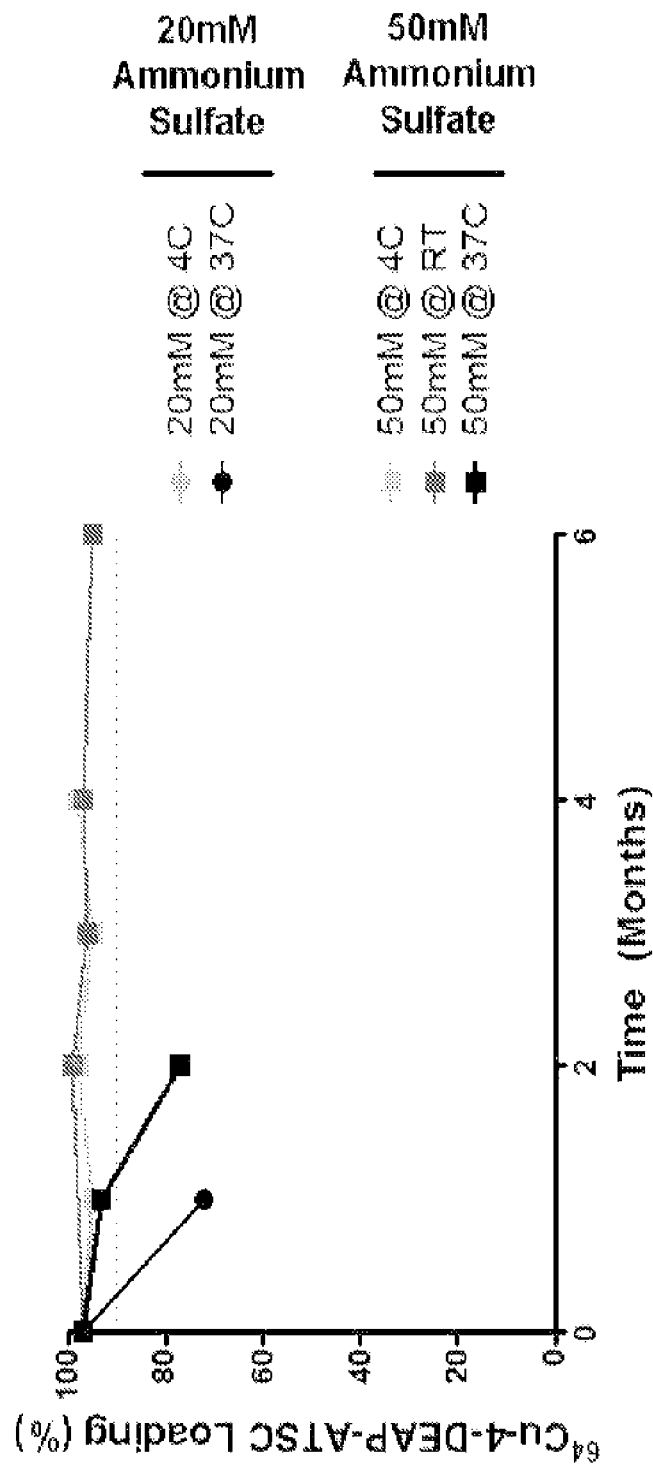
FIGS. 21A-21C are a series of graphs showing storage stability of excipient liposome formulations with various strengths of electro-chemical loading gradient.

Example 19: Storage Stability of Excipient Liposome Containing Various Loading Gradient Strengths Liposome formulations with various strengths of loading gradient containing 20, 50, 125, 250 mM of ammonium sulfate were prepared. The effects of loading gradient strengths on the $^{64}$Cu:4-DEAP-ATSC loading and storage stability were examined. FIG. 21A illustrates the effect of loading gradient strengths on the $^{64}$Cu:4-DEAP-ATSC loading efficiency of HSPC liposome stored under different conditions. The 20 mM formulation of liposomes was shown to fail loadability criteria sooner than the 50 mM formulation. This may be attributed to lipid bilayer degradation in the HSPC formulation, as suggested by the HPLC/ELSD data, leading to dissipation of the loading gradient. It is likely that over extended storage time at an elevated temperature, the 20 mM formulation did not retain sufficient intraliposomal ammonium sulfate to allow satisfactory loading of $^{64}$Cu-4-DEAP-ATSC.

Figure 21B:
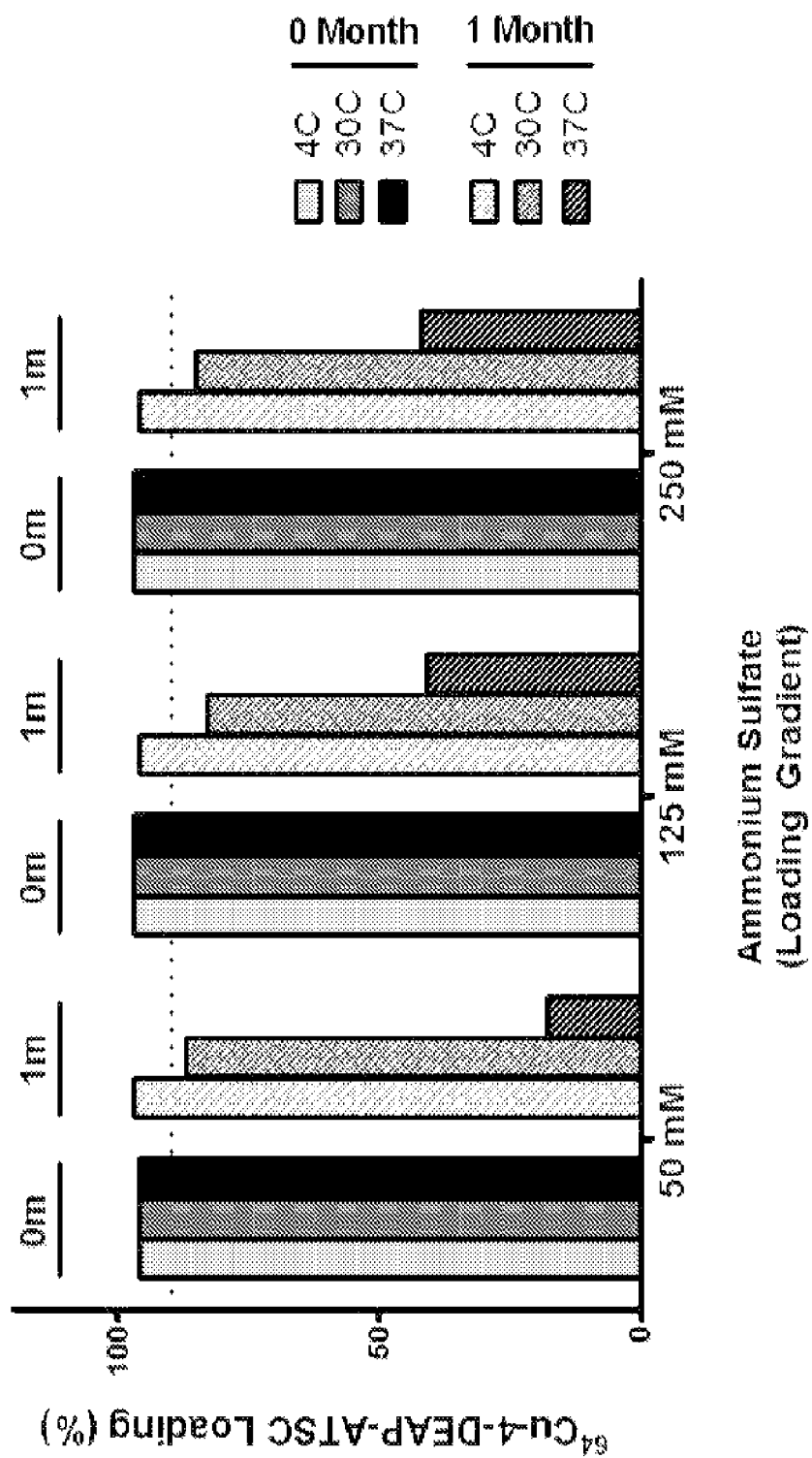

A similar study was performed with the DSPC liposome formulations, where DSPC liposomes containing 50, 125, or 250 mM of ammonium sulfate were included in the storage stability study (FIG. 21B). Following a 1-month storage period, liposomes that were stored at elevated temperatures also showed <90% of $^{64}$Cu:4-DEAP-ATSC loading. This is also attributed to significant degradation of the DSPC component, leading to gradient dissipation.

Figure 21C:
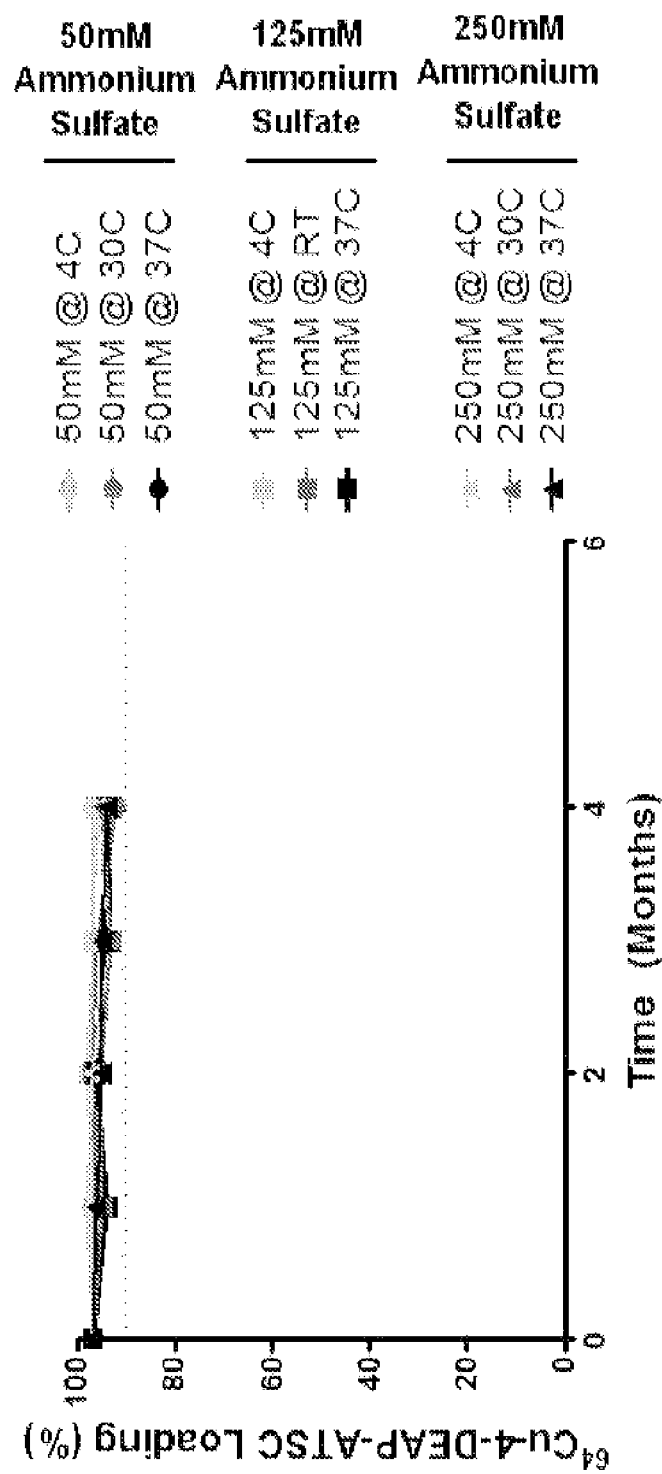

On the other hand, the sphingomyelin formulations were found to be stable over a 4-month storage at elevated temperatures (FIG. 21C). As described above, lipid degradation in the sphingomyelin formulations was insignificant, indicating increased storage stability of the formulations. This also indicates that the minor breakdown of the PEG- DSPE lipid detected in the sphingomyelin formulations did not compromise its storage stability functionally.

Figure 22:
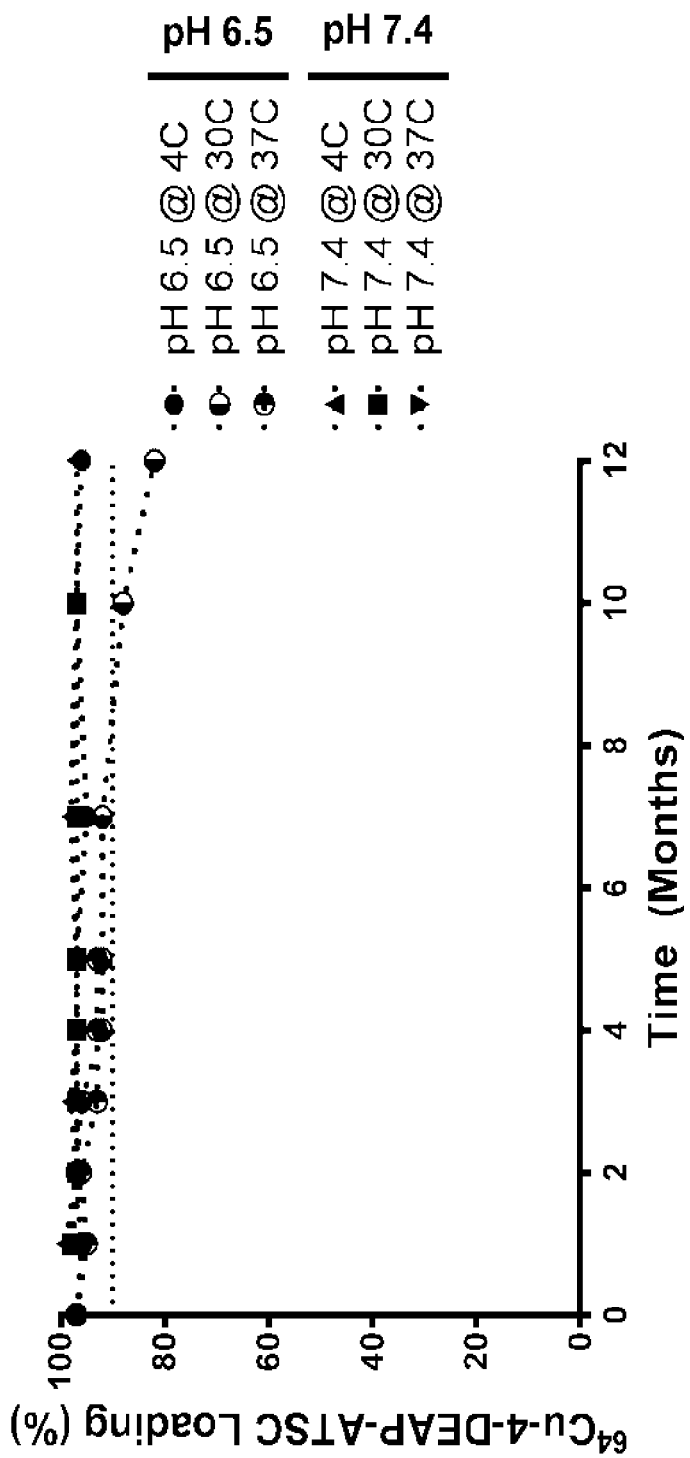
FIG. 22 is a graph showing the effect of storage pH on the storage stability of sphingomyelin liposomes over a four-month period, with loadability of the liposomes as a functional measurement.

Example 20: Storage Stability of Excipient Liposome Formulated in Varying Storage pH The effect of storage pH on the storage stability of sphingomyelin liposomes is illustrated in FIG. 22. Over a 12-month storage, the liposomes retain loadability at a storage pH of 6.5-7.4 when stored refrigerated at 2-8° C. Similar results were obtained in other pH 6.5 and pH 7.4 formulations listed in the table above. When stored at elevated temperature (30° C.), at pH 6.5 the liposomes start to show a $^{64}$Cu:4-DEAP-ATSC loading dropping below 90%.

Example 21: Liposome A as an Imaging Marker for Predicting Patient Treatment Response to Liposomal Therapeutics Mice bearing BT474-M3 tumors (inoculated at mammary fat pad and subcutaneous) were injected intravenously with Liposome A 24 h prior to Liposome B treatment. PET/CT imaging was performed at 16 h post Liposome A injection, and tumor uptake (% i.d./g) of Liposome A was determined from the PET data set by measuring radioactivity in the volume of interest (V01) (i.e. tumor regions). The mice were then treated with Liposome B (q7d) for 3 weeks at 3 mg/kg. Response to Liposome B treatment was quantified as tumor volume changes measured over a 2-month period by MRI and caliper measurement.

Figure 23:
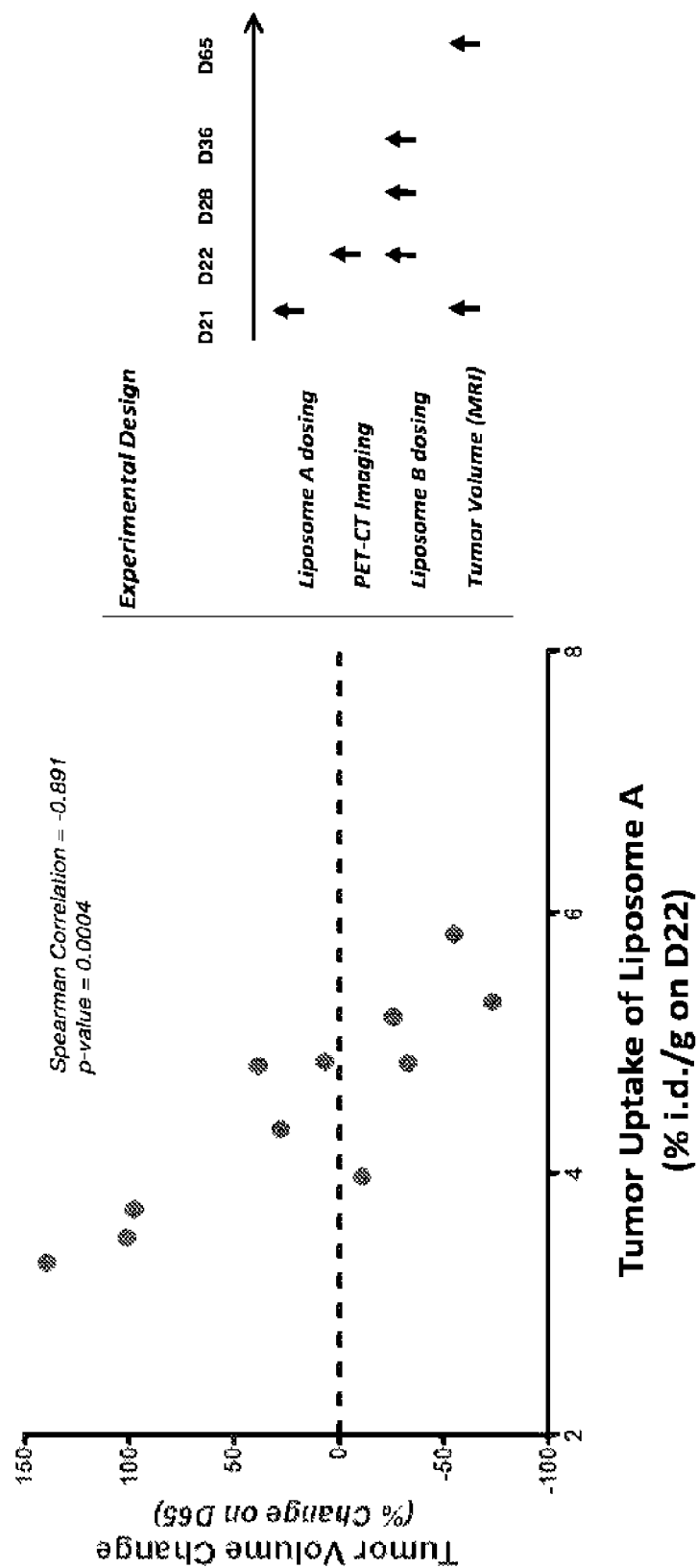
FIG. 23 is a graph showing that Liposome A is an imaging marker for predicting patient treatment response to liposomal therapeutic. The graph shows correlation between tumor uptake of Liposome A to treatment response to Liposome B.

Tumor deposition of Liposome A was found to range between 3-6% i.d./g, which is comparable to tumor uptake levels of Liposome B. As shown in FIG. 23, tumor deposition of Liposome A correlates with treatment response to Liposome B (Spearman correlation coefficient of −0.891 and a p-value of 0.0004). Specifically, increased Liposome A accumulation in tumors predicted for improved tumor growth inhibition following Liposome B treatment.

Example 22: Liposome A as an Imaging Marker for Monitoring Changes in Tumor Deposition after Treatment Mice bearing BT474-M3 tumors (inoculated at mammary fat pad and subcutaneous) were injected intravenously with Liposome A 24 h prior to Liposome B treatment for 3 weeks (3 doses of Liposome A, and 3 doses of Liposome B). For each dose of Liposome A, PET/CT imaging was performed at 16 h post-injection, and tumor uptake (% i.d./g) of Liposome A was determined from the PET data set using VOI analysis.

Figure 24A:
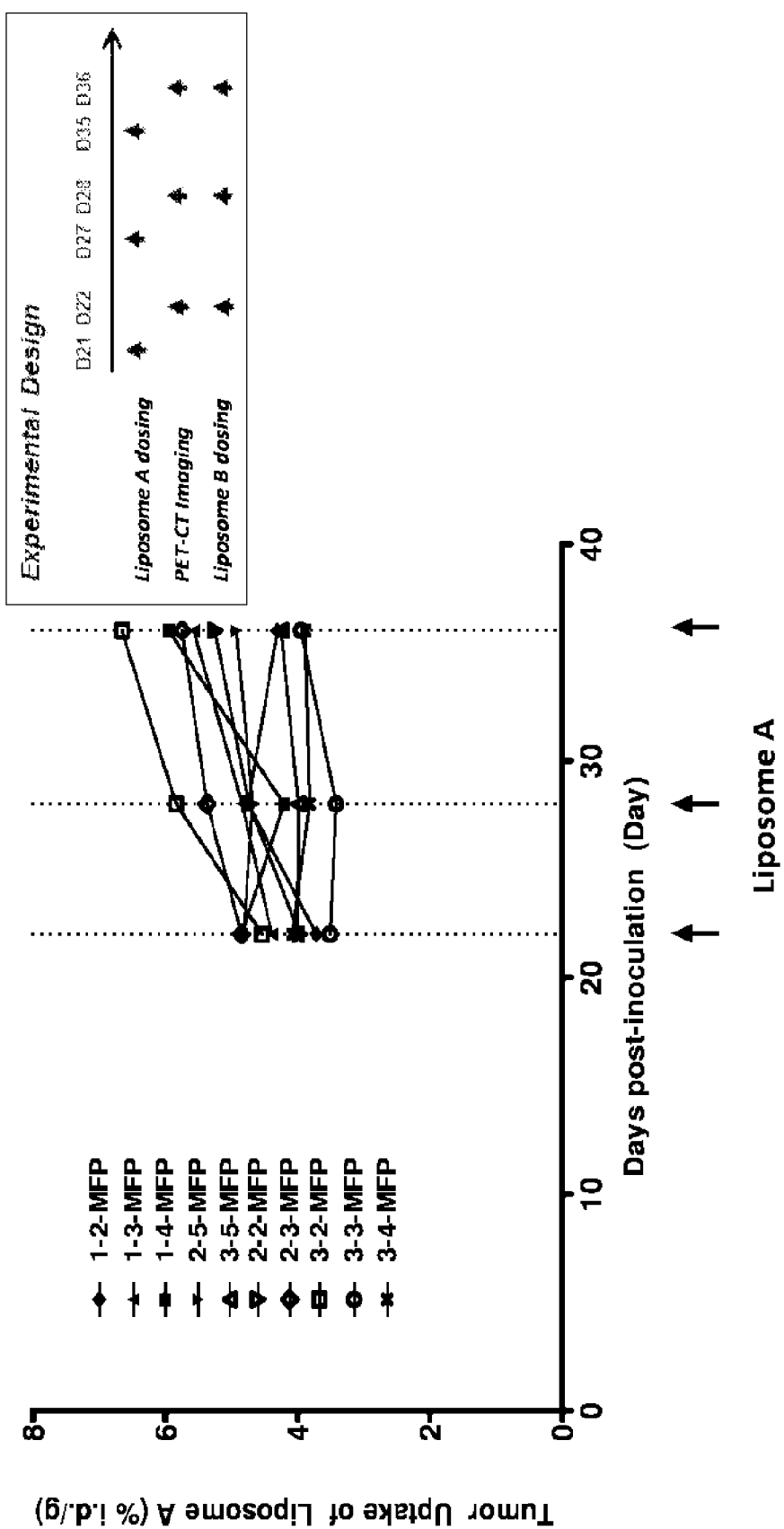
FIG. 24A is a graph showing changes in tumor deposition of Liposome A in mammary fat pad tumors.
Figure 24B:
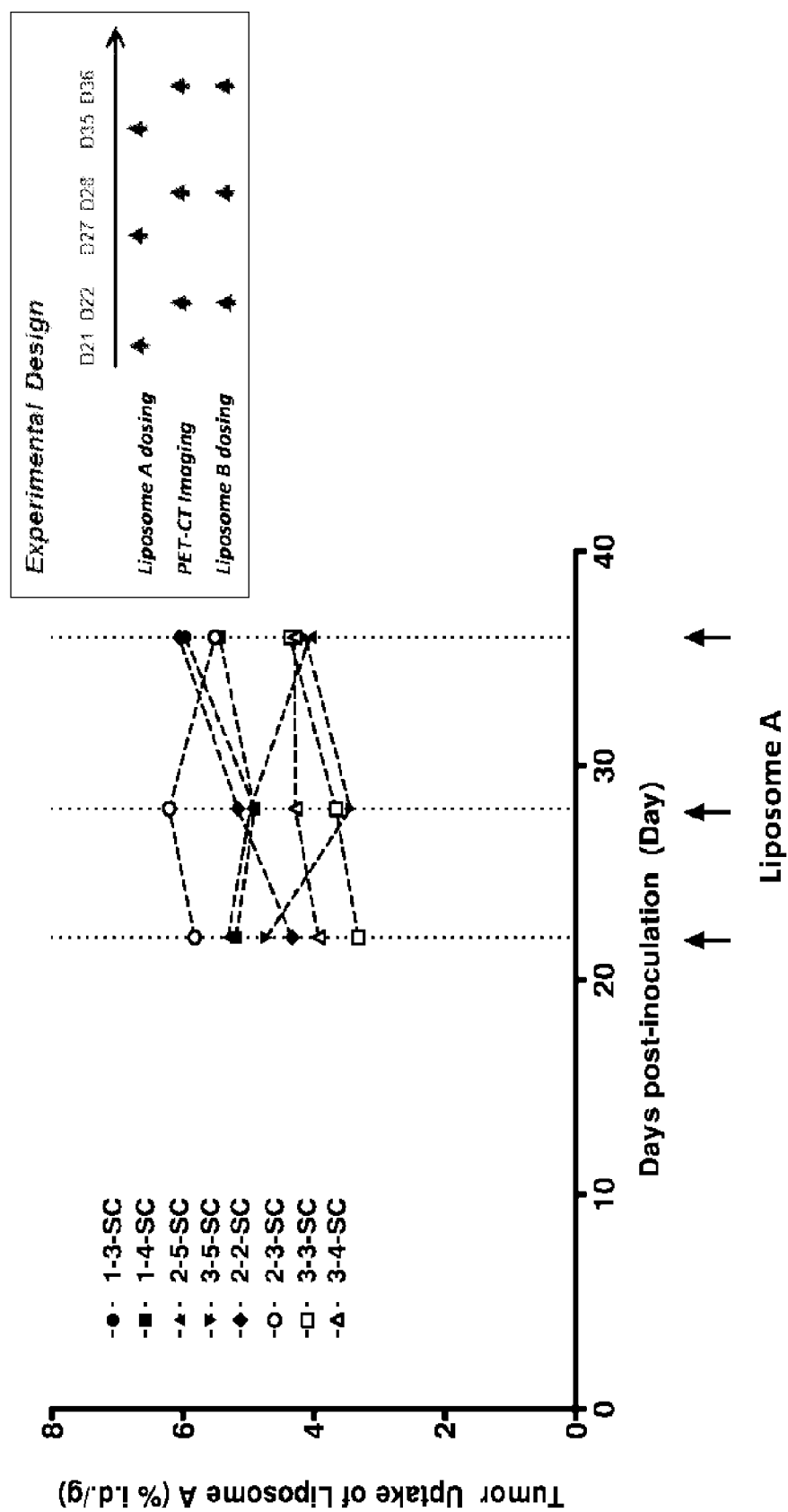
FIG. 24B is a graph showing changes in tumor deposition of Liposome A in subcutaneous tumors.
Figure 24C:
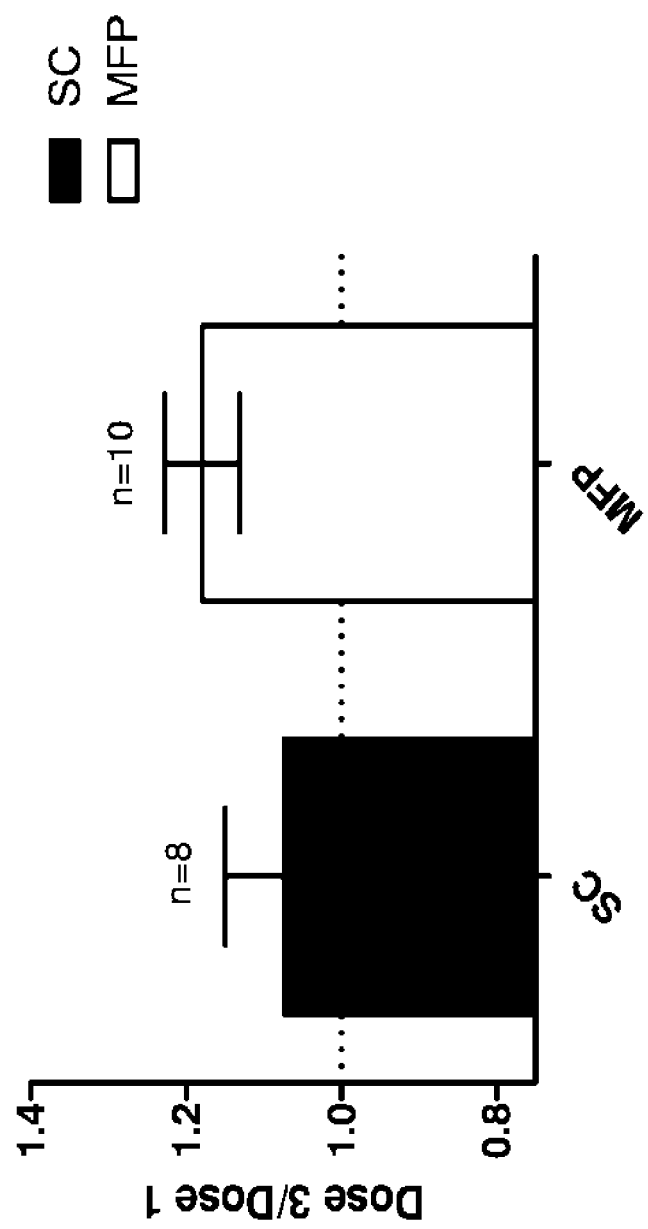
FIG. 24C is a graph showing changes in tumor deposition of Liposome A in a BT474-M3 mouse xenograft tumor model and comparison of dose 3 to dose 1.

As shown in FIG. 24, changes in tumor deposition of Liposome A can be detected in mammary fat pad (FIG. 24A) and subcutaneous (FIG. 24B) tumors from the PET data set following consecutive doses of Liposome B compared to baseline uptake (at day 22, "D22"). In the instance where tumor deposition of Liposome A dose 3 (D36) was compared to dose 1 (D22), an increased in the tumor uptake of the liposome was observed according to 2-way ANOVA (p=0.0003) for both subcutaneous and mammary fat pad tumors (FIG. 24C).

Example 23: In Vivo Stability of 64Cu:4-DEAP-ATSC-Loaded Liposomes

Figure 27A:
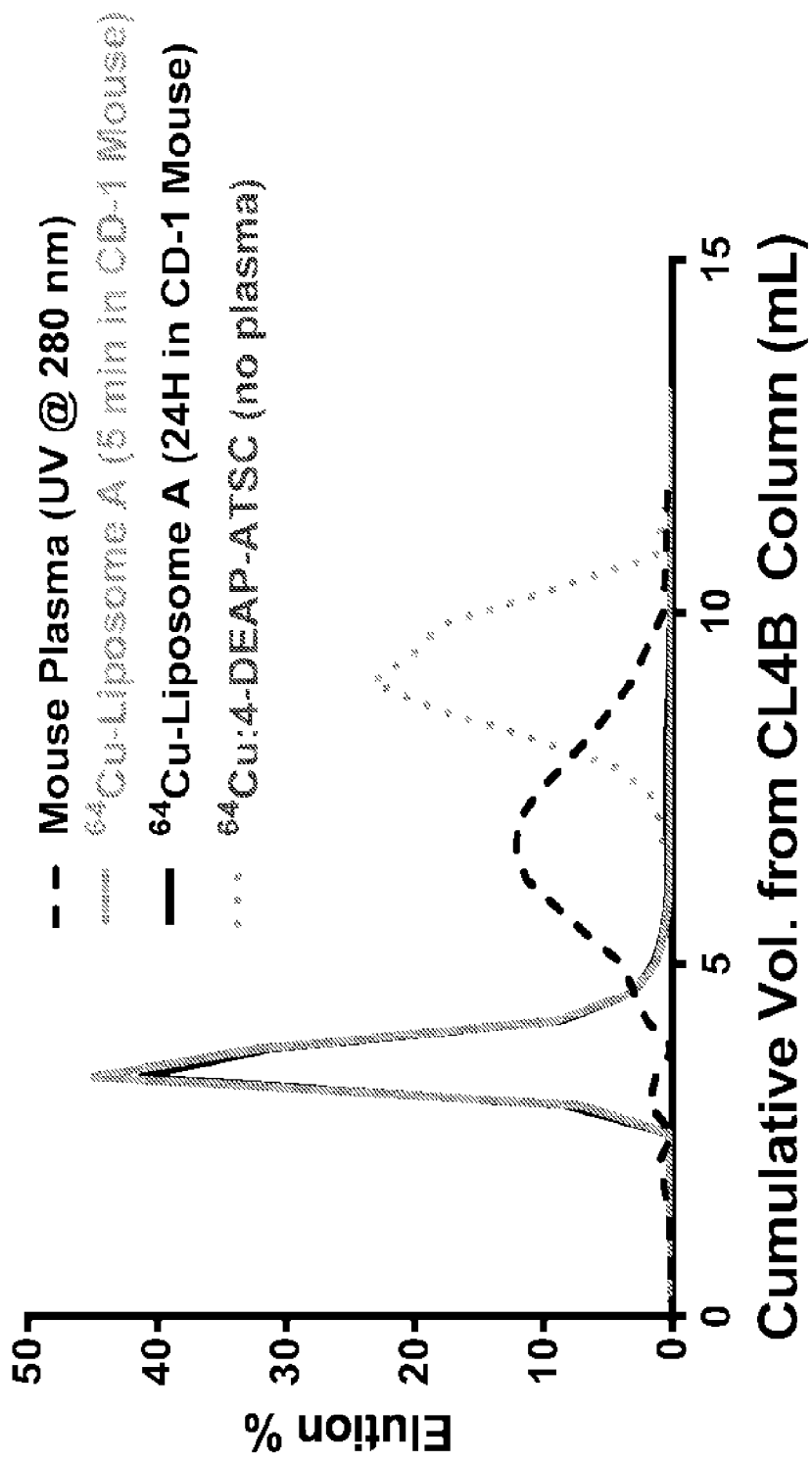
FIG. 27A is a graph showing the in vivo stability of Liposome A after injection into CD-1 mice.
Figure 27B:
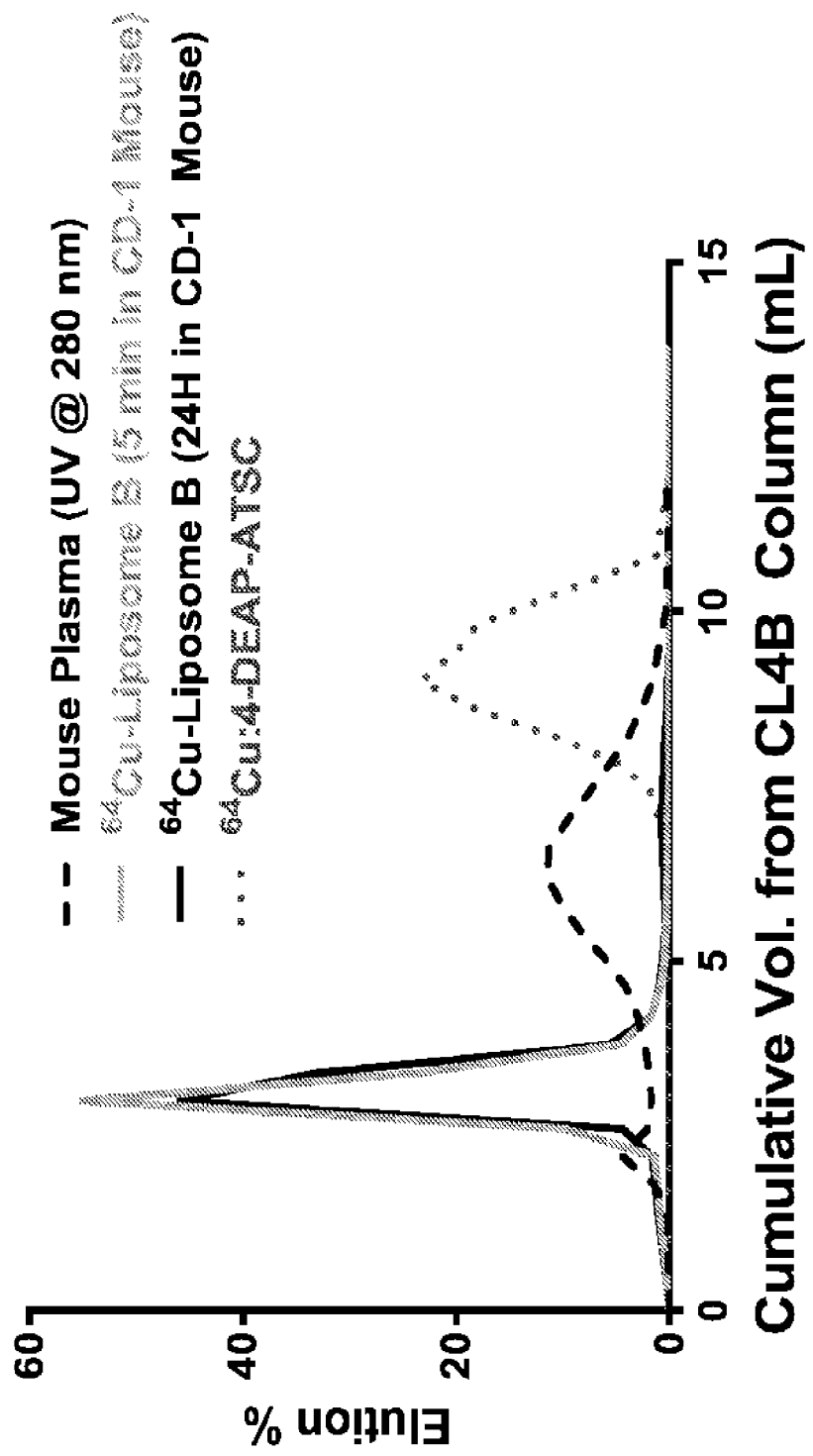
FIG. 27B is a graph showing the in vivo stability of Liposome B after injection into CD-1 mice.
Figure 27C:
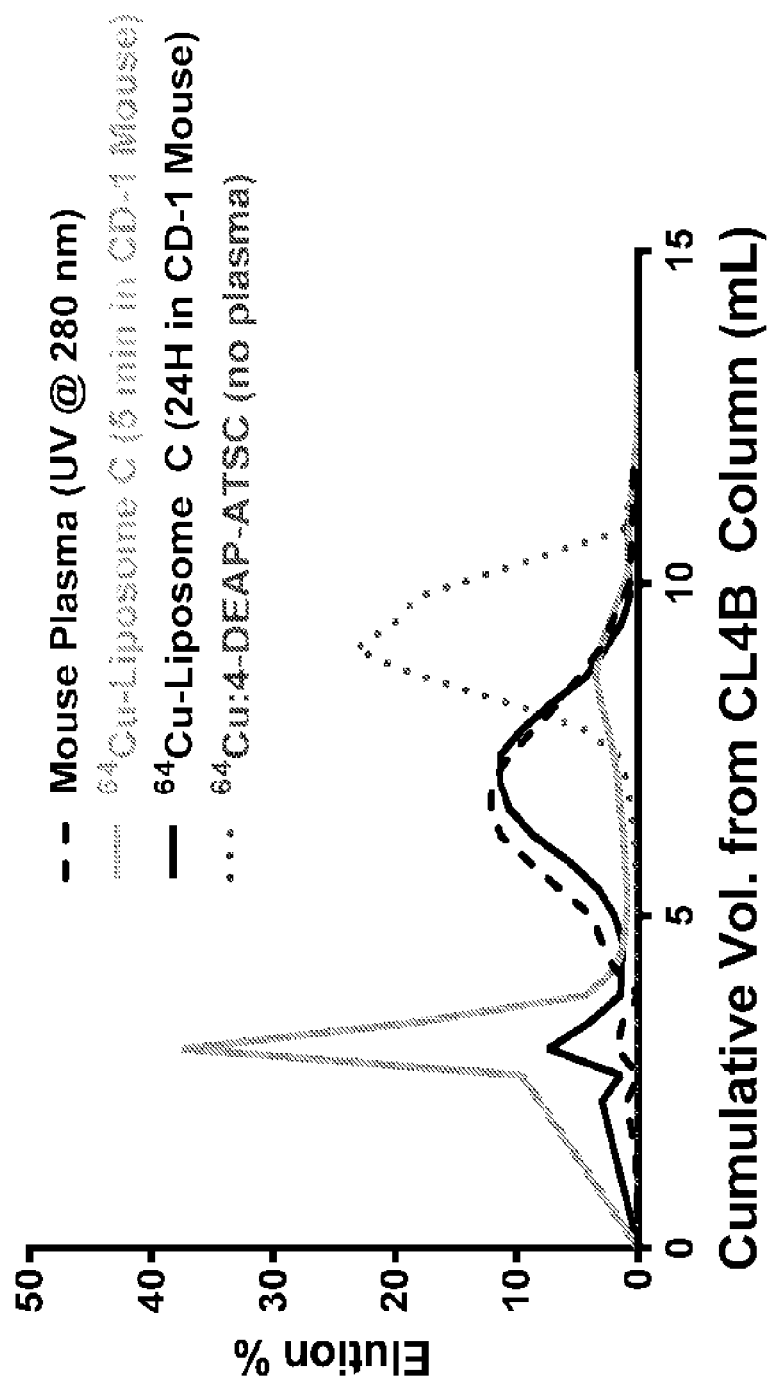
FIG. 27C is a graph showing the in vivo stability of Liposome C after injection into CD-1 mice.

The in vivo stability of 64Cu:4-DEAP-ATSC-loaded Liposome A (FIG. 27A), Liposome B (FIG. 27B), and Liposome C (FIG. 27C) were also examined in CD-1 mouse, up to 24 hours post-injection. CD-1 naïve mice were injected with $^{64}$Cu:4-DEAP-ATSC-loaded Liposome A, $^{64}$Cu:4-DEAP-ATSC-loaded Liposome B, and $^{64}$Cu:4-DEAP-ATSC-loaded Liposome C via tail vein injection (100-200 µCi/mouse, 20 µmol phospholipid/kg). At 5 minutes and 24 hours post-injection, blood was collected via cardiac puncture, and was subsequently centrifuged for plasma collection. Encapsulated (liposomal) radioactivity in the plasma was separated from released/unencapsulated radioactivity using size exclusion column (a CL4B column which allows for separating liposomal, protein, and $^{64}$Cu:4-DEAP-ATSC/ uncomplexed $^{64}$Cu fractions) similar to the method described in Example 8. The data show that Liposome A and Liposome B are highly stable in vivo with <6% of unencapsulated 64Cu detected up to 24 hours post-injection. For Liposome C, at 5 minutes and 24 hours post-injection, only 74% and 22% of the $^{64}$Cu in the plasma were detected in the liposomal fractions.

EQUIVALENTS

Those skilled in the art will recognize, or be able to ascertain using no more than routine experimentation, many equivalents of the specific embodiments described herein. Such equivalents are intended to be encompassed by the following claims. Any combinations of the embodiments disclosed in the dependent claims are contemplated to be within the scope of the invention.

INCORPORATION BY REFERENCE

Each and every, issued patent, patent application and publication referred to herein is hereby incorporated herein by reference in its entirety.

We claim:
1. A method of determining whether a patient having a tumor should be treated with a liposomal therapeutic agent, the method comprising:
(a) injecting the patient with a liposomal imaging agent in an amount sufficient to provide a dose of at least 0.1 µCi of radioactivity to the patient, the liposomal imaging agent comprising:
(i) liposomes in a pharmaceutically acceptable medium, said liposomes each having an interior space and a membrane separating said interior from said medium, said membrane comprising one or more lipids; and
(ii) a compound of formula II

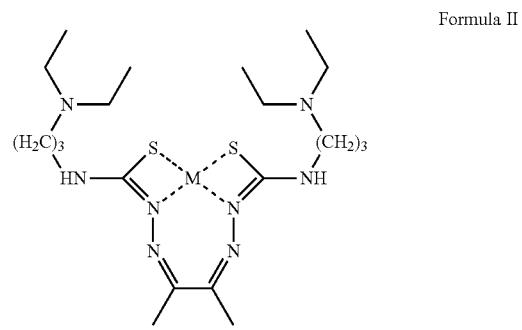

Formula II wherein M is a copper cation radioisotope detectable within the liposomal imaging agent, and wherein the compound of Formula II is entrapped in at least one liposome of the liposomes of (i);

(b) within 48 hours following the injection, scanning the location of the tumor using a scanning method that detects radiation emitted by the radioisotope to obtain an image; and (c) examining the image, wherein, if the image shows that the liposomal imaging agent is deposited in the tumor at levels higher than background, then the patient is determined to be a patient that should be treated with the liposomal therapeutic agent.

2. The method of claim 1 wherein background is determined by scanning tumor-free muscle tissue within 48 hours following the injection.

3. The method of claim 1, wherein, if the image shows that the liposomal imaging agent is deposited in the tumor at levels higher than background, then the patient is treated with the liposomal therapeutic agent and if the image shows that the liposomal imaging agent is not deposited in the tumor at levels higher than background, then the patient is not treated with the liposomal therapeutic agent.

4. The method according to claim 1, further comprising administering a liposomal therapeutic agent to the patient after detecting the liposomal imaging agent in the patient.

5. The method of claim 4, wherein the liposomal therapeutic agent is a liposomal antineoplastic therapeutic agent.

6. The method of claim 5, wherein the liposomal therapeutic agent is a liposomal irinotecan or liposomal doxorubicin.

7. The method of claim 1, wherein the patient is diagnosed with a neoplasia prior to injection of the liposomal imaging agent.

8. The method of claim 7, wherein the neoplasias is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, lymphoma, oligodenroglioma, schwannoma, meningioma, melanoma, neuroblastoma, and retinoblastoma.

9. The method of claim 8, wherein the neoplasia is breast cancer.

10. The method of claim 1, wherein M is $^{64}Cu^{2+}$, or $^{67}Cu^{2+}$.

11. The method of claim 10, wherein the liposomal imaging agent further comprises a membrane comprising DSPC, Cholesterol, and poly(ethylene glycol)(Mol. weight 2000)-derivatized distearoylphosphatidylethanolamine (PEG-DSPE).

12. The method of claim 11, wherein the liposomal imaging agent further comprises DSPC, Cholesterol and PEG-DSPE in a weight ratio of 3:1:1.

13. The method of claim 12, wherein the liposomal imaging agent has a pH of 5-8.

14. The method of claim 1, wherein the liposomal imaging agent further comprises sucrose octasulfate encapsulated within the liposomes.

15. The method of claim 11, wherein the liposomal imaging agent comprises sucrose octasulfate encapsulated with the compound of formula (II) within the liposome formed from DSPC, Cholesterol, and PEG-DSPE.

16. A method of treating a patient having a tumor, the method comprising:

(a) injecting the patient with a liposomal imaging agent in an amount sufficient to provide a dose of at least 0.1 μCi of radioactivity to the patient, the liposomal imaging agent comprising:

(i) liposomes in a pharmaceutically acceptable medium, said liposomes each having an interior space and a membrane separating said interior from said medium, said membrane comprising DSPC, cholesterol and PEG-DSPE in a weight ratio of 3:1:1; and (ii) a compound of formula II

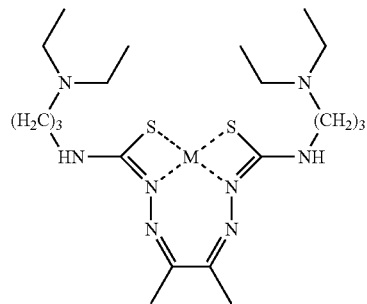

Formula II wherein M is $^{64}Cu^+$ and the compound of Formula II is entrapped in at least one liposome of the liposomes of (i);

(b) within 48 hours following the injection, scanning the location of the tumor using a scanning method that detects radiation emitted by the radioisotope to obtain an image; and (c) examining the image to determine whether the patient should be treated with a liposomal therapeutic agent, wherein, if the image shows that the liposomal imaging agent is deposited in the tumor at levels higher than background, then the patient is determined to be a patient that should be treated with the liposomal therapeutic agent.

17. The method of claim 16, wherein the liposomal therapeutic agent is an antineoplastic agent selected from the group consisting of liposomal irinotecan and liposomal doxorubicin.

18. The method of claim 16, wherein the patient is diagnosed with a neoplasia prior to injection of the liposomal imaging agent.

19. The method of claim 18, wherein the neoplasias is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, lymphoma, oligodenroglioma, schwannoma, meningioma, melanoma, neuroblastoma, and retinoblastoma.

20. The method of claim 19, wherein the neoplasia is breast cancer.

* * * * *